(12) United States Patent
Movassaghi et al.

(10) Patent No.: US 9,962,383 B2
(45) Date of Patent: *May 8, 2018

(54) COMPOUNDS, COMPOSITIONS AND METHODS OF AGELASTATIN ALKALOIDS

(71) Applicants: Massachusetts Institute of Technology, Cambridge, MA (US); The Board of Trustees of the University of Illinois, Urbana, IL (US)

(72) Inventors: Mohammad Movassaghi, Arlington, MA (US); Paul J. Hergenrother, Champaign, IL (US)

(73) Assignees: Massachusetts Institute of Technology, Cambridge, MA (US); The Board of Trustees of the University of Illionois, Urbana, IL (US)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/255,224

(22) Filed: Sep. 2, 2016

(65) Prior Publication Data
US 2017/0143708 A1    May 25, 2017

Related U.S. Application Data

(63) Continuation of application No. 14/490,146, filed on Sep. 18, 2014, now Pat. No. 9,434,736.

(60) Provisional application No. 61/880,018, filed on Sep. 19, 2013.

(51) Int. Cl.
*A61K 31/498* (2006.01)
*A61K 31/4985* (2006.01)

(52) U.S. Cl.
CPC ................. *A61K 31/4985* (2013.01)

(58) Field of Classification Search
CPC .................................................. A61K 3/4985
See application file for complete search history.

(56) References Cited

U.S. PATENT DOCUMENTS

| | | | |
|---|---|---|---|
| 9,434,736 B2 | 9/2016 | Movassaghi et al. | |
| 9,464,093 B2 | 10/2016 | Tun et al. | |
| 2015/0274742 A1* | 10/2015 | Tun ...................... | C07D 487/14 514/250 |

FOREIGN PATENT DOCUMENTS

| | | | |
|---|---|---|---|
| WO | WO 2004/106343 A2 | 12/2004 | |
| WO | WO 2004/106343 A3 | 12/2004 | |
| WO | WO 2006055578 A2 * | 5/2006 | ........... C07D 487/14 |
| WO | WO 2008/078109 A2 | 7/2008 | |
| WO | WO 2008/078109 A3 | 7/2008 | |
| WO | WO 2014/059314 A1 | 4/2014 | |

OTHER PUBLICATIONS

Movassaghi et al., Chem. Sci. 1, 561-66 (2010).*
Goldstraw et al., Lancet 378, 1727-40 (2011).*
Anderson et al., "Studies on Total Synthesis of the Cytotoxic Marine Alkaloid Agelastatin A," J. Org. Chem., 63:7594-7595 (1998).
Choi et al., "Agelastatin A (AgA), a Marine Sponge Derived Alkaloid, Inhibits Wnt/Beta-Catenin Signaling and Selectively Induces Apoptosis in Chronic Lymphocytic Leukemia Independently of p53," Blood (ASH Annual Meeting Abstracts), 118:Abstract 1786, 2 pages (2011).
D'Ambrosio et al., "The Active Centres of Agelastatin A, a Strongly Cytotoxic Alkaloid of the Coral Sea Axinellid Sponge *Agelas dendromorpha*, as Determined by Comparative Bioassays with Semisynthetic Derivatives," Helv. Chem. Acta, 79:727-735 (1996).
D'Ambrosia et al., "Agelastatin A, a New Skeleton Cytotoxic Alkaloid of the Oroidin Family. Isolation from the Axinellid Sponge *Agelas dendromorpha* of the Coral Sea," J. Chem. Soc., Chem. Commun., pp. 1305-1306 (1993).
Hale et al., "Enantiospecific Formal Total Synthesis of the Tumor and GSK-3b Inhibiting Alkaloid, (-)-Agelastatin A," Org. Lett., 5(16):2927-2930 (2003).
Mason et al., "Agelastatin A: a novel inhibitor of osteopontin-mediated adhesion, invasion, and colony formation," Mol. Cancer Ther., 7:548-558 (2008).
Pettit et al., "Antineoplastic Agents 470. Absolute Configuration of the Marine Sponge Bromopyrrole Agelastatin A," Oncol. Res., 15:11-20 (2005).
Han et al., "Synthesis and Anticancer Activity of All Known (-)-Agelastatin Alkaloids," The Journal of Organic Chemistry, 78, p. 11970-11984 (2013).
Jouanneau et al., "Derivatization of agelastatin A leading to bioactive analogs and a trifunctional probe," Bioorganic & Medicinal Chemistry Letters, 26, p. 2092-2097 (2016).
Kapoor, "Inhibition of osteopontin dependent carcinogenesis," J. Cancer Res. Clin. Oncol., 134, p. 927-928 (2008).
Li et al., "An integrated approach to the discovery of potent agelastatin A analogues for brain tumors: chemical synthesis and biological, physicochemical and CNS pharmacokinetic analyses," Med. Chem. Commun., 4, p. 1093-1098 (2013).
Li et al., "Pharmacokinetics of Agelastatin A in the central nervous system," Med. Chem. Commun., 3, p. 233-237, (2012).
Movassaghi et al., "Total Synthesis of All (-)-Agelastatin Alkaloids," 49, p. 391-396 (2012).
Stout et al., "Potent Fluorinated Agelastatin Analogues for Chronic Lymphocytic Leukemia: Design, Synthesis, and Pharmacokinetic Studies," J. Med. Chem., 57, p. 5085-5093 (2014).
Tilvi et al., "Agelastatin E, Agelastatin F, and Benzosceptrin C from the Marine Sponge *Agelas dendromorpha*," J. Nat. Prod., 73, p. 720-723 (2010).

* cited by examiner

*Primary Examiner* — Theodore R. West
(74) *Attorney, Agent, or Firm* — Cooley LLP

(57) ABSTRACT

The present invention, among other things, provides compounds, compositions and methods for treatment of cancer. In some embodiments, the present invention provides methods for treating blood cancer using agelastatin alkaloids.

27 Claims, 9 Drawing Sheets

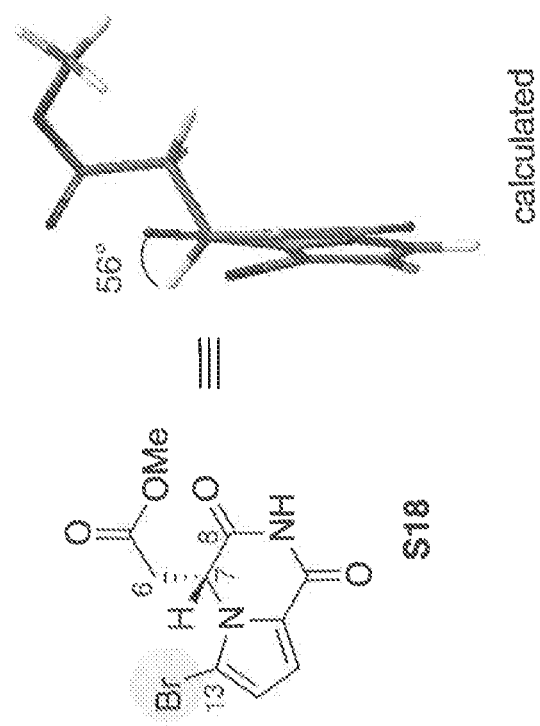
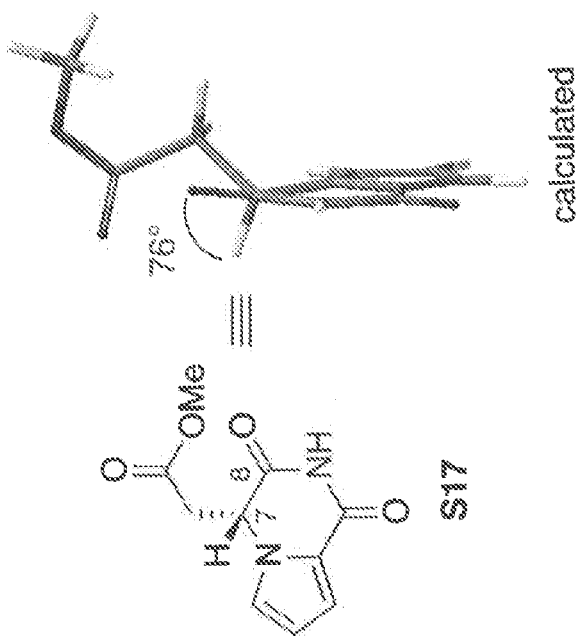
Fig. 5

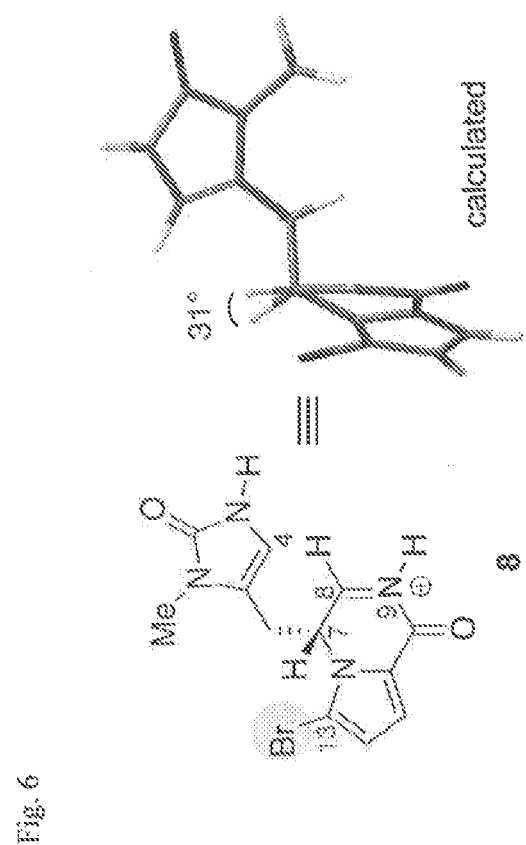
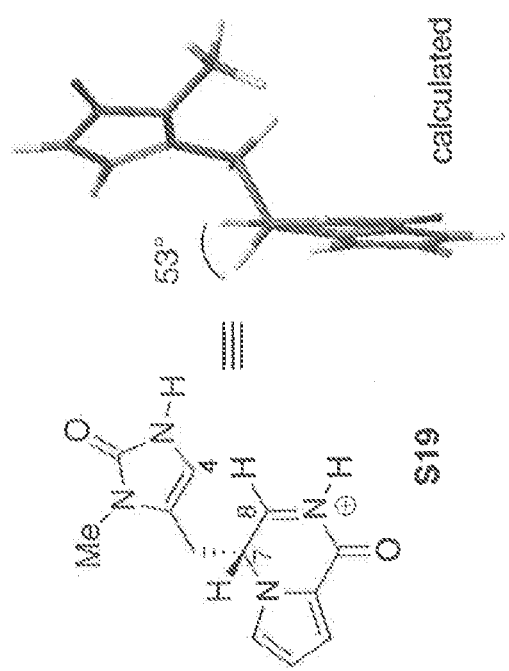
Fig. 6

Fig. 9
View 1:
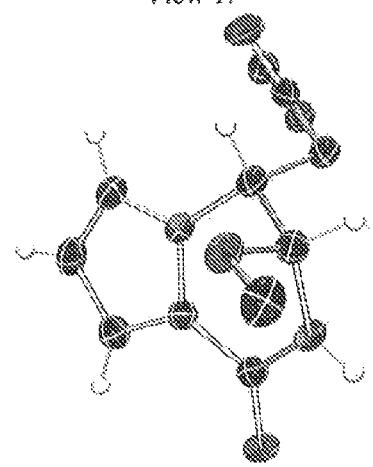
View 2:
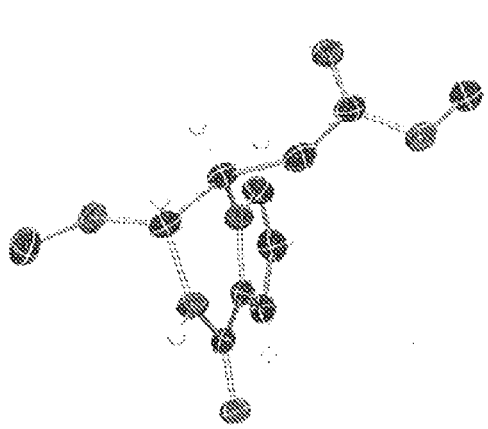
View 3:
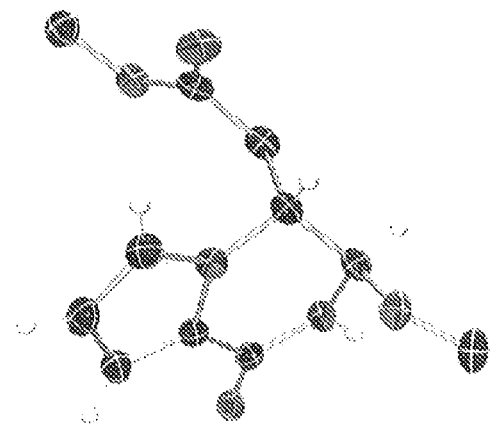

COMPOUNDS, COMPOSITIONS AND METHODS OF AGELASTATIN ALKALOIDS

RELATED APPLICATIONS

This application is a continuation of U.S. patent application Ser. No. 14/490,146, filed on Sep. 18, 2014, which claims the benefit of U.S. Provisional Patent Application No. 61/880,018, filed on Sep. 19, 2013. The entire contents of the each aforementioned application are incorporated herein by reference in its entirety.

STATEMENT REGARDING FEDERALLY SPONSORED RESEARCH OR DEVELOPMENT

This invention was made with government support under Grant No. GM074825 awarded by the National Institutes of Health. The government has certain rights in the invention.

FIELD OF THE INVENTION

The present invention generally relates to, among other things, compounds, compositions and methods for treating cancer.

SUMMARY

Among other things, the present invention provides compounds, compositions and methods for treating a blood cancer. In some embodiments, the present invention provides a method for treating a blood cancer. In some embodiments, the present invention provides a method for treating a blood cancer in a subject in need thereof, comprising administering to the subject a therapeutically effective amount of an agelastatin alkaloid.

In some embodiments, the present invention provides a pharmaceutical composition of a compound of formula I:

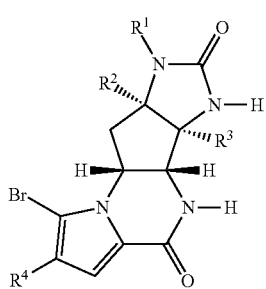

or a pharmaceutically acceptable salt thereof, wherein each variable is independently described in detail, infra. In some embodiments, a provided composition is for treating blood cancers.

In some embodiments, the present invention provides a method for treating a blood cancer in a subject in need thereof, comprising administering to the subject a therapeutically effective amount of a compound of formula I:

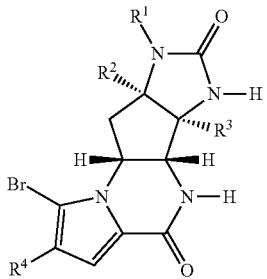

or a pharmaceutically acceptable salt thereof, wherein each variable is independently described in detail, infra.

In some embodiments, the present invention provides a method for inhibiting growth of blood cancer cells. In some embodiments, the present invention provides a method for inhibiting growth of blood cancer cells, comprising administering a compound of formula I:

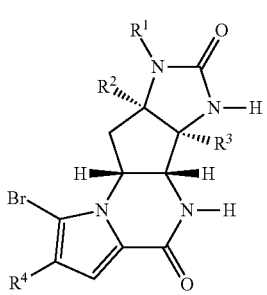

or a pharmaceutically acceptable salt thereof, wherein each variable is independently described in detail, infra.

In some embodiments, the present invention provides a method for inhibiting proliferation of blood cancer cells. In some embodiments, the present invention provides a method for inhibiting proliferation of blood cancer cells, comprising administering a compound of formula I:

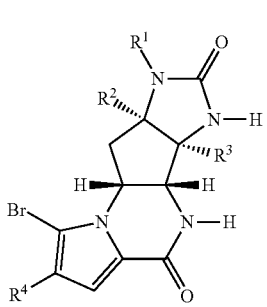

or a pharmaceutically acceptable salt thereof, wherein each variable is independently described in detail, infra.

In some embodiments, the present invention provides a method for promoting apoptosis of blood cancer cells. In some embodiments, the present invention provides a method for promoting apoptosis of blood cancer cells, comprising administering a compound of formula I:

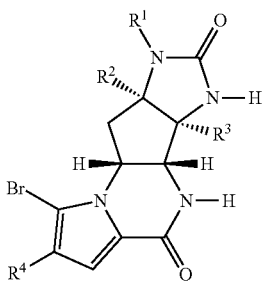

or a pharmaceutically acceptable salt thereof, wherein each variable is independently described in detail, infra.

In some embodiments, the present invention provides a method for arresting cell cycle in blood cancer cells. In some embodiments, the present invention provides a method for arresting cell cycle in blood cancer cells, comprising administering a compound of formula I:

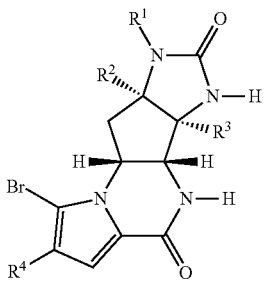

or a pharmaceutically acceptable salt thereof, wherein each variable is independently described in detail, infra.

In some embodiments, the present invention provides a method for inducing arrest in G2/M phase in blood cancer cells. In some embodiments, the present invention provides a method for inducing arrest in G2/M phase in blood cancer cells, comprising administering a compound of formula I:

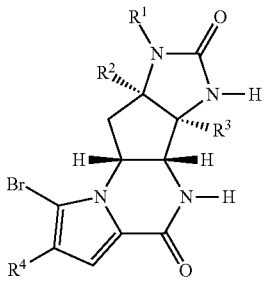

or a pharmaceutically acceptable salt thereof, wherein each variable is independently described in detail, infra.

BRIEF DESCRIPTION OF THE DRAWING

FIG. 5. Minimized energy conformations of imides S17 and S18 (Spartan 06, Density Functional, B3LYP, 6·31G* was used for the calculation).

FIG. 6. Minimized energy conformations of acyliminium ion S19 and 8 (Spartan 06, Density Functional, B3LYP, 6·31G* was used for the calculation).

FIG. 9. Crystal Structure of 13-desbromo-methylester S25.

DETAILED DESCRIPTION OF CERTAIN EMBODIMENTS

Figure 1:
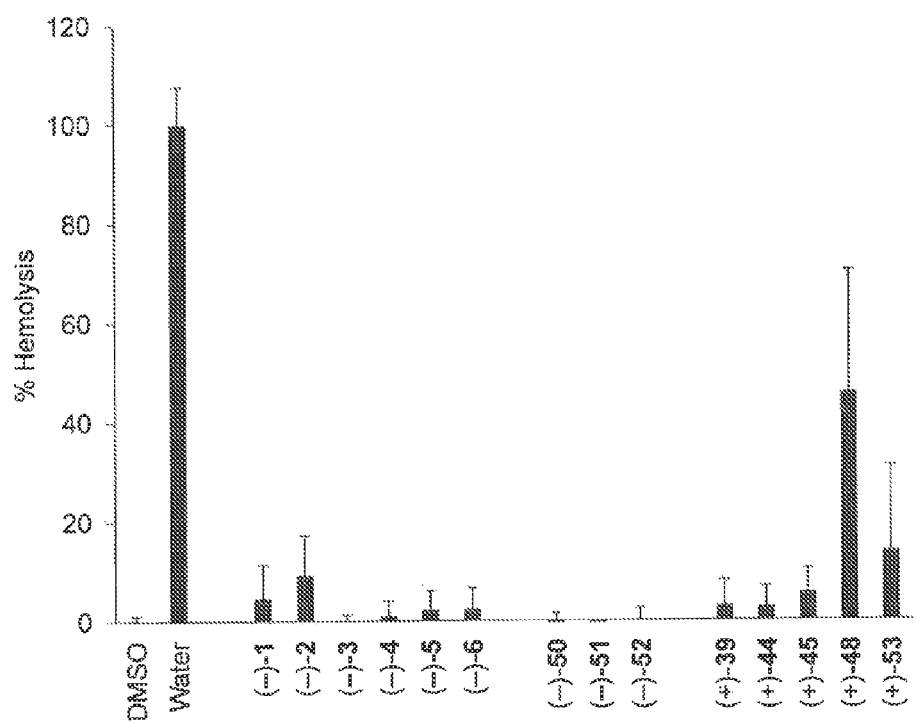
FIG. 1. Hemolytic activity of (−)-agelastatins A-F and advanced intermediates. Compounds were tested at 333 μM and hemolysis was evaluated after 2 h. DMSO and water served as the negative and positive controls for hemolysis, respectively. Error bars represent standard deviation of the mean, n=3.

1. General Description of Certain Embodiments of the Invention

Among other things, the present invention provides compounds, compositions and methods for treating blood cancers.

In some embodiments, the present invention provides agelastatin compounds. In some embodiments, the present invention provides a composition comprising an agelastatin compound. In some embodiments, an agelastatin compound in a provided composition has the structure of formula I. In some embodiments, the present invention provides a pharmaceutical composition of a compound of formula I:

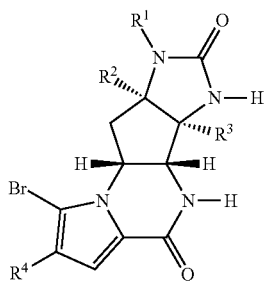

or a pharmaceutically acceptable salt thereof, wherein:
  $R^1$ is —H or —CH$_3$;
  $R^2$ is —OH or —OCH$_3$;
  $R^3$ is —H or —OH; and
  $R^4$ is —H, or —Br when $R^1$ is —CH$_3$.

In some embodiments, the present invention provides a composition for treating a blood cancer in a subject in need thereof, comprising a compound of formula I:

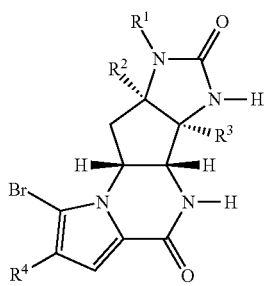

or a pharmaceutically acceptable salt thereof, wherein:
  $R^1$ is —H or —CH$_3$;
  $R^2$ is —OH or —OCH$_3$;
  $R^3$ is —H or —OH; and
  $R^4$ is —H, or —Br when $R^1$ is —CH$_3$.

In some embodiments, the present invention recognizes that agelastatin alkaloids, e.g., a compound of formula I, are particularly effective and useful for treating blood cancer. In some embodiments, the present invention provides methods for treating a blood cancer in a subject in need thereof, comprising administering to the subject a therapeutically effective amount of an agelastatin alkaloid, or a pharmaceutically acceptable salt thereof. In some embodiments, the present invention provides methods for inhibiting growth of blood cancer cells, comprising administering an agelastatin alkaloid, or a pharmaceutically acceptable salt thereof. In some embodiments, the present invention provides methods for inhibiting proliferation of blood cancer cells, comprising administering an agelastatin alkaloid, or a pharmaceutically acceptable salt thereof. In some embodiments, the present invention provides methods for promoting apoptosis of blood cancer cells, comprising administering an agelastatin alkaloid, or a pharmaceutically acceptable salt thereof. In some embodiments, the present invention provides methods for arresting cell cycle in blood cancer cells, comprising administering an agelastatin alkaloid, or a pharmaceutically acceptable salt thereof. In some embodiments, the present invention provides methods for arresting G2/M phase in blood cancer cells, comprising administering an agelastatin alkaloid, or a pharmaceutically acceptable salt thereof. In some embodiments, an agelastatin alkaloid in provided method has the structure of formula I.

In some embodiments, the present invention provides a method for treating a blood cancer in a subject in need thereof, comprising administering to the subject a therapeutically effective amount of a compound of formula I:

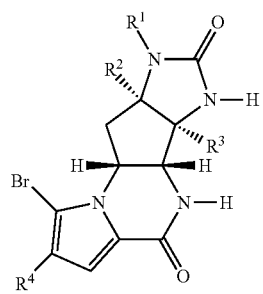

or a pharmaceutically acceptable salt thereof, wherein:
  $R^1$ is —H or —CH$_3$;
  $R^2$ is —OH or —OCH$_3$;
  $R^3$ is —H or —OH; and
  $R^4$ is —H, or —Br when $R^1$ is —CH$_3$.

In some embodiments, the present invention provides a method for inhibiting growth of blood cancer cells. In some embodiments, the present invention provides a method for inhibiting growth of blood cancer cells, comprising administering a compound of formula I:

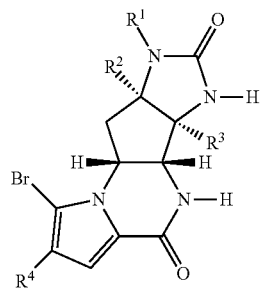

or a pharmaceutically acceptable salt thereof, wherein:
  $R^1$ is —H or —CH$_3$;
  $R^2$ is —OH or —OCH$_3$;
  $R^3$ is —H or —OH; and
  $R^4$ is —H, or —Br when $R^1$ is —CH$_3$.

In some embodiments, the present invention provides a method for inhibiting proliferation of blood cancer cells. In some embodiments, the present invention provides a method for inhibiting proliferation of blood cancer cells, comprising administering a compound of formula I:

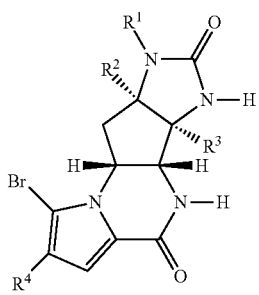

or a pharmaceutically acceptable salt thereof, wherein:
  $R^1$ is —H or —$CH_3$;
  $R^2$ is —OH or —$OCH_3$;
  $R^3$ is —H or —OH; and
  $R^4$ is —H, or —Br when $R^1$ is —$CH_3$.

In some embodiments, the present invention provides a method for promoting apoptosis of blood cancer cells. In some embodiments, the present invention provides a method for promoting apoptosis of blood cancer cells, comprising administering a compound of formula I:

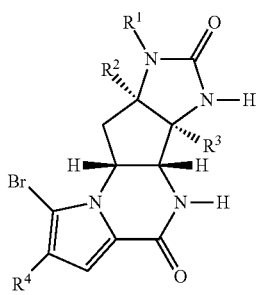

or a pharmaceutically acceptable salt thereof, wherein:
  $R^1$ is —H or —$CH_3$;
  $R^2$ is —OH or —$OCH_3$;
  $R^3$ is —H or —OH; and
  $R^4$ is —H, or —Br when $R^1$ is —$CH_3$.

In some embodiments, the present invention provides a method for arresting cell cycle in blood cancer cells. In some embodiments, the present invention provides a method for arresting cell cycle in blood cancer cells, comprising administering a compound of formula I:

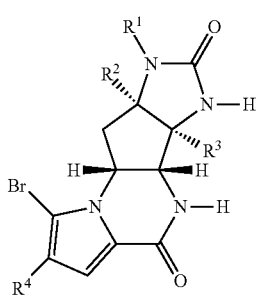

or a pharmaceutically acceptable salt thereof, wherein:
  $R^1$ is —H or —$CH_3$;
  $R^2$ is —OH or —$OCH_3$;
  $R^3$ is —H or —OH; and
  $R^4$ is —H, or —Br when $R^1$ is —$CH_3$.

In some embodiments, the present invention provides a method for inducing arrest in G2/M phase in blood cancer cells. In some embodiments, the present invention provides a method for inducing arrest in G2/M phase in blood cancer cells, comprising administering a compound of formula I:

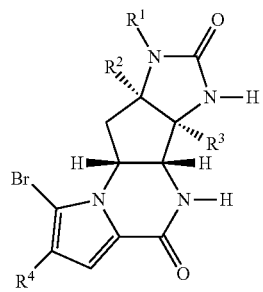

or a pharmaceutically acceptable salt thereof, wherein:
  $R^1$ is —H or —$CH_3$;
  $R^2$ is —OH or —$OCH_3$;
  $R^3$ is —H or —OH; and
  $R^4$ is —H, or —Br when $R^1$ is —$CH_3$.

2. Definitions

Compounds of the present invention include those described generally herein, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, 93$^{rd}$ Ed. Additionally, general principles of organic chemistry are described in "Organic Chemistry", 2$^{nd}$ Ed, Thomas N. Sorrell, University Science Books, Sausalito: 2005, and "March's Advanced Organic Chemistry", 6$^{th}$ Ed., Smith, M. B. and March, J., John Wiley & Sons, New York: 2007, the entire contents of which are hereby incorporated by reference.

The term "aliphatic" or "aliphatic group", as used herein, means a straight-chain (i.e., unbranched) or branched, substituted or unsubstituted hydrocarbon chain that is completely saturated or that contains one or more units of unsaturation, or a monocyclic hydrocarbon, bicyclic hydrocarbon, or polycyclic hydrocarbon that is completely saturated or that contains one or more units of unsaturation, but which is not aromatic (also referred to herein as "carbocycle," "cycloaliphatic" or "cycloalkyl"), that has, unless otherwise specified, a single point of attachment to the rest of the molecule. Unless otherwise specified, aliphatic groups contain 1-30 aliphatic carbon atoms. In some embodiments, aliphatic groups contain 1-20 aliphatic carbon atoms. In other embodiments, aliphatic groups contain 1-10 aliphatic carbon atoms. In still other embodiments, aliphatic groups contain 1-5 aliphatic carbon atoms, and in yet other embodiments, aliphatic groups contain 1, 2, 3, or 4 aliphatic carbon atoms. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl.

The term "cycloaliphatic," as used herein, refers to saturated or partially unsaturated cyclic aliphatic monocyclic, bicyclic, or polycyclic ring systems, as described herein, having from 3 to 14 members, wherein the aliphatic ring system is optionally substituted as defined above and described herein. Cycloaliphatic groups include, without limitation, cyclopropyl, cyclobutyl, cyclopentyl, cyclopentenyl, cyclohexyl, cyclohexenyl, cycloheptyl, cycloheptenyl, cyclooctyl, cyclooctenyl, norbornyl, adamantyl, and cyclooctadienyl. In some embodiments, the cycloalkyl has 3-6 carbons. The terms "cycloaliphatic," may also include aliphatic rings that are fused to one or more aromatic or nonaromatic rings, such as decahydronaphthyl or tetrahydronaphthyl, where the radical or point of attachment is on the aliphatic ring. In some embodiments, a carbocyclic group is bicyclic. In some embodiments, a carbocyclic group is tricyclic. In some embodiments, a carbocyclic group is polycyclic. In some embodiments, "cycloaliphatic" (or "carbocycle" or "cycloalkyl") refers to a monocyclic $C_3$-$C_6$ hydrocarbon, or a $C_1$-$C_{10}$ bicyclic hydrocarbon that is completely saturated or that contains one or more units of unsaturation, but which is not aromatic, that has a single point of attachment to the rest of the molecule, or a $C_9$-$C_{16}$ tricyclic hydrocarbon that is completely saturated or that contains one or more units of unsaturation, but which is not aromatic, that has a single point of attachment to the rest of the molecule.

As used herein, the term "alkyl" is given its ordinary meaning in the art and may include saturated aliphatic groups, including straight-chain alkyl groups, branched-chain alkyl groups, cycloalkyl (alicyclic) groups, alkyl substituted cycloalkyl groups, and cycloalkyl substituted alkyl groups. In certain embodiments, a straight chain or branched chain alkyl has about 1-20 carbon atoms in its backbone (e.g., $C_1$-$C_{20}$ for straight chain, $C_2$-$C_{20}$ for branched chain), and alternatively, about 1-10. In some embodiments, a cycloalkyl ring has from about 3-10 carbon atoms in their ring structure where such rings are monocyclic, bicyclic or polycyclic, and alternatively about 5, 6 or 7 carbons in the ring structure. In some embodiments, an alkyl group may be a lower alkyl group, wherein a lower alkyl group comprises 1-4 carbon atoms (e.g., $C_1$-$C_4$ for straight chain lower alkyls).

As used herein, the term "alkenyl" refers to an alkyl group, as defined herein, having one or more double bonds.

As used herein, the term "alkynyl" refers to an alkyl group, as defined herein, having one or more triple bonds.

The term "heteroalkyl" is given its ordinary meaning in the art and refers to alkyl groups as described herein in which at least one carbon atom, optionally with one or more attached hydrogen atoms, is replaced with a heteroatom (e.g., oxygen, nitrogen, sulfur, phosphorus, selenium, boron and the like). Examples of heteroalkyl groups include, but are not limited to, alkoxy, poly(ethylene glycol)-, alkyl-substituted amino, tetrahydrofuranyl, piperidinyl, morpholinyl, etc. In some embodiments, a heteroatom may be oxidized (e.g., —S(O)—, —S(O)$_2$—, —N(O)—, —P(O)— and the like).

The term "aryl" used alone or as part of a larger moiety as in "aralkyl," "aralkoxy," or "aryloxyalkyl," refers to monocyclic, bicyclic or polycyclic ring systems having a total of five to fourteen ring members, wherein at least one ring in the system is aromatic and wherein each ring in the system contains 3 to 7 ring members. The term "aryl" may be used interchangeably with the term "aryl ring." In certain embodiments of the present invention, "aryl" refers to an aromatic ring system which includes, but not limited to, phenyl, biphenyl, naphthyl, binaphthyl, anthracyl and the like, which may bear one or more substituents. Also included within the scope of the term "aryl," as it is used herein, is a group in which an aromatic ring is fused to one or more non-aromatic rings, such as indanyl, phthalimidyl, naphthimidyl, phenanthridinyl, or tetrahydronaphthyl, and the like.

The terms "heteroaryl" and "heteroar-," used alone or as part of a larger moiety, e.g., "heteroaralkyl," or "heteroaralkoxy," refer to groups having 5 to 10 ring atoms (i.e., monocyclic or bicyclic), in some embodiments 5, 6, 9, or 10 ring atoms. In some embodiments, such rings have 6, 10, or 14 π electrons shared in a cyclic array; and having, in addition to carbon atoms, from one to five heteroatoms. The term "heteroatom" refers to nitrogen, oxygen, or sulfur, and includes any oxidized form of nitrogen or sulfur, and any quaternized form of a basic nitrogen. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. In some embodiments, a heteroaryl is a heterobiaryl group, such as bipyridyl and the like. The terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Non-limiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group may be mono- or bicyclic. The term "heteroaryl" may be used interchangeably with the terms "heteroaryl ring," "heteroaryl group," or "heteroaromatic," any of which terms include rings that are optionally substituted. The term "heteroaralkyl" refers to an alkyl group substituted by a heteroaryl, wherein the alkyl and heteroaryl portions independently are optionally substituted.

As used herein, the terms "heterocycle," "heterocyclyl," "heterocyclic radical," and "heterocyclic ring" are used interchangeably and refer to a stable 5- to 7-membered monocyclic or 7-10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or $^+$NR (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothienyl pyrrolidinyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle," "heterocyclyl," "heterocyclyl ring," "heterocyclic group," "heterocyclic moiety," and "heterocyclic radical," are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl. A heterocyclyl group may be mono- or bicyclic. The term "heterocyclylalkyl" refers to an alkyl group substituted by a heterocyclyl, wherein the alkyl and heterocyclyl portions independently are optionally substituted.

As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

The term "heteroatom" means one or more of boron, oxygen, sulfur, selenium, nitrogen, phosphorus, or silicon (including, any oxidized form of nitrogen, sulfur, selenium, phosphorus, or silicon; the quaternized form of any basic nitrogen; or a substitutable nitrogen of a heterocyclic ring, for example N (as in 3,4-dihydro-2H-pyrrolyl), NH (as in pyrrolidinyl) or NR' (as in N-substituted pyrrolidinyl)).

The term "unsaturated," as used herein, means that a moiety has one or more units of unsaturation.

The term "halogen" means F, Cl, Br, or I.

As described herein, compounds of the invention may contain "optionally substituted" moieties. In general, the term "substituted," whether preceded by the term "optionally" or not, means that one or more hydrogen atoms of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable," as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently halogen; —$(CH_2)_{0-4}R°$; —$(CH_2)_{0-4}OR°$; —$(CH_2)_{0-4}SR°$; —$(CH_2)_{0-4}S(O)R°$; —$O(CH_2)_{0-4}R°$, —O—$(CH_2)_{0-4}C(O)OR°$; —$(CH_2)_{0-4}CH(OR°)_2$; —$(CH_2)_{0-4}Ph$, which may be substituted with $R°$; —$(CH_2)_{0-4}O(CH_2)_{0-1}Ph$ which may be substituted with $R°$; —CH=CHPh, which may be substituted with $R°$; —$(CH_2)_{0-4}O(CH_2)_{0-1}$-pyridyl which may be substituted with $R°$; —$NO_2$; —CN; —$N_3$; —$(CH_2)_{0-4}N(R°)_2$; —$(CH_2)_{0-4}N(R°)C(O)R°$; —$N(R°)C(S)R°$; —$(CH_2)_{0-4}N(R°)C(O)NR°_2$; —$N(R°)C(S)NR°_2$; —$(CH_2)_{0-4}N(R°)C(O)OR°$; —$N(R°)N(R°)C(O)R°$; —$N(R°)N(R°)C(O)NR°_2$; —$N(R°)N(R°)C(O)OR°$; —$(CH_2)_{0-4}C(O)R°$; —C(S)R°; —$(CH_2)_{0-4}C(O)OR°$; —$(CH_2)_{0-4}C(O)SR°$; —$(CH_2)_{0-4}C(O)OSiR°_3$; —$(CH_2)_{0-4}OC(O)R°$; —$OC(O)(CH_2)_{0-4}SR$; —SC(S)SR'; —$(CH_2)_{0-4}SC(O)R°$; —$(CH_2)_{0-4}C(O)NR°_2$; —C(S)NR°_2; —C(S)SR'; —SC(S)SR'; —$(CH_2)_{0-4}OC(O)NR°_2$; —C(O)N(OR°)R°; —C(O)C(O)R°; —C(O)CH_2C(O)R°; —C(NOR°)R°; —$(CH_2)_{0-4}SSR°$; —$(CH_2)_{0-4}S(O)_2R°$; —$(CH_2)_{0-4}S(O)_2OR°$; —$(CH_2)_{0-4}OS(O)_2R°$; —$S(O)_2NR°_2$; —$(CH_2)_{0-4}S(O)R°$; —$N(R°)S(O)_2NR°_2$; —$N(R°)S(O)_2R°$; —$N(OR°)R°$; —C(NH)NR°_2; —P(O)_2R°; —P(O)R°_2; —P(O)(OR°)R°; —P(O)(OR°)_2; —OP(O)R°_2; —OP(O)(OR°)R°; —OP(O)(OR°)_2; —PR°_2; —P(OR°)R°; —P(OR°)_2; —OPR°_2; —OP(OR°)R°; —OP(OR°)_2; —SiR°_3; —OSiR°_3; —SeR°; —$(CH_2)_{0-4}SeSeR°$; —B(R°)_2, —B(OR°)_2, —$(C_{1-4}$ straight or branched)alkylene)O—N(R°_2; or —$(C_{1-4}$ straight or branched)alkylene)C(O)O—N(R°_2; wherein each R° may be substituted as defined below and is independently hydrogen, $C_{1-6}$ aliphatic, —$CH_2Ph$, —$O(CH_2)_{0-1}Ph$, —$CH_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of R°, taken together with their intervening atom(s), form a 3-12-membered saturated, partially unsaturated, or aryl mono- or bicyclic ring having 0-6 heteroatoms independently selected from nitrogen, oxygen, or sulfur, which may be substituted as defined below.

Suitable monovalent substituents on R° (or the ring formed by taking two independent occurrences of R° together with their intervening atoms), are independently halogen, —$(CH_2)_{0-2}R^●$, -(haloR^●), —$(CH_2)_{0-2}OH$, —$(CH_2)_{0-2}OR^●$, —$(CH_2)_{0-2}CH(OR^●)_2$; —$O(haloR^●)$, —CN, —$N_3$, —$(CH_2)_{0-2}C(O)R^●$, —$(CH_2)_{0-2}C(O)OH$, —$(CH_2)_{0-2}C(O)OR^●$, —$(CH_2)_{0-2}SR^●$, —$(CH_2)_{0-2}SH$, —$(CH_2)_{0-2}NH_2$, —$(CH_2)_{0-2}NHR^●$, —$(CH_2)_{0-2}NR^●_2$, —$NO_2$, —$SiR^●_3$, —$OSiR^●_3$, —$C(O)SR^●$, —$(C_{1-4}$ straight or branched alkylene)C(O)OR^●, or —SSR^● wherein each R^● is unsubstituted or where preceded by "halo" is substituted only with one or more halogens, and is independently selected from $C_{1-4}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, or sulfur. Suitable divalent substituents on a saturated carbon atom of R° include =O and =S.

Suitable divalent substituents on a suitable carbon atom of an "optionally substituted" group include the following: =O, =S, =NNR*_2, =NNHC(O)R*, =NNHC(O)OR*, =NNHS(O)_2R*, =NR*, =NOR*, —$O(C(R^*_2))_{2-3}O$—, or —$S(C(R^*_2))_{2-3}S$—, wherein each independent occurrence of R* is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —$O(CR^*_2)_{2-3}O$—, wherein each independent occurrence of R* is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R* include halogen, —$R^●$, -(haloR^●), —OH, —$OR^●$, —$O(haloR^●)$, —CN, —C(O)OH, —$C(O)OR^●$, —$NH_2$, —$NHR^●$, —$NR^●_2$, or —$NO_2$, wherein each R^● is unsubstituted or where preceded by "halo" is substituted only with one or more halogens, and is independently $C_{1-4}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, or sulfur.

Suitable substituents on a substitutable nitrogen of R† an "optionally substituted" group include —R†, —NR†_2, —C(O)R†, —C(O)OR†, —C(O)C(O)R†, —C(O)CH_2C(O)R†, —S(O)_2R†, —S(O)_2NR†_2, —C(S)NR†_2, —C(NH)NR†_2, or —N(R†)S(O)_2R†; wherein each R† is independently hydrogen, $C_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of R†, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of $R^\dagger$ are independently halogen, —R●, -(haloR●), —OH, —OR●, —O(haloR●), —CN, —C(O)OH, —C(O)OR●, —NH$_2$, —NHR●, —NR●$_2$, or —NO$_2$, wherein each R● is unsubstituted or where preceded by "halo" is substituted only with one or more halogens, and is independently $C_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

The term "chiral" is given its ordinary meaning in the art and refers to a molecule that is not superimposable with its mirror image, wherein the resulting non-superimposable mirror images are known as "enantiomers" and are labeled as either an (R) enantiomer or an (S) enantiomer. Typically, chiral molecules lack a plane of symmetry.

The term "achiral" is given its ordinary meaning in the art and refers to a molecule that is superimposable with its mirror image. Typically, achiral molecules possess a plane of symmetry.

The phrase "protecting group," as used herein, refers to temporary substituents which protect a potentially reactive functional group from undesired chemical transformations. Examples of such protecting groups include esters of carboxylic acids, silyl ethers of alcohols, and acetals and ketals of aldehydes and ketones, respectively. A "Si protecting group" is a protecting group comprising a Si atom, such as Si-trialkyl (e.g., trimethylsilyl, tributylsilyl, t-butyldimethylsilyl), Si-triaryl, Si-alkyl-diphenyl (e.g., t-butyldiphenylsilyl), or Si-aryl-dialkyl (e.g., Si-phenyldialkyl). Generally, a Si protecting group is attached to an oxygen atom. The field of protecting group chemistry has been reviewed (Greene, T. W.; Wuts, P. G. M. Protective Groups in Organic Synthesis, 2nd ed.; Wiley: New York, 1991). Such protecting groups (and associated protected moieties) are described in detail below.

Protected hydroxyl groups are well known in the art and include those described in detail in *Protecting Groups in Organic Synthesis*, T. W. Greene and P. G. M. Wuts, 3rd edition, John Wiley & Sons, 1999, the entirety of which is incorporated herein by reference. Examples of suitably protected hydroxyl groups further include, but are not limited to, esters, carbonates, sulfonates allyl ethers, ethers, silyl ethers, alkyl ethers, arylalkyl ethers, and alkoxyalkyl ethers. Examples of suitable esters include formates, acetates, proprionates, pentanoates, crotonates, and benzoates. Specific examples of suitable esters include formate, benzoyl formate, chloroacetate, trifluoroacetate, methoxyacetate, triphenylmethoxyacetate, p-chlorophenoxyacetate, 3-phenylpropionate, 4-oxopentanoate, 4,4-(ethylenedithio) pentanoate, pivaloate (trimethylacetate), crotonate, 4-methoxy-crotonate, benzoate, p-benylbenzoate, 2,4,6-trimethylbenzoate. Examples of suitable carbonates include 9-fluorenylmethyl, ethyl, 2,2,2-trichloroethyl, 2-(trimethylsilyl)ethyl, 2-(phenylsulfonyl)ethyl, vinyl, allyl, and p-nitrobenzyl carbonate. Examples of suitable silyl ethers include trimethylsilyl, triethylsilyl, t-butyldimethylsilyl, t-butyldiphenylsilyl, triisopropylsilyl ether, and other trialkylsilyl ethers. Examples of suitable alkyl ethers include methyl, benzyl, p-methoxybenzyl, 3,4-dimethoxybenzyl, trityl, t-butyl, and allyl ether, or derivatives thereof. Alkoxyalkyl ethers include acetals such as methoxymethyl, methylthiomethyl, (2-methoxyethoxy)methyl, benzyloxymethyl, beta-(trimethylsilyl)ethoxymethyl, and tetrahydropyran-2-yl ether. Examples of suitable arylalkyl ethers include benzyl, p-methoxybenzyl (MPM), 3,4-dimethoxybenzyl, O-nitrobenzyl, p-nitrobenzyl, p-halobenzyl, 2,6-dichlorobenzyl, p-cyanobenzyl, 2- and 4-picolyl ethers.

Protected amines are well known in the art and include those described in detail in Greene (1999). Suitable mono-protected amines further include, but are not limited to, aralkylamines, carbamates, allyl amines, amides, and the like. Examples of suitable mono-protected amino moieties include t-butyloxycarbonylamino (—NHBOC), ethyloxycarbonylamino, methyloxycarbonylamino, trichloroethyloxycarbonylamino, allyloxycarbonylamino (—NHAlloc), benzyloxycarbonylamino (—NHCBZ), allylamino, benzylamino (—NHBn), fluorenylmethylcarbonyl (—NHFmoc), formamido, acetamido, chloroacetamido, dichloroacetamido, trichloroacetamido, phenylacetamido, trifluoroacetamido, benzamido, t-butyldiphenylsilyl, and the like. Suitable di-protected amines include amines that are substituted with two substituents independently selected from those described above as mono-protected amines, and further include cyclic imides, such as phthalimide, maleimide, succinimide, and the like. Suitable di-protected amines also include pyrroles and the like, 2,2,5,5-tetramethyl-[1,2,5] azadisilolidine and the like, and azide.

Protected aldehydes are well known in the art and include those described in detail in Greene (1999). Suitable protected aldehydes further include, but are not limited to, acyclic acetals, cyclic acetals, hydrazones, imines, and the like. Examples of such groups include dimethyl acetal, diethyl acetal, diisopropyl acetal, dibenzyl acetal, bis(2-nitrobenzyl) acetal, 1,3-dioxanes, 1,3-dioxolanes, semicarbazones, and derivatives thereof.

Protected carboxylic acids are well known in the art and include those described in detail in Greene (1999). Suitable protected carboxylic acids further include, but are not limited to, optionally substituted $C_{1-6}$ aliphatic esters, optionally substituted aryl esters, silyl esters, activated esters, amides, hydrazides, and the like. Examples of such ester groups include methyl, ethyl, propyl, isopropyl, butyl, isobutyl, benzyl, and phenyl ester, wherein each group is optionally substituted. Additional suitable protected carboxylic acids include oxazolines and ortho esters.

Protected thiols are well known in the art and include those described in detail in Greene (1999). Suitable protected thiols further include, but are not limited to, disulfides, thioethers, silyl thioethers, thioesters, thiocarbonates, and thiocarbamates, and the like. Examples of such groups include, but are not limited to, alkyl thioethers, benzyl and substituted benzyl thioethers, triphenylmethyl thioethers, and trichloroethoxycarbonyl thioester, to name but a few.

Unless otherwise stated, structures depicted herein are also meant to include all isomeric (e.g., enantiomeric, diastereomeric, and geometric (or conformational)) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present compounds are within the scope of the invention.

Unless otherwise stated, all tautomeric forms of the compounds of the invention are within the scope of the invention.

Additionally, unless otherwise stated, structures depicted herein are also meant to include compounds that differ only in the presence of one or more isotopically enriched atoms. For example, compounds having the present structures except for the replacement of hydrogen by deuterium or tritium, or the replacement of a carbon by a $^{11}C$- or $^{13}C$- or $^{14}$C-enriched carbon are within the scope of this invention. Such compounds are useful, for example, as analytical tools or probes in biological assays.

As used herein and in the claims, the singular forms "a", "an", and "the" include the plural reference unless the context clearly indicates otherwise. Thus, for example, a reference to "a compound" includes a plurality of such compounds.

As used herein, the term "in vitro" refers to events that occur in an artificial environment, e.g., in a test tube or reaction vessel, in cell culture, etc., rather than within an organism (e.g., animal, plant, and/or microbe).

As used herein, the term "in vivo" refers to events that occur within an organism (e.g., animal, plant, and/or microbe).

The phrases "parenteral administration" and "administered parenterally" as used herein have their art-understood meaning referring to modes of administration other than enteral and topical administration, usually by injection, and include, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal, and intrasternal injection and infusion.

As used herein, the term "pharmaceutical composition" refers to an active agent, formulated together with one or more pharmaceutically acceptable carriers. In some embodiments, active agent is present in unit dose amount appropriate for administration in a therapeutic regimen that shows a statistically significant probability of achieving a predetermined therapeutic effect when administered to a relevant population. In some embodiments, pharmaceutical compositions may be specially formulated for administration in solid or liquid form, including those adapted for the following: oral administration, for example, drenches (aqueous or non-aqueous solutions or suspensions), tablets, e.g., those targeted for buccal, sublingual, and systemic absorption, boluses, powders, granules, pastes for application to the tongue; parenteral administration, for example, by subcutaneous, intramuscular, intravenous or epidural injection as, for example, a sterile solution or suspension, or sustained-release formulation; topical application, for example, as a cream, ointment, or a controlled-release patch or spray applied to the skin, lungs, or oral cavity; intravaginally or intrarectally, for example, as a pessary, cream, or foam; sublingually; ocularly; transdermally; or nasally, pulmonary, and to other mucosal surfaces.

As used herein, the phrase "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, the term "pharmaceutically acceptable carrier" means a pharmaceutically-acceptable material, composition or vehicle, such as a liquid or solid filler, diluent, excipient, or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; pH buffered solutions; polyesters, polycarbonates and/or polyanhydrides; and other non-toxic compatible substances employed in pharmaceutical formulations.

The term "pharmaceutically acceptable salt", as used herein, refers to salts of such compounds that are appropriate for use in pharmaceutical contexts, i.e., salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describes pharmaceutically acceptable salts in detail in J. Pharmaceutical Sciences, 66: 1-19 (1977). In some embodiments, pharmaceutically acceptable salt include, but are not limited to, nontoxic acid addition salts, which are salts of an amino group formed with inorganic acids such as hydrochloric acid, hydrobromic acid, phosphoric acid, sulfuric acid and perchloric acid or with organic acids such as acetic acid, maleic acid, tartaric acid, citric acid, succinic acid or malonic acid or by using other methods used in the art such as ion exchange. In some embodiments, pharmaceutically acceptable salts include, but are not limited to, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. In some embodiments, pharmaceutically acceptable salts include, when appropriate, nontoxic ammonium, quaternary ammonium, and amine cations formed using counterions such as halide, hydroxide, carboxylate, sulfate, As used herein, the term "protein" refers to a polypeptide (i.e., a string of at least two amino acids linked to one another by peptide bonds). In some embodiments, proteins include only naturally-occurring amino acids. In some embodiments, proteins include one or more non-naturally-occurring amino acids (e.g., moieties that form one or more peptide bonds with adjacent amino acids). In some embodiments, one or more residues in a protein chain contain a non-amino-acid moiety (e.g., a glycan, etc). In some embodiments, a protein includes more than one polypeptide chain, for example linked by one or more disulfide bonds or associated by other means. In some embodiments, proteins contain l-amino acids, d-amino acids, or both; in some embodiments, proteins contain one or more amino acid modifications or analogs known in the art. Useful modifications include, e.g., terminal acetylation, amidation, methylation, etc. The term "peptide" is generally used to refer to a polypeptide having a length of less than about 100 amino acids, less than about 50 amino acids, less than 20 amino acids, or less than 10 amino acids. In some embodiments, proteins are antibodies, antibody fragments, biologically active portions thereof, and/or characteristic portions thereof.

As used herein, the term "subject" or "test subject" refers to any organism to which a provided compound or composition is administered in accordance with the present invention e.g., for experimental, diagnostic, prophylactic, and/or therapeutic purposes. Typical subjects include animals (e.g., mammals such as mice, rats, rabbits, non-human primates, and humans; insects; worms; etc.). In some embodiments, a subject may be suffering from, and/or susceptible to a disease, disorder, and/or condition. In some embodiments, a subject is human.

As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and/or chemical phenomena.

An individual who is "suffering from" a disease, disorder, and/or condition has been diagnosed with and/or displays one or more symptoms of a disease, disorder, and/or condition.

An individual who is "susceptible to" a disease, disorder, and/or condition is one who has a higher risk of developing the disease, disorder, and/or condition than does a member of the general public. In some embodiments, an individual who is susceptible to a disease, disorder and/or condition may not have been diagnosed with the disease, disorder, and/or condition. In some embodiments, an individual who is susceptible to a disease, disorder, and/or condition may exhibit symptoms of the disease, disorder, and/or condition. In some embodiments, an individual who is susceptible to a disease, disorder, and/or condition may not exhibit symptoms of the disease, disorder, and/or condition. In some embodiments, an individual who is susceptible to a disease, disorder, and/or condition will develop the disease, disorder, and/or condition. In some embodiments, an individual who is susceptible to a disease, disorder, and/or condition will not develop the disease, disorder, and/or condition.

The phrases "systemic administration," "administered systemically," "peripheral administration," and "administered peripherally" as used herein have their art-understood meaning referring to administration of a compound or composition such that it enters the recipient's system.

As used herein, the phrase "therapeutic agent" refers to any agent that, when administered to a subject, has a therapeutic effect and/or elicits a desired biological and/or pharmacological effect. In some embodiments, a therapeutic agent is any substance that can be used to alleviate, ameliorate, relieve, inhibit, prevent, delay onset of, reduce severity of, and/or reduce incidence of one or more symptoms or features of a disease, disorder, and/or condition.

As used herein, the term "therapeutically effective amount" means an amount of a substance (e.g., a therapeutic agent, composition, and/or formulation) that elicits a desired biological response when administered as part of a therapeutic regimen. In some embodiments, a therapeutically effective amount of a substance is an amount that is sufficient, when administered to a subject suffering from or susceptible to a disease, disorder, and/or condition, to treat, diagnose, prevent, and/or delay the onset of the disease, disorder, and/or condition. As will be appreciated by those of ordinary skill in this art, the effective amount of a substance may vary depending on such factors as the desired biological endpoint, the substance to be delivered, the target cell or tissue, etc. For example, the effective amount of compound in a formulation to treat a disease, disorder, and/or condition is the amount that alleviates, ameliorates, relieves, inhibits, prevents, delays onset of, reduces severity of and/or reduces incidence of one or more symptoms or features of the disease, disorder, and/or condition. In some embodiments, a therapeutically effective amount is administered in a single dose; in some embodiments, multiple unit doses are required to deliver a therapeutically effective amount.

As used herein, the term "treat," "treatment," or "treating" refers to any method used to partially or completely alleviate, ameliorate, relieve, inhibit, prevent, delay onset of, reduce severity of, and/or reduce incidence of one or more symptoms or features of a disease, disorder, and/or condition. Treatment may be administered to a subject who does not exhibit signs of a disease, disorder, and/or condition. In some embodiments, treatment may be administered to a subject who exhibits only early signs of the disease, disorder, and/or condition, for example for the purpose of decreasing the risk of developing pathology associated with the disease, disorder, and/or condition.

The expression "unit dose" as used herein refers to an amount administered as a single dose and/or in a physically discrete unit of a pharmaceutical composition. In many embodiments, a unit dose contains a predetermined quantity of an active agent. In some embodiments, a unit dose contains an entire single dose of the agent. In some embodiments, more than one unit dose is administered to achieve a total single dose. In some embodiments, administration of multiple unit doses is required, or expected to be required, in order to achieve an intended effect. A unit dose may be, for example, a volume of liquid (e.g., an acceptable carrier) containing a predetermined quantity of one or more therapeutic agents, a predetermined amount of one or more therapeutic agents in solid form, a sustained release formulation or drug delivery device containing a predetermined amount of one or more therapeutic agents, etc. It will be appreciated that a unit dose may be present in a formulation that includes any of a variety of components in addition to the therapeutic agent(s). For example, acceptable carriers (e.g., pharmaceutically acceptable carriers), diluents, stabilizers, buffers, preservatives, etc., may be included as described infra. It will be appreciated by those skilled in the art, in many embodiments, a total appropriate daily dosage of a particular therapeutic agent may comprise a portion, or a plurality, of unit doses, and may be decided, for example, by the attending physician within the scope of sound medical judgment. In some embodiments, the specific effective dose level for any particular subject or organism may depend upon a variety of factors including the disorder being treated and the severity of the disorder; activity of specific active compound employed; specific composition employed; age, body weight, general health, sex and diet of the subject; time of administration, and rate of excretion of the specific active compound employed; duration of the treatment; drugs and/or additional therapies used in combination or coincidental with specific compound(s) employed, and like factors well known in the medical arts.

As used herein, the terms "effective amount" and "effective dose" refer to any amount or dose of a compound or composition that is sufficient to fulfill its intended purpose(s), i.e., a desired biological or medicinal response in a tissue or subject at an acceptable benefit/risk ratio. The relevant intended purpose may be objective (i.e., measurable by some test or marker) or subjective (i.e., subject gives an indication of or feels an effect). In some embodiments, a therapeutically effective amount is an amount that, when administered to a population of subjects that meet certain clinical criteria for a disease or disorder (for example, as determined by symptoms manifested, disease progression/stage, genetic profile, etc.), a statistically significant therapeutic response is obtained among the population. A therapeutically effective amount is commonly administered in a dosing regimen that may comprise multiple unit doses. For any particular pharmaceutical agent, a therapeutically effective amount (and/or an appropriate unit dose within an effective dosing regimen) may vary, for example, depending on route of administration, on combination with other pharmaceutical agents. In some embodiments, the specific therapeutically effective amount (and/or unit dose) for any particular patient may depend upon a variety of factors including the disorder being treated and the severity of the disorder; the activity of the specific pharmaceutical agent employed; the specific composition employed; the age, body weight, general health, sex and diet of the patient; the time of administration, route of administration, and/or rate of excretion or metabolism of the specific pharmaceutical agent employed; the duration of the treatment; and like factors as is well known in the medical arts. Those of ordinary skill in the art will appreciate that in some embodiments of the invention, a unit dosage may be considered to contain an effective amount if it contains an amount appropriate for administration in the context of a dosage regimen correlated with a positive outcome.

3. Description of Certain Embodiments of the Invention

In some embodiments, the present invention provides a pharmaceutical composition of a compound of formula I:

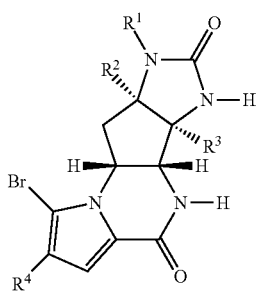

I or a pharmaceutically acceptable salt thereof, wherein each variable is independently as described in classes and subclasses herein, both singly and in combination.

In some embodiments, the present invention provides a method for treating a blood cancer in a subject in need thereof, comprising administering to the subject a therapeutically effective amount of a compound of formula I:

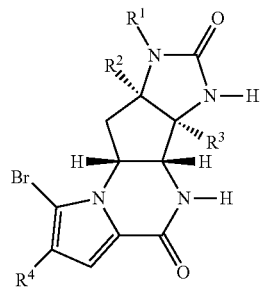

I or a pharmaceutically acceptable salt thereof, wherein each variable is independently as described in classes and subclasses herein, both singly and in combination. In some embodiments, a subject is suffering from a blood cancer. In some embodiments, a subject is susceptible to a blood cancer.

In some embodiments, the present invention provides a method for inhibiting growth of blood cancer cells. In some embodiments, the present invention provides a method for inhibiting growth of blood cancer cells, comprising administering a compound of formula I:

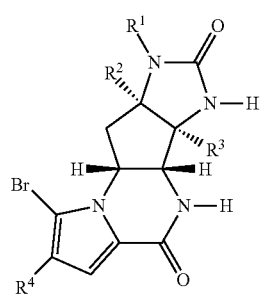

I or a pharmaceutically acceptable salt thereof, wherein each variable is independently as described in classes and subclasses herein, both singly and in combination.

In some embodiments, the present invention provides a method for inhibiting proliferation of blood cancer cells. In some embodiments, the present invention provides a method for inhibiting proliferation of blood cancer cells, comprising administering a compound of formula I:

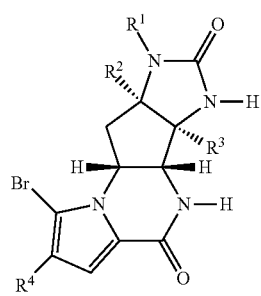

I or a pharmaceutically acceptable salt thereof, wherein each variable is independently as described in classes and subclasses herein, both singly and in combination.

In some embodiments, the present invention provides a method for promoting apoptosis of blood cancer cells. In some embodiments, the present invention provides a method for promoting apoptosis of blood cancer cells, comprising administering a compound of formula I:

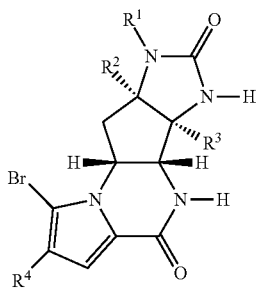

I or a pharmaceutically acceptable salt thereof, wherein each variable is independently as described in classes and subclasses herein, both singly and in combination.

In some embodiments, the present invention provides a method for arresting cell cycle in blood cancer cells. In some embodiments, the present invention provides a method for arresting cell cycle in blood cancer cells, comprising administering a compound of formula I:

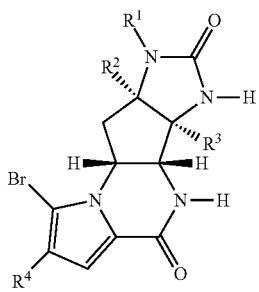

I or a pharmaceutically acceptable salt thereof, wherein each variable is independently as described in classes and subclasses herein, both singly and in combination.

In some embodiments, the present invention provides a method for inducing arrest in G2/M phase in blood cancer cells. In some embodiments, the present invention provides a method for inducing arrest in G2/M phase in blood cancer cells, comprising administering a compound of formula I:

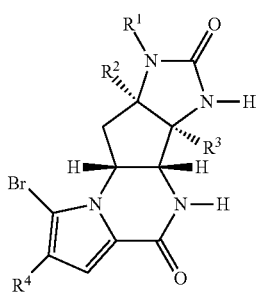

I or a pharmaceutically acceptable salt thereof, wherein each variable is independently as described in classes and subclasses herein, both singly and in combination.

As defined generally above, $R^1$ is —H or —CH$_3$. In some embodiments, $R^1$ is —H. In some embodiments, $R^1$ is —CH$_3$.

As defined generally above, $R^2$ is —OH or —OCH$_3$. In some embodiments, $R^2$ is —OH. In some embodiments, $R^2$ is —OCH$_3$.

As defined generally above, $R^3$ is —H or —OH. In some embodiments, $R^3$ is —H. In some embodiments, $R^3$ is —OH.

In some embodiments, $R^4$ is —H, or —Br when $R^1$ is —CH$_3$. In some embodiments, $R^4$ is —H. In some embodiments, $R^4$ is —Br when $R^1$ is —CH$_3$.

In some embodiments, a compound of formula I has an IC$_{50}$ value of about 0.02 µM or less for a blood cancer cell line. In some embodiments, a compound of formula I has an IC$_{50}$ value of about 0.03 µM or less for a blood cancer cell line. In some embodiments, a compound of formula I has an IC$_{50}$ value of about 0.04 µM or less for a blood cancer cell line. In some embodiments, a compound of formula I has an IC$_{50}$ value of about 0.05 µM or less for a blood cancer cell line. In some embodiments, a compound of formula I has an IC$_{50}$ value of about 0.06 µM or less for a blood cancer cell line. In some embodiments, a compound of formula I has an IC$_{50}$ value of about 0.07 µM or less for a blood cancer cell line. In some embodiments, a compound of formula I has an IC$_{50}$ value of about 0.08 µM or less for a blood cancer cell line. In some embodiments, a compound of formula I has an IC$_{50}$ value of about 0.09 µM or less for a blood cancer cell line. In some embodiments, a compound of formula I has an IC$_{50}$ value of about 0.1 µM or less for a blood cancer cell line. In some embodiments, a compound of formula I has an IC$_{50}$ value of about 0.15 µM or less for a blood cancer cell line. In some embodiments, a compound of formula I has an IC$_{50}$ value of about 0.2 µM or less for a blood cancer cell line. In some embodiments, a compound of formula I has an IC$_{50}$ value of about 0.3 µM or less for a blood cancer cell line. In some embodiments, a compound of formula I has an IC$_{50}$ value of about 0.4 µM or less for a blood cancer cell line. In some embodiments, a compound of formula I has an IC$_{50}$ value of about 0.5 µM or less for a blood cancer cell line. In some embodiments, a compound of formula I has an IC$_{50}$ value of about 0.6 µM or less for a blood cancer cell line. In some embodiments, a compound of formula I has an IC$_{50}$ value of about 0.7 µM or less for a blood cancer cell line. In some embodiments, a compound of formula I has an IC$_{50}$ value of about 0.8 µM or less for a blood cancer cell line. In some embodiments, a compound of formula I has an IC$_{50}$ value of about 0.9 µM or less for a blood cancer cell line. In some embodiments, a compound of formula I has an IC$_{50}$ value of about 1 µM or less for a blood cancer cell line. In some embodiments, a compound of formula I has an IC$_{50}$ value of about 2 µM or less for a blood cancer cell line. In some embodiments, a compound of formula I has an IC$_{50}$ value of about 3 µM or less for a blood cancer cell line. In some embodiments, a compound of formula I has an IC$_{50}$ value of about 4 µM or less for a blood cancer cell line. In some embodiments, a compound of formula I has an IC$_{50}$ value of about 5 µM or less for a blood cancer cell line. In some embodiments, a compound of formula I has an IC$_{50}$ value of about 6 µM or less for a blood cancer cell line. In some embodiments, a compound of formula I has an IC$_{50}$ value of about 7 µM or less for a blood cancer cell line. In some embodiments, a compound of formula I has an IC$_{50}$ value of about 8 µM or less for a blood cancer cell line. In some embodiments, a compound of formula I has an IC$_{50}$ value of about 9 µM or less for a blood cancer cell line. In some embodiments, a compound of formula I has an IC$_{50}$ value of about 10 µM or less for a blood cancer cell line.

In some embodiments, an IC$_{50}$ value is measured at about 48-hour exposure to a compound of formula I (48-hr IC$_{50}$).

In some embodiments, $IC_{50}$ is determined by 3-(4,5-dimethylthiazol-2-yl)-5-(3-carboxymethoxyphenyl)-2-(4-sulfophenyl)-2H-tetrazolium) (MTS). In some embodiments, $IC_{50}$ is determined by sulforhodamine B (SRB).

In some embodiments, a blood cancer cell line is U-937. In some embodiments, a blood cancer cell line is CEM. In some embodiments, a blood cancer cell line is Jurkat. In some embodiments, a blood cancer cell line is Daudi. In some embodiments, a blood cancer cell line is HL-60. In some embodiments, a blood cancer cell line is CA46.

In some embodiments, a compound of formula I has a lower $IC_{50}$ for one or more of blood cancer cell lines, e.g., U-937, CEM, Jurkat, Daudi, HL-60 and CA46, than for one or more of non-blood cancer cell lines, e.g., Hela, A549 and BT549. In some embodiments, a compound of formula I has a lower $IC_{50}$ for each of the U-937, CEM, Jurkat, Daudi, HL-60 and CA46 cell lines than for each of Hela, A549 and BT549.

In some embodiments, a compound of formula I has a lower $IC_{50}$ for blood cancer cells than normal cells. In some embodiments, a compound of formula I has a lower $IC_{50}$ for blood cancer cells than for immortalized lung fibroblast (e.g., IMR 90 cell line).

In some embodiments, a compound of formula I has low hemolytic activity. In some embodiments, a compound of formula I has no hemolytic activity at 333 μM, as measured using the method described for FIG. 2. In some embodiments, a compound of formula I has no hemolytic activity at about 300 μM. In some embodiments, a compound of formula I has no hemolytic activity at about 250 μM. In some embodiments, a compound of formula I has no hemolytic activity at about 200 μM. In some embodiments, a compound of formula I has no hemolytic activity at about 150 μM. In some embodiments, a compound of formula I has no hemolytic activity at about 100 μM In some embodiments, a compound of formula I has no hemolytic activity at about 50 μM. In some embodiments, a compound of formula I show no or low hemolytic activity, e.g., <10% blood cell hemolysis, at a concentration 10,000 fold of its $IC_{50}$ for blood cancer cells, e.g., U-937, CEM, Jurkat, Daudi, HL-60 or CA46 cell line. In some embodiments, a compound of formula I show no or low hemolytic activity at a concentration 5,000 fold of its $IC_{50}$ for blood cancer cells. In some embodiments, a compound of formula I show no or low hemolytic activity at a concentration 1,000 fold of its $IC_{50}$ for blood cancer cells. In some embodiments, a compound of formula I show no or low hemolytic activity at a concentration 500 fold of its $IC_{50}$ for blood cancer cells. In some embodiments, hemolysis is measured two hours after compound administration.

Blood cancers, or hematologic cancers, include cancers of the blood, bone marrow and lymph nodes. In some embodiments, blood cancers include leukemia, lymphoma and myeloma.

In some embodiments, a blood cancer is leukemia. Leukemia includes lymphocytic leukemia and myelogenous leukemia (also known as myeloid or myelocytic leukemia). In some embodiments, a blood cancer is lymphocytic leukemia. In some embodiments, a blood cancer is myelogenous leukemia. In some embodiments, leukemia is acute. In some embodiments, leukemia is chronic. In some embodiments, a blood cancer is acute lymphoblastic leukemia (ALL). In some embodiments, a blood cancer is acute myelogenous leukemia (AML). In some embodiments, a blood cancer is chronic lymphocytic leukemia (CLL). In some embodiments, a blood cancer is chronic myelogenous leukemia (CML). In some embodiments, a blood cancer is acute monocytic leukemia (AMoL). In some embodiments, a blood cancer is acute T-cell leukemia. In some embodiments, a blood cancer is acute promyelocytic leukemia.

In some embodiments, a blood cancer is lymphoma. Lymphoma includes Hodgkin lymphoma and non-Hodgkin lymphoma. In some embodiments, a blood cancer is Hodgkin lymphoma. In some embodiments, a blood cancer is non-Hodgkin lymphoma. In some embodiments, a blood cancer is Burkitt's lymphoma.

In some embodiments, a blood cancer is myeloma.

In some embodiments, a blood cancer is selected from acute lymphoblastic leukemia "ALL", acute lymphoblastic B-cell leukemia, acute lymphoblastic T-cell leukemia, acute myeloblastic leukemia AML", acute promyelocytic leukemia "APL", acute monoblastic leukemia, acute erythroleukemic leukemia, acute megakaryoblastic leukemia, acute myelomonocytic leukemia, acute nonlymphocyctic leukemia, acute undifferentiated leukemia, chronic myelocytic leukemia "CML", chronic lymphocytic leukemia "CLL", hairy cell leukemia, multiple myeloma, acute and chronic leukemias, lymphoblastic, myelogenous, lymphocytic and myelocytic leukemias. Lymphomas, Hodgkin's disease, non-Hodgkin's Lymphoma, Multiple myeloma, Waldenström's macroglobulinemia, Heavy chain disease, and Polycythemia vera.

In some embodiments, a compound of formula I is

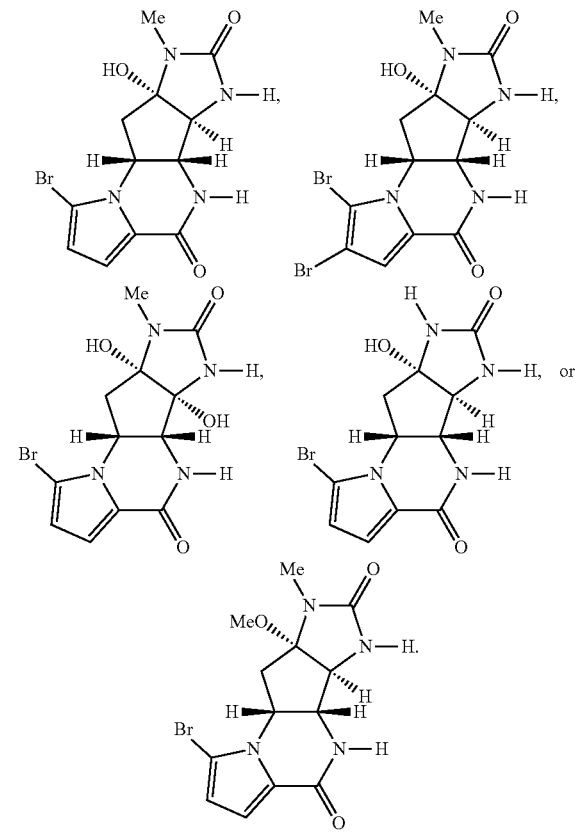

In some embodiments, a compound of formula I is

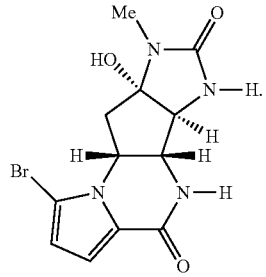

In some embodiments, a compound of formula I is

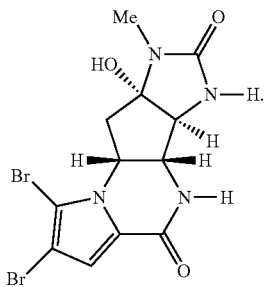

In some embodiments, a compound of formula I is

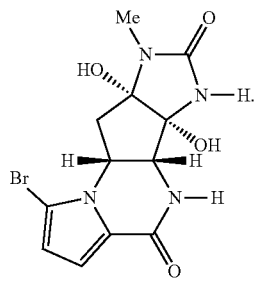

In some embodiments, a compound of formula I is

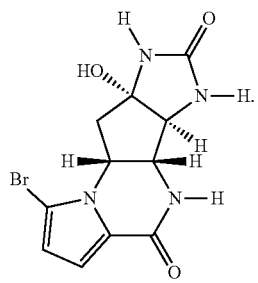

In some embodiments, a compound of formula I is

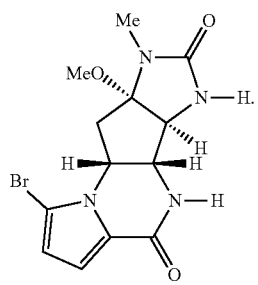

In some embodiments, a provided compound of formula I or its pharmaceutically acceptable salt thereof is administered in a composition. In some embodiments, a provided compound of formula I or its pharmaceutically acceptable salt thereof is administered in a pharmaceutical composition. In some embodiments, a composition in a provided method is suitable for veterinary or human administration.

A composition can be in any form that allows for the composition to be administered to a subject. For example, a composition can be in the form of a solid, liquid or gas (aerosol). Typical routes of administration include, without limitation, oral, topical, parenteral, sublingual, rectal, vaginal, ocular, intra-tumor, and intranasal. Parenteral administration includes subcutaneous injections, intravenous, intramuscular, intrasternal injection or infusion techniques. In some embodiments, a provided compound is administered parenterally. In some embodiments, a provided compound is administered parenterally. In some embodiments, a provided composition is administered intravenously. In some embodiments, a provided composition is administered intravenously.

Pharmaceutical compositions can be formulated so as to allow a provided compound to be bioavailable upon administration of the composition to a patient. Compositions can take the form of one or more dosage units, where for example, a tablet can be a single dosage unit, a vial may contain a single dose for intravenous administration, and a container of a provided compound in aerosol form can hold a plurality of dosage units.

Materials used in preparing the pharmaceutical compositions can be non-toxic in the amounts used. It will be evident to those of ordinary skill in the art that the optimal dosage of the active ingredient(s) in the pharmaceutical composition will depend on a variety of factors. Relevant factors include, without limitation, the type of animal (e.g., human), the particular form of a provided compound or composition, the manner of administration, and the composition employed.

A pharmaceutically acceptable carrier or vehicle can be particulate, so that the compositions are, for example, in tablet or powder form. The carrier(s) can be liquid, with the compositions being, for example, an oral syrup or injectable liquid. In addition, the carrier(s) can be gaseous or particulate, so as to provide an aerosol composition useful in, e.g., inhalatory administration. When intended for oral administration, a composition is preferably in solid or liquid form, where semi-solid, semi-liquid, suspension and gel forms are included within the forms considered herein as either solid or liquid.

As a solid composition for oral administration, a composition can be formulated into a powder, granule, compressed tablet, pill, capsule, chewing gum, wafer or the like form. Such a solid composition typically contains one or more inert diluents. In addition, one or more of the following can be present: binders such as carboxymethylcellulose, ethyl cellulose, microcrystalline cellulose, or gelatin; excipients such as starch, lactose or dextrins, disintegrating agents such as alginic acid, sodium alginate, Primogel, corn starch and the like; lubricants such as magnesium stearate or Sterotex; glidants such as colloidal silicon dioxide; sweetening agents such as sucrose or saccharin, a flavoring agent such as peppermint, methyl salicylate or orange flavoring, and a coloring agent.

When a composition is in the form of a capsule, e.g., a gelatin capsule, it can contain, in addition to materials of the above type, a liquid carrier such as polyethylene glycol, cyclodextrin or a fatty oil.

A composition can be in the form of a liquid, e.g., an elixir, syrup, solution, emulsion or suspension. The liquid can be useful for oral administration or for delivery by injection. When intended for oral administration, a composition can comprise one or more of a sweetening agent, preservatives, dye/colorant and flavor enhancer. In a composition for administration by injection, one or more of a surfactant, preservative, wetting agent, dispersing agent, suspending agent, buffer, stabilizer and isotonic agent can also be included.

Liquid compositions, whether they are solutions, suspensions or other like form, can also include one or more of the following: sterile diluents such as water for injection, saline solution, preferably physiological saline, Ringer's solution, isotonic sodium chloride, fixed oils such as synthetic mono or digylcerides which can serve as the solvent or suspending medium, polyethylene glycols, glycerin, cyclodextrin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. A parenteral composition can be enclosed in ampoule, a disposable syringe or a multiple-dose vial made of glass, plastic or other material. Physiological saline is an exemplary adjuvant. An injectable composition is preferably sterile.

The amount of a provided compound that is effective in the treatment of a particular disorder or condition will depend on the nature of the disorder or condition, and can be determined by standard clinical techniques. In addition, in vitro or in vivo assays can optionally be employed to help identify optimal dosage ranges. The precise dose to be employed in the compositions will also depend on the route of administration, and the seriousness of the disease or disorder, and should be decided according to the judgment of the practitioner and each patient's circumstances.

Provided compositions comprise an effective amount of a provided compound such that a suitable dosage will be obtained. In some embodiments, this amount is at least about 0.01% of a provided compound by weight of the composition. When intended for oral administration, this amount can be varied to range from about 0.1% to about 80% by weight of the composition. In one aspect, oral compositions can comprise from about 4% to about 50% of a provided compound by weight of the composition. In yet another aspect, a provided composition is prepared so that a parenteral dosage unit contains from about 0.01% to about 2% by weight of a provided compound or composition.

For intravenous administration, a provided composition can comprise from about 0.01 to about 100 mg of a provided compound per kg of a subject's body weight. In one aspect, the composition can include from about 1 to about 100 mg of a provided compound per kg of a subject's body weight. In another aspect, the amount administered will be in the range from about 0.1 to about 25 mg/kg of body weight of a provided compound.

Generally, dosage of a provided compound administered to a patient is typically about 0.001 mg/kg to about 2000 mg/kg of a subject body weight. In one aspect, a dosage administered to a patient is between about 0.01 mg/kg to about 10 mg/kg of a subject's body weight, in another aspect, a dosage administered to a subject is between about 0.1 mg/kg and about 250 mg/kg of a subject's body weight, in yet another aspect, a dosage administered to a patient is between about 0.1 mg/kg and about 20 mg/kg of a subject's body weight, in yet another aspect a dosage administered is between about 0.1 mg/kg to about 10 mg/kg of a subject's body weight, and in yet another aspect, a dosage administered is between about 1 mg/kg to about 10 mg/kg of a subject's body weight. In some embodiments, a daily dosage might range from about 1 µg/kg to 100 mg/kg or more, depending on the factors mentioned above. An exemplary dosage to be administered to a patient is in the range of about 0.1 to about 10 mg/kg of patient weight.

A provided compound can be administered by any convenient route, for example by infusion or bolus injection, by absorption through epithelial or mucocutaneous linings (e.g., oral mucosa, rectal and intestinal mucosa, etc.). Administration can be systemic or local. Various delivery systems are known, e.g., encapsulation in liposomes, microparticles, microcapsules, capsules, etc., and can be used to administer a provided compound or composition. In certain embodiments, more than one provided compound or composition is administered to a patient.

In some embodiments, it is desirable to administer one or more provided compounds or compositions locally to the area in need of treatment. This can be achieved, for example, and not by way of limitation, by local infusion during surgery; topical application, e.g., in conjunction with a wound dressing after surgery; by injection; by means of a catheter; by means of a suppository; or by means of an implant, the implant being of a porous, non-porous, or gelatinous material, including membranes, such as sialastic membranes, or fibers. In one embodiment, administration can be by direct injection at the site (or former site) of a cancer, tumor or neoplastic or pre-neoplastic tissue. In another embodiment, administration can be by direct injection at the site (or former site) of a manifestation of an autoimmune disease.

In certain embodiments, it can be desirable to introduce one or more provided compounds or compositions into the central nervous system by any suitable route, including intraventricular and intrathecal injection. Intraventricular injection can be facilitated by an intraventricular catheter, for example, attached to a reservoir, such as an Ommaya reservoir.

Pulmonary administration can also be employed, e.g., by use of an inhaler or nebulizer, and formulation with an aerosolizing agent, or via perfusion in a fluorocarbon or synthetic pulmonary surfactant.

In some embodiments, a provided compound or compositions can be delivered in a controlled release system, such as but not limited to, a pump or various polymeric materials can be used. In yet another embodiment, a controlled-release system can be placed in proximity of a target of a provided compound or compositions, e.g., the brain, thus requiring only a fraction of the systemic dose (see, e.g., Goodson, in Medical Applications of Controlled Release, supra, vol. 2, pp. 115-138 (1984)). Other controlled-release systems discussed in the review by Langer (Science 249:1527-1533 (1990)) can be used.

In some embodiments, a carrier is a diluent, adjuvant or excipient, with which a provided compound is administered. Such pharmaceutical carriers can be liquids, such as water and oils, including those of petroleum, animal, vegetable or synthetic origin, such as peanut oil, soybean oil, mineral oil, sesame oil and the like. Carriers can be saline, gum acacia, gelatin, starch paste, talc, keratin, colloidal silica, urea, and the like. In addition, auxiliary, stabilizing, thickening, lubricating and coloring agents can be used. In one embodiment, when administered to a patient, provided compounds or compositions and pharmaceutically acceptable carriers are sterile. Water is an exemplary carrier when a provided compound is administered intravenously. Saline solutions and aqueous dextrose and glycerol solutions can also be employed as liquid carriers, particularly for injectable solutions. Suitable pharmaceutical carriers also include excipients such as starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The present compositions, if desired, can also contain minor amounts of wetting or emulsifying agents, or pH buffering agents.

Provided compositions can take the form of solutions, suspensions, emulsion, tablets, pills, pellets, capsules, capsules containing liquids, powders, sustained-release formulations, suppositories, emulsions, aerosols, sprays, suspensions, or any other form suitable for use. Other examples of suitable pharmaceutical carriers are described in "Remington's Pharmaceutical Sciences" by E. W. Martin.

In some embodiments, a provided compound or composition is formulated in accordance with routine procedures as a pharmaceutical composition adapted for intravenous administration to a subject particularly a human being. In some embodiments, carriers or vehicles for intravenous administration are sterile isotonic aqueous buffer solutions. Where necessary, a provided composition can also include a solubilizing agent. Compositions for intravenous administration can optionally comprise a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where a provided compound is to be administered by infusion, it can be dispensed, for example, with an infusion bottle containing sterile pharmaceutical grade water or saline. Where a provided compound is administered by injection, an ampoule of sterile water for injection or saline can be provided so that the ingredients can be mixed prior to administration.

Compositions for oral delivery can be in the form of tablets, lozenges, aqueous or oily suspensions, granules, powders, emulsions, capsules, syrups, or elixirs, for example. Orally administered compositions can contain one or more optionally agents, for example, sweetening agents such as fructose, aspartame or saccharin; flavoring agents such as peppermint, oil of wintergreen, or cherry; coloring agents; and preserving agents, to provide a pharmaceutically palatable preparation. In some embodiments, where in tablet or pill form, a provided composition can be coated to delay disintegration and absorption in the gastrointestinal tract thereby providing a sustained action over an extended period of time. Selectively permeable membranes surrounding an osmotically active driving compound are also suitable for orally administered compounds. For example, in these later platforms, fluid from the environment surrounding a capsule is imbibed by a driving compound, which swells to displace an agent or agent composition through an aperture. In some embodiments, a delivery platform can provide an essentially zero order delivery profile as opposed to the spiked profiles of immediate release formulations. A time-delay material such as glycerol monostearate or glycerol stearate can also be used.

A provided composition can be intended for topical administration, in which case the carrier may be in the form of a solution, emulsion, ointment or gel base. If intended for transdermal administration, the composition can be in the form of a transdermal patch or an iontophoresis device. Topical formulations can comprise a concentration of a provided compound of from about 0.05% to about 50% w/v (weight per unit volume of composition), in another aspect, from 0.1% to 10% w/v.

A provided composition can be intended for rectal administration, in the form, e.g., of a suppository which will melt in the rectum and release a provided compound.

A provided composition can include various materials that modify the physical form of a solid or liquid dosage unit. For example, a provided composition can include materials that form a coating shell around the active ingredients. The materials that form the coating shell are typically inert, and can be selected from, for example, sugar, shellac, and other enteric coating agents. Alternatively, the active ingredients can be encased in a gelatin capsule.

The compositions can consist of gaseous dosage units, e.g., it can be in the form of an aerosol. In some embodiments, an aerosol is used to denote a variety of systems ranging from those of colloidal nature to systems consisting of pressurized packages. Delivery can be by a liquefied or compressed gas or by a suitable pump system that dispenses the active ingredients.

Whether in solid, liquid or gaseous form, a provided composition can include a pharmacological agent used in the treatment of cancer, an autoimmune disease or an infectious disease.

A provided pharmaceutical composition may be in the form of a sterile injectable preparation, such as a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, such as a solution in 1,3-butane-diol or prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

Formulations may be packaged in unit-dose or multi-dose containers, for example sealed ampoules and vials, and may be stored in a freeze-dried (lyophilized) condition requiring only the addition of the sterile liquid carrier, for example water, for injection immediately prior to use. Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof, of the active ingredient.

In some embodiments, the present invention provides veterinary compositions comprising at least one active ingredient as above defined together with a veterinary carrier therefore. Veterinary carriers are materials useful for the purpose of administering the composition and may be solid, liquid or gaseous materials which are otherwise inert or acceptable in the veterinary art and are compatible with the active ingredient. These veterinary compositions may be administered parenterally, orally or by any other desired route.

A provided compound of the invention may be combined in a pharmaceutical combination formulation, or dosing regimen as combination therapy, with a second compound having therapeutic properties. A second compound of the pharmaceutical combination formulation or dosing regimen preferably has complementary activities to a provided compound of the combination such that they do not adversely affect each other.

In some embodiments, a second compound is a chemotherapeutic agent, cytotoxic agent, cytokine, growth inhibitory agent, anti-hormonal, a drug for an autoimmune disease, a drug for an infectious disease, and/or cardioprotectant. Such molecules are suitably present in combination in amounts that are effective for the purpose intended.

A combination therapy may be administered as a simultaneous or sequential regimen. When administered sequentially, the combination may be administered in two or more administrations. The combined administration includes co-administration, using separate formulations or a single pharmaceutical formulation, and consecutive administration in either order, wherein preferably there is a time period while both (or all) active agents simultaneously exert their biological activities.

Suitable dosages for co-administered agents are those presently used and may be lowered due to the combined action (synergy) of the newly identified agent and other chemotherapeutic agents or treatments.

A provided combination therapy may provide "synergy" and prove "synergistic", i.e. the effect achieved when the active ingredients used together is greater than the sum of the effects that results from using the compounds separately. A synergistic effect may be attained when the active ingredients are: (1) co-formulated and administered or delivered simultaneously in a combined, unit dosage formulation; (2) delivered by alternation or in parallel as separate formulations; or (3) by some other regimen. When delivered in alternation therapy, a synergistic effect may be attained when the compounds are administered or delivered sequentially, e.g. by different injections in separate syringes. In general, during alternation therapy, an effective dosage of each active ingredient is administered sequentially, i.e. serially, whereas in combination therapy, effective dosages of two or more active ingredients are administered together.

In some embodiments, the present invention provides methods of treating cancer. In some embodiments, the present invention provides a method of treating cancer in a subject suffering therefrom, comprising administering to the subject a therapeutically effective amount of a provided compound. In some embodiments, a provided compound is a compound of formula I or its pharmaceutically acceptable salt thereof.

In some embodiments, a provided compound is administered prior to, concurrently with, or subsequent to, a chemotherapeutic agent. In some embodiments, a chemotherapeutic agent is that with which treatment of the cancer has not been found to be refractory. In some embodiments, a chemotherapeutic agent is that with which the treatment of cancer has been found to be refractory. In some embodiments, a provided compound is administered to a patient that has also undergone surgery as treatment for the cancer.

In some embodiments, an additional method of treatment is radiation therapy. In some embodiments, a provided compound or composition is administered prior to, concurrently with or subsequent to radiation.

In some embodiments, a provided compound or composition is administered concurrently with a chemotherapeutic agent or with radiation therapy. In some embodiments, a chemotherapeutic agent or radiation therapy is administered prior or subsequent to administration of a provided compound or composition. In some embodiments, a chemotherapeutic agent or radiation therapy is administered concurrently with administration of a provided compound or composition. In some embodiments, a provided compound or composition is administered at least one hour, five hours, 12 hours, a day, a week, a month, or several months (e.g., up to three months), prior or subsequent to administration of a provided compound or composition.

A chemotherapeutic agent can be administered over a series of sessions. Any one or a combination of the chemotherapeutic agents can be administered. Exemplary chemotherapy drugs are widely known in the art, including but not limited to tubulin-binding drugs, kinase inhibitors, alkylating agents, DNA topoisomerase inhibitors, anti-folates, pyrimidine analogs, purine analogs, DNA antimetabolites, hormonal therapies, retinoids/deltoids, photodynamic therapies, cytokines, angiogenesis inhibitors, histone modifying enzyme inhibitors, and antimitotic agents. Examples are extensively described in the art, including but not limited to those in PCT Application Publication No. WO2010/025272.

In some embodiments, a provided compound or composition is administered prior to, concurrently with or subsequent to another polypeptide or protein. In some embodiments, a polypeptide or protein is a recombinant polypeptide or protein. Exemplary polypeptides or proteins include but are not limited to cytokines, interferon alfa-2b, interleukin 2, filgrastim, rasburicase, secretin, asparaginase *Erwinia chrysanthemi*, and ziv-aflibercept. In some embodiments, a polypeptide or protein comprises an antibody or a fragment of an antibody. In some embodiments, a polypeptide or protein is an antibody or a fragment of an antibody. Examples include but are not limited to rituximab, trastuzumab, tositumomab, alemtuzumab, bevacizumab, cetuximab, panitumumab, ofatumumab, denosumab, ipilimumab, pertuzumab. In some embodiments, a polypeptide or protein is chemically modified. In some embodiments, a polypeptide or protein is conjugated to a drug. In some embodiments, an antibody or an antibody fragment is conjugated to a payload drug, forming an antibody-drug conjugate. In some embodiments, a payload drug is cytotoxic. Exemplary antibody-drug conjugates include but are not limited to gemtuzumab ozogamicin, brentuximab vedotin, and ado-trastuzumab emtansine. In some embodiments, a cancer treatment comprises the use of a vaccine. Exemplary vaccines for cancer treatment are well known in the art, for example but not limited to sipuleucel-T.

With respect to radiation, any radiation therapy protocol can be used depending upon the type of cancer to be treated. For example, but not by way of limitation, X-ray radiation can be administered; in some embodiments, high-energy megavoltage (radiation of greater that 1 MeV energy) can be used for deep tumors, and electron beam and orthovoltage x-ray radiation can be used for skin cancers. Gamma-ray emitting radioisotopes, such as radioactive isotopes of radium, cobalt and other elements, can also be administered.

In some embodiments, methods of treatment of cancer with a provided compound or composition are provided as an alternative to chemotherapy or radiation therapy where the chemotherapy or the radiation therapy has proven or can prove too toxic, e.g., results in unacceptable or unbearable side effects, for a subject being treated. A subject being treated can, optionally, be treated with another cancer treatment such as surgery, radiation therapy or chemotherapy, depending on which treatment is found to be acceptable or bearable.

In some embodiments, a provided compound or composition can be used in an in vitro or ex vivo fashion, such as for the treatment of certain cancers, including, but not limited to leukemias and lymphomas. In some embodiments, such a treatment involves autologous stem cell transplants. In some embodiments, this can involve a multi-step process in which a subject's autologous hematopoietic stem cells are harvested and purged of all cancer cells, a subject's remaining bone-marrow cell population is then eradicated via the administration of a high dose of a provided compound or composition with or without accompanying high dose radiation therapy, and the stem cell graft is infused back into the animal. Supportive care is then provided while bone marrow function is restored and a subject recovers.

In some embodiments, the present invention provides copper-mediated cross-coupling reaction between thioester and an organostannane reagent. In some embodiments, an organostannane reagent is a stannyl triazone reagent. In some embodiments, an organostannane reagent is stannyl urea. In some embodiments, an organostannane reagent is stannyl guanidine. In some embodiments, the present invention provides copper-mediated cross-coupling reaction between thioester and a stannyl triazone reagent. In some embodiments, the metal-mediated cross-coupling reaction does not comprise the use of Pd or its salt. In some embodiments, the reaction is carried out with catalytic amount of palladium. In some embodiments, the reaction is carried out without palladium. In some embodiments, the reaction is mediated by a Cu(I) salt. In some embodiments, a Cu(I) salt is Cu(I) diphenylphosphinate (CuDPP). In some embodiments, a Cu(I) salt is Cu(I)-thiophene-2-carboxylate (CuTC). In some embodiments, a stannyl triazone reagent contains cyclohexyl groups. In some embodiments, a stannyl triazone reagent contains cyclohexyl groups as auxiliary ligands to tin suppress undesired alkyl transfer. In some embodiments, a thioester has the formula of $R^5C(O)$—$SR^9$, an organostannane reagent has the structure of $(R)_3SnC(R)_2N(R^6)$—$C(X)$—$N(R^7)(R^8)$, wherein:

each of $R^5$, $R^6$, $R^7$, $R^8$, $R^9$ and R is independently hydrogen or an optionally substituted group selected from $C_{1-20}$ aliphatic, $C_{1-20}$ heteroalkyl, phenyl, a 3-7 membered saturated or partially unsaturated carbocyclic ring, an 8-14 membered bicyclic or polycyclic saturated, partially unsaturated or aryl ring, a 5-6 membered monocyclic heteroaryl ring having 1-4 heteroatoms independently selected from nitrogen, oxygen, or sulfur, a 3-7 membered saturated or partially unsaturated heterocyclic ring having 1-3 heteroatoms independently selected from nitrogen, oxygen, or sulfur, a 7-14 membered bicyclic or polycyclic saturated or partially unsaturated heterocyclic ring having 1-5 heteroatoms independently selected from nitrogen, oxygen, or sulfur, or an 8-14 membered bicyclic or polycyclic heteroaryl ring having 1-5 heteroatoms independently selected from nitrogen, oxygen, or sulfur; or:

two or more $R^5$, $R^6$, $R^7$, $R^8$, $R^9$ and R groups are optionally taken together with their intervening atoms to form an optionally substituted 3-14 membered, monocyclic or polycyclic, saturated, partially unsaturated, or aryl ring having, in addition to the intervening atoms, 0-4 heteroatoms independently selected from nitrogen, oxygen, or sulfur; and X is O or NR.

In some embodiments, X is O. In some embodiments, X is NR, wherein R is as defined above and described herein.

In some embodiments, $R^9$ is p-$C_6H_4$Me. In some embodiments, an organostannane reagent is $(Cy)_3SnCH_2N(R^6)$—$C(X)$—$N(R^7)(R^8)$, wherein each of $R^6$, $R^7$ and $R^8$ is independently as defined above and described herein. In some embodiments, a product is $R^5C(O)C(R)_2N(R^6)$—$C(X)$—$N(R^7)(R^8)$. In some embodiments, a product is $R^5C(O)CH_2N(R^6)$—$C(X)$—$N(R^7)(R^8)$. In some embodiments, $R^9$ is p-$C_6H_4$Me, an organostannane reagent is $(Cy)_3SnCH_2N(R^6)$—$C(X)$—$N(R^7)(R^8)$, and a product is $R^5C(O)CH_2N(R^6)$—$C(X)$—$N(R^7)(R^8)$. In some embodiments, $R^5C(O)CH_2N(R^6)$—$C(X)$—$N(R^7)(R^8)$ is converted to

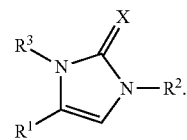

Conditions

Suitable conditions for performing provided methods or preparing provided compounds may employ one or more solvents. In certain embodiments, one or more organic solvents are used. Examples of such organic solvents include, but are not limited to, hydrocarbons such as benzene, toluene, and pentane, halogenated hydrocarbons such as dichloromethane and chloroform, or polar aprotic solvents, such as ethereal solvents including ether, tetrahydrofuran (THF), or dioxanes, or protic solvents, such as alcohols, or mixtures thereof. In some embodiments, a solvent is substituted hydrocarbons. In some embodiments, a solvent is $MeNO_2$. In some embodiments, a solvent is $EtNO_2$. In certain embodiments, one or more solvents are deuterated. In some embodiments, a single solvent is used. In certain embodiments, a solvent is benzene. In certain embodiments, a solvent is ether. In some embodiments, a solvent comprises a nitrile group. In some embodiments, a solvent is acetonitrile.

In some embodiments, mixtures of two or more solvents are used, and in some cases may be preferred to a single solvent. In certain embodiments, the solvent mixture is a mixture of an ethereal solvent and a hydrocarbon. Exemplary such mixtures include, for instance, an ether/benzene mixture. Solvent mixtures may be comprised of equal volumes of each solvent or may contain one solvent in excess of the other solvent or solvents. In certain embodiments wherein a solvent mixture is comprised of two solvents, the solvents may be present in a ratio of about 20:1, about 10:1, about 9:1, about 8:1, about 7:1, about 6:1, about 5:1, about 4:1, about 3:1, about 2:1, or about 1:1. In certain embodiments wherein a solvent mixture comprises an ethereal solvent and a hydrocarbon, the solvents may be present in a ratio of about 20:1, about 10:1, about 9:1, about 8:1, about 7:1, about 6:1, about 5:1, about 4:1, about 3:1, about 2:1, or about 1:1 ethereal solvent:hydrocarbon. In certain embodiments, the solvent mixture comprises a mixture of ether and benzene in a ratio of about 5:1. One of skill in the art would appreciate that other solvent mixtures and/or ratios are contemplated herein, that the selection of such other solvent mixtures and/or ratios will depend on the solubility of species present in the reaction (e.g., substrates, additives, etc.), and that experimentation required to optimized the solvent mixture and/or ratio would be routine in the art and not undue.

In some embodiments, a solvent is water. In some embodiments, a solvent is water. In some embodiments, a mixture of water with one or more other solvents is used.

Suitable conditions, in some embodiments, employ ambient temperatures. In some embodiments, a suitable temperature is about 15° C., about 20° C., about 25° C., or about 30° C. In some embodiments, a suitable temperature is from about 15° C. to about 25° C. In certain embodiments, a suitable temperature is about 20° C., 21° C., 22° C., 23° C., 24° C., or 25° C.

In certain embodiments, a provided method is performed at elevated temperature. In some embodiments, a suitable temperature is from about 25° C. to about 110° C. In certain embodiments, a suitable temperature is from about 40° C. to about 100° C., from about 50° C. to about 100° C., from about 60° C. to about 100° C., from about 70° C. to about 100° C., from about 80° C. to about 100° C., or from about 90° C. to about 100° C. In some embodiments, a suitable temperature is about 80° C. In some embodiments, a suitable temperature is about 30° C. In some embodiments, a suitable temperature is about 40° C. In some embodiments, a suitable temperature is about 50° C. In some embodiments, a suitable temperature is about 60° C. In some embodiments, a suitable temperature is about 70° C. In some embodiments, a suitable temperature is about 80° C. In some embodiments, a suitable temperature is about 90° C. In some embodiments, a suitable temperature is about 100° C. In some embodiments, a suitable temperature is about 110° C.

In certain embodiments, a provided method is performed at temperature lower than ambient temperatures. In some embodiments, a suitable temperature is from about −100° C. to about 10° C. In certain embodiments, a suitable temperature is from about −80° C. to about 0° C. In certain embodiments, a suitable temperature is from about −70° C. to about 10° C. In certain embodiments, a suitable temperature is from about −60° C. to about 10° C. In certain embodiments, a suitable temperature is from about −50° C. to about 10° C. In certain embodiments, a suitable temperature is from about −40° C. to about 10° C. In certain embodiments, a suitable temperature is or from about −30° C. to about 10° C. In some embodiments, a suitable temperature is below 0° C. In some embodiments, a suitable temperature is about −100° C. In some embodiments, a suitable temperature is about −90° C. In some embodiments, a suitable temperature is about −80° C. In some embodiments, a suitable temperature is about −70° C. In some embodiments, a suitable temperature is about −60° C. In some embodiments, a suitable temperature is about −50° C. In some embodiments, a suitable temperature is about −40° C. In some embodiments, a suitable temperature is about −30° C. In some embodiments, a suitable temperature is about −20° C. In some embodiments, a suitable temperature is about −10° C. In some embodiments, a suitable temperature is about 0° C. In some embodiments, a suitable temperature is about 10° C.

In some embodiments, a provided method is performed at different temperatures. In some embodiments, temperature changes in a provided method. In some embodiments, a provided method involves temperature increase from a lower suitable temperature to a higher suitable temperature. In some embodiments, a provided method comprises temperature increase from about −80° C., about −70° C., about −60° C., about −50° C., about −40° C., about −30° C., about −20° C., about −10° C., and about 0° C. to about 0° C., about 10° C., about 20° C., ambient temperature, about 22° C., about 25° C., about 30° C., about 40° C., about 50° C., about 60° C., about 70° C., about 80° C., about 90° C., about 100° C. and about 110° C. In some embodiments, a provided method comprises temperature increase from about −30° C. to 22° C. In some embodiments, a provided method comprises temperature decrease from a higher suitable temperature to a lower suitable temperature. In some embodiments, a provided method comprises temperature increase from about 110° C., about 100° C., about 90° C., about 80° C., about 70° C., about 60° C., about 50° C., about 40° C., about 30° C., about 25° C., about 22° C., ambient temperature, about 20° C., about 10° C., and about 0° C. to about 0° C., about −10° C., about −20° C., about −30° C., about −40° C., about −50° C., about −60° C., about −70° C., about −80° C., about −90° C., and about −100° C.

Suitable conditions typically involve reaction times of about 1 minute to about one or more days. In some embodiments, the reaction time ranges from about 0.5 hour to about 20 hours. In some embodiments, the reaction time ranges from about 0.5 hour to about 15 hours. In some embodiments, the reaction time ranges from about 1.0 hour to about 12 hours. In some embodiments, the reaction time ranges from about 1 hour to about 10 hours. In some embodiments, the reaction time ranges from about 1 hour to about 8 hours. In some embodiments, the reaction time ranges from about 1 hour to about 6 hours. In some embodiments, the reaction time ranges from about 1 hour to about 4 hours. In some embodiments, the reaction time ranges from about 1 hour to about 2 hours. In some embodiments, the reaction time ranges from about 2 hours to about 8 hours. In some embodiments, the reaction time ranges from about 2 hours to about 4 hours. In some embodiments, the reaction time ranges from about 2 hours to about 3 hours. In certain embodiments, the reaction time is about 1, 2, 3, 4, 5, 6, 7, 8, 9, 10, 11, or 12, 24, 48, 96 or 120 hours. In certain embodiments, the reaction time is about 1 hour. In certain embodiments, the reaction time is about 2 hours. In certain embodiments, the reaction time is about 3 hours. In certain embodiments, the reaction time is about 4 hours. In certain embodiments, the reaction time is about 5 hours. In certain embodiments, the reaction time is about 6 hours. In some embodiments, the reaction time is about 12 hours. In some embodiments, the reaction time is about 24 hours. In some embodiments, the reaction time is about 48 hours. In some embodiments, the reaction time is about 96 hours. In some embodiments, the reaction time is about 120 hours. In certain embodiments, the reaction time is less than about 1 hour. In certain embodiments, the reaction time is about 5, 10, 15, 20, 25, 30, 35, 40, 45, 50, or 55 minutes. In some embodiments, the reaction time is about 5 minutes. In some embodiments, the reaction time is about 10 minutes. In some embodiments, the reaction time is about 15 minutes. In some embodiments, the reaction time is about 20 minutes. In some embodiments, the reaction time is about 25 minutes. In some embodiments, the reaction time is about 30 minutes. In some embodiments, the reaction time is about 35 minutes. In some embodiments, the reaction time is about 40 minutes. In some embodiments, the reaction time is about 100 minutes. In some embodiments, the reaction time is about 110 minutes. In some embodiments, the reaction time is about 200 minutes. In some embodiments, the reaction time is about 300 minutes. In some embodiments, the reaction time is about 400 minutes.

In some embodiments, a provided method requires an amount of a compound which promotes a reaction, such that the loading is from about 0.001 mol % to about 20 mol % of the compound relative to substrate. In certain embodiments, the compound is used in an amount of between about 0.001 mol % to about 10 mol %. In certain embodiments, the compound is used in an amount of between about 0.001 mol % to about 6 mol %. In certain embodiments, the compound is used in an amount of between about 0.001 mol % to about 5 mol %. In certain embodiments, the compound is used in an amount of between about 0.001 mol % to about 4 mol %. In certain embodiments, the compound is used in an amount of between about 0.001 mol % to about 3 mol %. In certain embodiments, the compound is used in an amount of between about 0.001 mol % to about 1 mol %. In certain embodiments, the compound is used in an amount of between about 0.001 mol % to about 0.5 mol %. In certain embodiments, the compound is used in an amount of between about 0.001 mol % to about 0.2 mol %. In certain embodiments, the compound is used in an amount of about 0.001 mol %, 0.002 mol %, 0.005 mol %, 0.01 mol %, 0.02 mol %, 0.03 mol %, 0.04 mol %, 0.05 mol %, 0.1 mol %, 0.2 mol %, 0.5 mol %, 1 mol %, 2 mol %, 3 mol %, 4 mol %, 5 mol %, 6 mol %, 7 mol %, 8 mol %, 9 mol %, or 10 mol %. In some embodiments, the compound is used in an amount of about 0.0002% mol. In some embodiments, the compound is used in an amount of about 0.01% mol. In some embodiments, the compound is used in an amount of about 3% mol.

In some embodiments, a method of the present invention requires an amount of solvent such that the concentration of the reaction is between about 0.01 M and about 1 M. In some embodiments, the concentration of the reaction is between about 0.01 M and about 0.5 M. In some embodiments, the concentration of the reaction is between about 0.01 M and about 0.1 M. In some embodiments, the concentration of the reaction is between about 0.01 M and about 0.05 M. In some embodiments, the concentration of the reaction is about 0.01 M. In some embodiments, the concentration of the reaction is about 0.02 M. In some embodiments, the concentration of the reaction is about 0.03 M. In some embodiments, the concentration of the reaction is about 0.04 M. In some embodiments, the concentration of the reaction is about 0.05 M. In some embodiments, the concentration of the reaction is about 0.1 M. In some embodiments, the concentration of the reaction is about 0.3 M.

In some embodiments, a method of the present invention is performed at ambient pressure. In some embodiments, a method of the present invention is performed at reduced pressure. In some embodiments, a method of the present invention is performed at a pressure of less than about 20 torr. In some embodiments, a method of the present invention is performed at a pressure of less than about 15 torr. In some embodiments, a method of the present invention is performed at a pressure of less than about 10 torr. In some embodiments, a method of the present invention is performed at a pressure of about 9, 8, 7, 6, 5, 4, 3, 2, or 1 torr. In certain embodiments, a method of the present invention is performed at a pressure of about 7 torr. In certain embodiments, a method of the present invention is performed at a pressure of about 1 torr.

In some embodiments, a method of the present invention is performed at increased pressure. In some embodiments, a method of the present invention is performed at greater than about 1 atm. In some embodiments, a method of the present invention is performed at greater than about 2 atm. In some embodiments, a method of the present invention is performed at greater than about 3 atm. In some embodiments, a method of the present invention is performed at greater than about 5 atm. In some embodiments, a method of the present invention is performed at greater than about 10 atm. In some embodiments, a method of the present invention is performed at about 2 atm. In some embodiments, a method of the present invention is performed at about 3 atm. In some embodiments, a method of the present invention is performed at about 5 atm. In some embodiments, a method of the present invention is performed at about 10 atm.

In some embodiments, a provided method provides chemoselectivity. In some embodiments, a desired product is produced in greater than about 50%, 55%, 60%, 65%, 70%, 75%, 80%, 85%, 90%, 91%, 92%, 93%, 94%, 95%, 96%, 97% 98%, 99% or 99.5% selectivity.

In some embodiments, a provided method provides stereoselectivity. In some embodiments, a desired stereoisomer is produced in greater than about 50%, 55%, 60%, 65%, 70%, 75%, 80%, 85%, 90%, 91%, 92%, 93%, 94%, 95%, 96%, 97% 98%, 99% or 99.5% selectivity. In some embodiments, a provided method provides diastereoselectivity. In some embodiments, a provided method provides diastereoselectivity. In some embodiments, a desired diastereomer is produced in greater than about 50%, 55%, 60%, 65%, 70%, 75%, 80%, 85%, 90%, 91%, 92%, 93%, 94%, 95%, 96%, 97% 98%, 99% or 99.5% selectivity. In some embodiments, a provided method provides enantioselectivity. In some embodiments, a desired enantiomer is produced in greater than about 50%, 55%, 60%, 65%, 70%, 75%, 80%, 85%, 90%, 91%, 92%, 93%, 94%, 95%, 96%, 97% 98%, 99% or 99.5% selectivity.

It will be appreciated that, in certain embodiments, each variable recited is as defined above and described in embodiments, herein, both singly and in combination.

EXEMPLIFICATION

The present invention recognizes, among other things, that there is a continuing demand for compounds, compositions and methods for treating various diseases, including blood cancers. In some embodiments, the present invention provides such compounds, compositions and methods. In some embodiments, the present invention provides methods for treating blood cancers. Exemplary but non-limiting examples are described herein.

The foregoing has been a description of certain non-limiting embodiments of the invention. Accordingly, it is to be understood that the embodiments of the invention herein described are merely illustrative of the application of the principles of the invention. Reference herein to details of the illustrated embodiments is not intended to limit the scope of the claims.

The agelastatins are a family of cytotoxic pyrrole-imidazole alkaloids exhibiting a unique tetracyclic framework with four contiguous stereogenic centers on the carbocyclic C-ring.

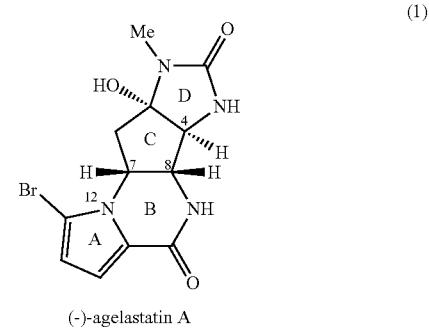

(-)-agelastatin A (1)

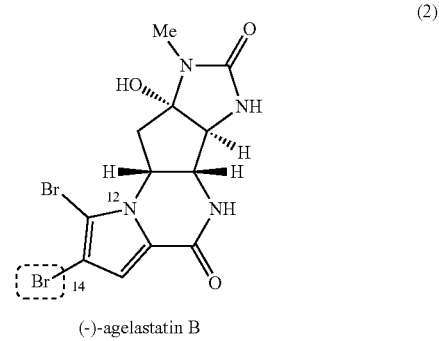

(-)-agelastatin B (2)

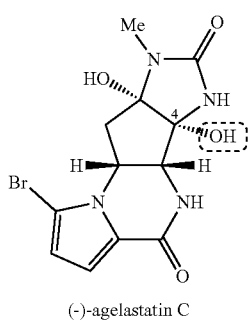

(-)-agelastatin C (3)

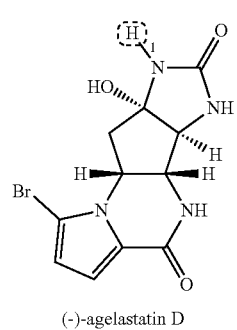

(-)-agelastatin D (4)

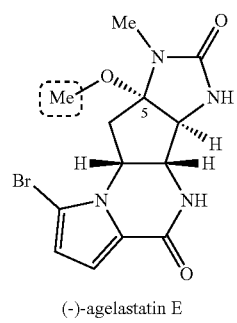

(-)-agelastatin E (5)

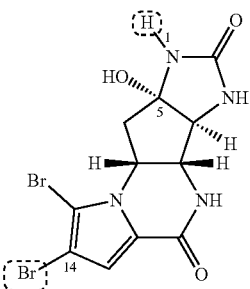

(-)-agelastatin F (6)

The Structures of (-)-agelastatins A-F (1-6)

Herein, among other things, Applicants provide a detailed account of enantioselective total synthesis of certain exemplary compounds and the development of a key methodology for the synthesis of imidazol-2-one and 2-aminoimidazoles. Applicants also provided exemplary data demonstrating that provided compounds are particularly useful for treating blood cancers.

One retrosynthetic analysis of (-)-agelastatin A (1) is shown in Scheme 1. Ionization of the C5-hydroxyl of 1 followed by the disconnection of the strategic C4-C8 bond revealed the N-acyliminium ion 8. The N-acyliminium ion 8 could be derived from the corresponding C8-hydroxyl derivative, pre-agelastatin A (9), which would be accessed from the tricycle 10 through a late-stage C8-oxidation. This analysis was distinct from prior biosynthetic hypotheses in that: a) C4 served as a nucleophile adding to an electrophilic C8; b) the C-ring formation occurred post B-ring formation; c) stereochemical information at C7 of pre-agelastatin A was used to set the C4-, C5-, and C8-stereocenters of (-)-agelastatin A (1).

Scheme 1. Retrosynthetic analysis of (-)-agelastatin A (1).

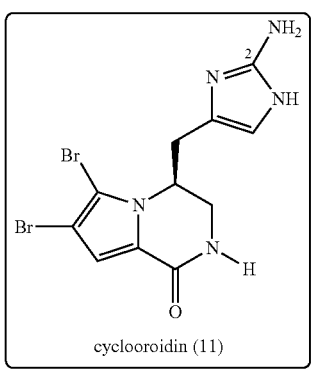

cyclooroidin (11)

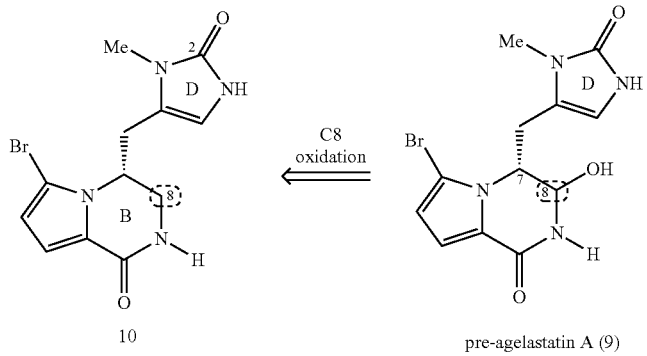

10      pre-agelastatin A (9)

Keto-triazones could be used for the formation of the C4-C8 bond (Scheme 2). C-ring could be generated via nucleophilic attack of a C4-enol to a C8 electrophilic derivative of ketone 12 after C8-oxidation. In this approach, the AB-bicyclic structure of ketone 12 could be introduced via an intramolecular conjugate addition of N12 in mane 13 followed by an oxidative aromatization. L-proline could be used to introduce the C7 stereochemistry of intermediate 12.

Scheme 2. An early approach toward (-)-agelastatin A (1).

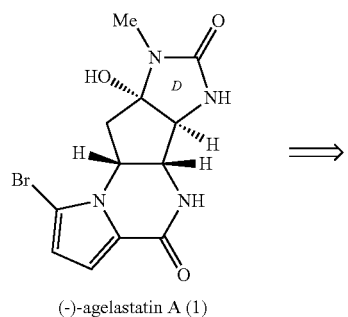

(-)-agelastatin A (1)

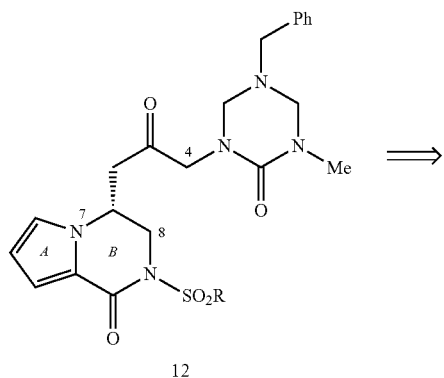

12

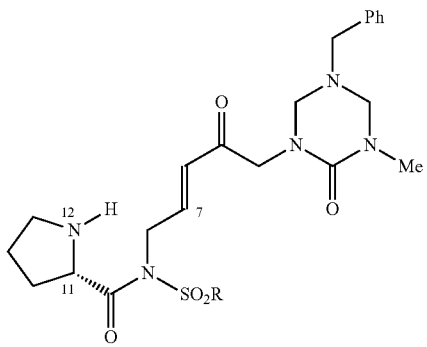

13

The above synthetic approach to 1 commenced with a Mitsunobu reaction involving L-proline derivative 14 and allylic alcohol 15 followed by Dess-Martin periodinane (DMP) C5-oxidation to give enone 16 in 73% yield over two steps (Scheme 3). Exposure of carbamate 16 to trifluoroacetic acid resulted in the unveiling of the N12 and spontaneous intramolecular conjugate addition to afford pyrrolidine 17 in 85% yield as a 13:1 mixture of diastereomers at C7 (major diastereomer shown). Without the intention to be limited by theory, this modest level of diastereoselection hinted at possible further refinement of this approach for asymmetric synthesis of lactam 18 based on the C11-stereochemistry of enone 16. For the key C-ring cyclization, sequential treatment of ketone 17 with DMP gave the corresponding pyrrole derivative (42% yield), not wishing to be limited by theory, possibly through oxidation of the C11-enol tautomer, followed by N9-desulfonylation to afford the desired lactam 18 in 84% yield.

Scheme 3. Synthesis of key bicycle 18 and attempted oxidation-cyclization.

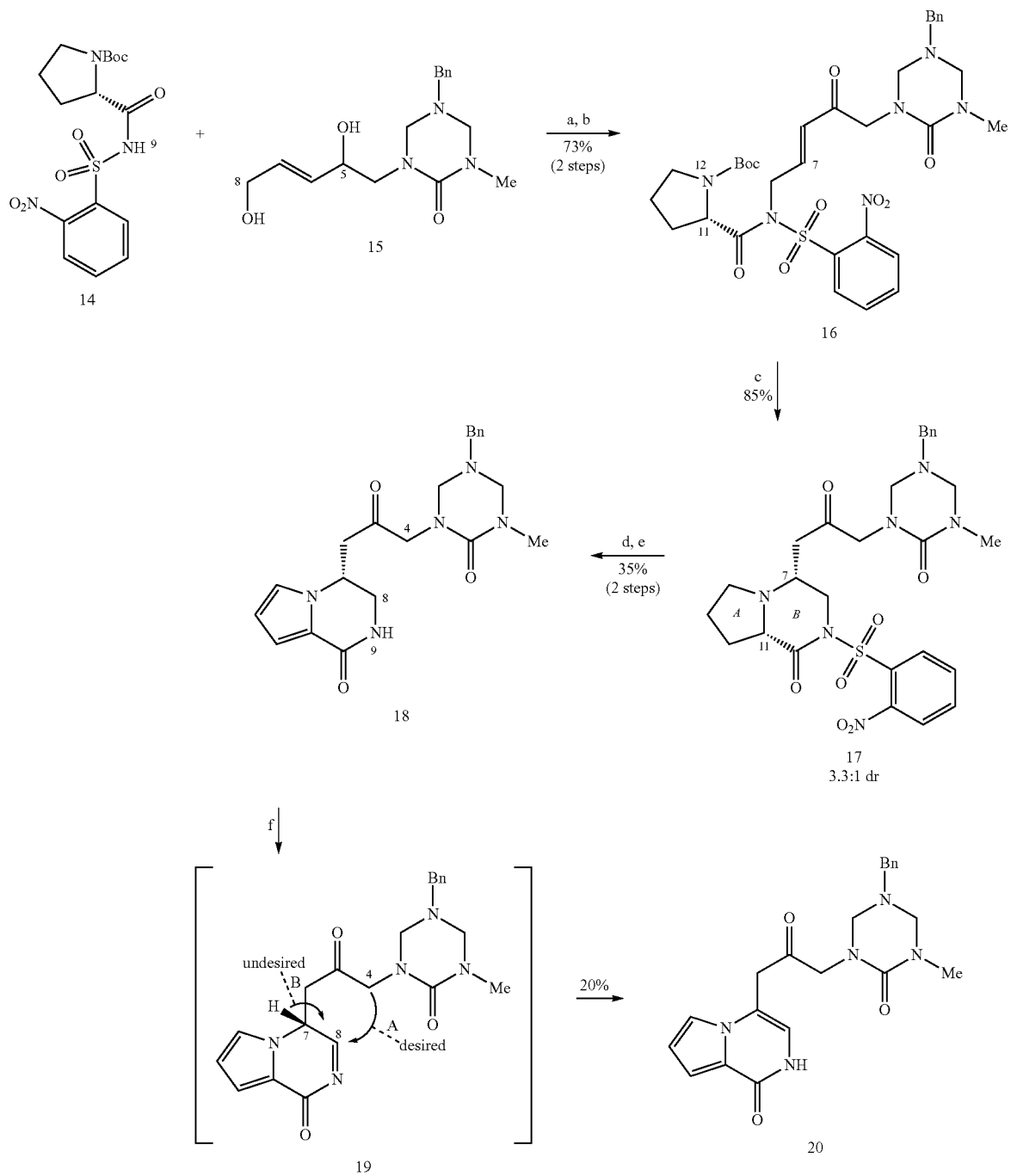

Conditions: (a) DEAD, PPh₃, THF, 0 → 23° C., 79%; (b) DMP, CH₂Cl₂, 23° C., 93%; (c) TFA, CH₂Cl₂, 0° C., 85%; (d) DMP, CH₂Cl₂, 23° C., 42%; (e) PhSH, KOH, MeCN, 0° C., 84%; (f) N-t-butylbenzenesulfinimidoyl chloride, DBU, CH₂Cl₂, -78 → 23° C., 20%.

The oxidation of C8 to generate the necessary electrophile 19 (Scheme 3) proved difficult. α-Oxidation of amides is a challenging process. After examining a wide range of conditions, it was found that treatment of lactam 18 with N-t-butylbenzenesulfinimidoyl chloride in the presence of DBU gave rise to the enamide 20 in 20% yield along with 20% recovery of lactam 18. Indeed, when ketone 18 was dissolved in methanol-d₄ in the presence of DBU, complete deuterium incorporation at C4 occurred in less than a minute. Without the intention to be limited by theory, the more facile oxidation of the lactam 18 at positions other than C8, and a favorable tautomerization of acylimine 19 to the highly stable bicycle 20 (Scheme 3, arrow B) seemed to prevent the desired formation of the C4-C8 bond (Scheme 3, arrow A).

First-Generation Total Synthesis

Another approach to the desired bicyclic hemiaminal ether 21 was the partial reduction of C8-carbonyl of imide 23 (Scheme 4). For the formation of the key C4-C8 bond, the imidazolone heterocycle could be used as a nucleophile.

Scheme 4. Two strategies for the introduction of the C8-hemiaminal ether 21.

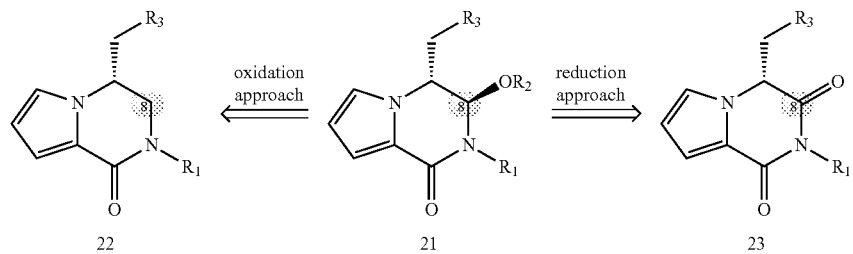

Treatment of the known methyl ester 24 with benzylamine and methoxyamine resulted in the formation of imides 25a and 25b in 86% and 48% yield, respectively (Scheme 5). Each of these imides was obtained as a racemate, without the intention to be limited by theory, reflecting the facile deprotonation of the acidic C7 proton. Imides 25a and 25b were readily reduced with L-selectride and subsequent treatment with p-toluenesulfonic acid yielded hemiaminal ethers 26a and 26b in 55% and 46% yield (two steps), respectively. The addition of an α-lithiated triazone inter mediate, prepared by treatment of triazone 27 with s-butyllithium, to methyl ester (±)-26a gave ketone (±)-28 in 70% yield. Exposure of triazone (±)-28 to methanolic hydrogen chloride solution led to spontaneous condensative cyclization to form the imidazolone D-ring in 66% yield (Scheme 5).

Imidazolone (±)-29 was then treated with scandium trifluoromethanesulfonate (Sc(OTf)$_3$) to induce the acyliminium ion formation and subsequent introduction of the C-ring; however, the C8-hydroxy hemiaminal product (±)-30, isolated in 36% yield, and pyrrolopyrazinone 31 (<5% yield) were the only observed products (Scheme 6). When hemiaminal (±)-30 was exposed to dichloromethane and trifluoroacetic acid (TFA) mixture, pyrrolopyrazinone 31 was obtained in quantitative yield. While not wishing to be limited by theory, Applicants note that these results suggested that the acyliminium ion intermediate was transiently formed, but was not effectively trapped by the C4 nucleophile. In an attempt to minimize tautomerization of the acyliminium ion under milder, acid-free reaction conditions, a sulfoxide group was planned to be introduced at the C8 position. Thus, imidazolone (±)-29 was treated with ethanethiol in trifluoroacetic acid and dichloromethane mixture Scheme 5. Synthesis of imidazolone (±)-29.

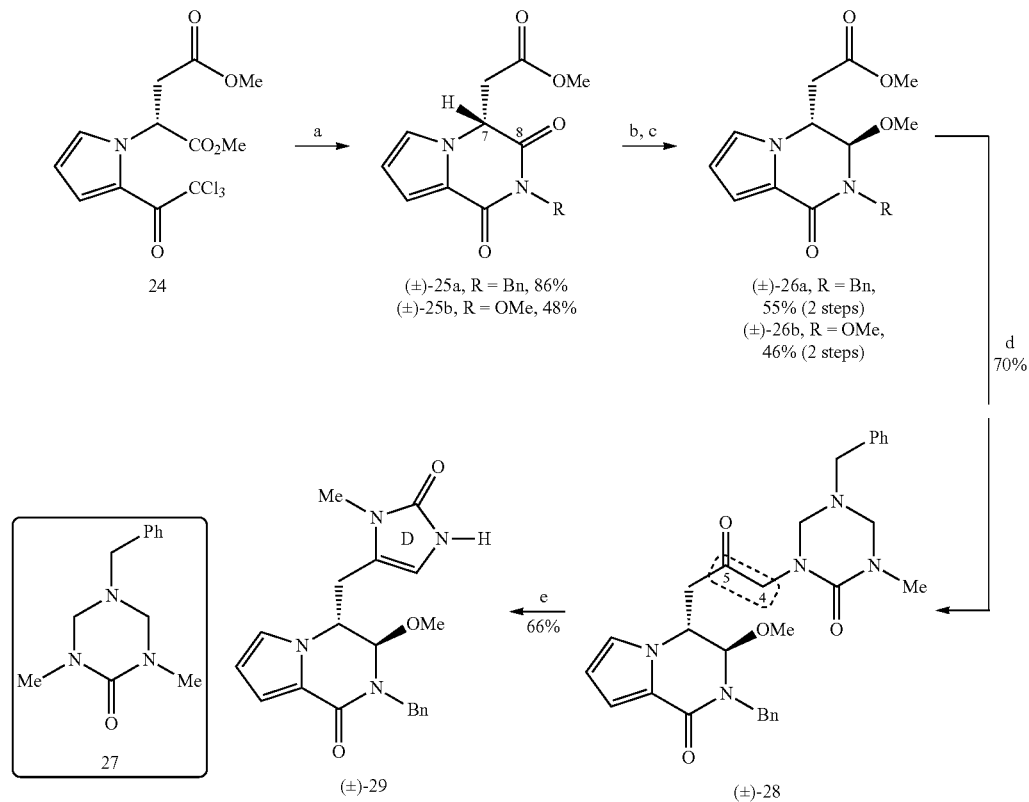

to give sulfide (±)-32 (95%), which was oxidized to sulfoxide (±)-33 in 55% yield upon treatment with sodium periodate (6:4 dr). However, heating a solution of sulfoxide (±)-33 in acetonitrile resulted in the exclusive formation of pyrrolopyrazinone 31 (Scheme 6).

Scheme 6. Formation of pyrrolopyrazinone 31 under various conditions.

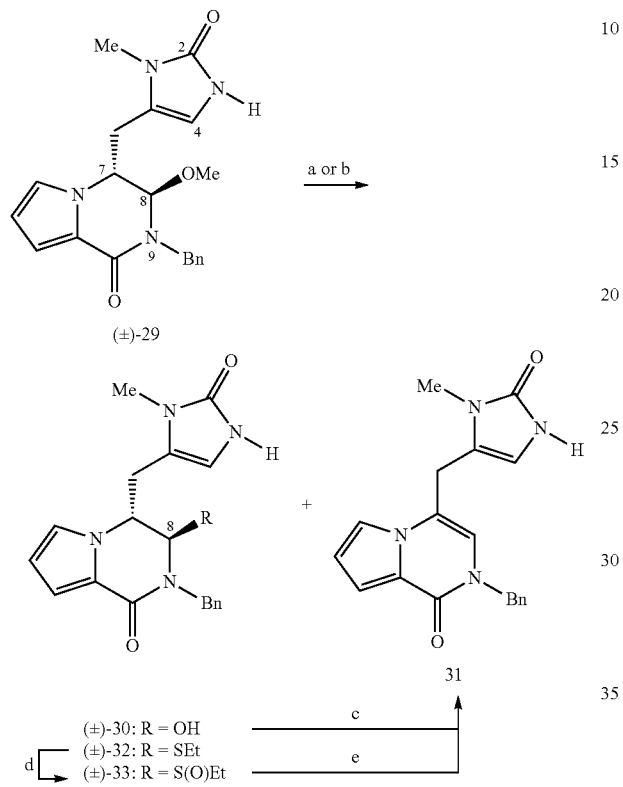

Conditions: (a) Sc(OTf)₃, H₂O, CH₃CN, 23° C. [(±)-30: 36%, 31: <5%]; (b) EtSH, TFA, CH₂Cl₂, 23° C. [(±)-32: 95%]; (c) CH₂Cl₂, TFA, 23° C., 95%; (d) NaIO₄, MeOH, H₂O, 23° C., 55%; (e) MeCN, 79° C., 100%.

The keto-triazone (±)-34, upon sequential treatment with samarium iodide (73% yield) followed by solvolysis in aqueous hydrochloric acid and methanol mixture, afforded the imidazolone (±)-35 (67% yield, Scheme 7). When imidazolone (±)-35 was treated with TFA-water mixture in acetonitrile, the elimination of methanol occurred to give pyrrolopyrazinone 36 in 95% yield (Scheme 7).

Scheme 7. Synthesis of imidazolone derivative (±)-35 and its reactivity under acidic condition.

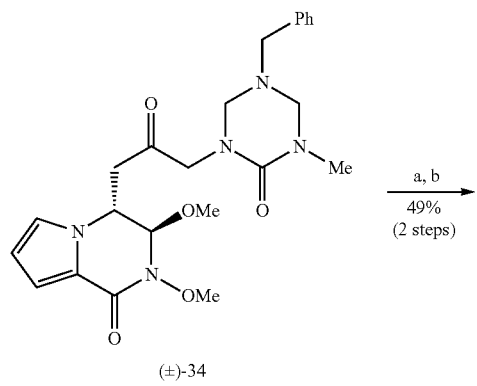

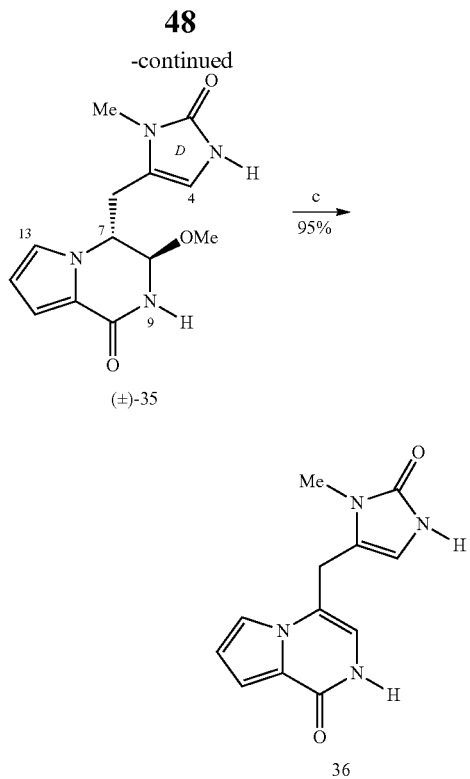

Conditions: (a) SmI₂, THF, MeOH, -78° C., 73%; (b) HCl (aq.), MeOH, 23° C., 67%; (c) TFA, H₂O, MeCN, 23° C., 95%.

Without the intention to be limited by theory, the formation of pyrrolopyrazinone 36 could be a result of rapid C7-deprotonation of the C8-iminium ion intermediate to generate the conjugated bicycle prior to the trapping of C8-electrophile with C4-nucleophile (Scheme 7). Substrate modifications that would lower the kinetic acidity of the proton at C7 and provide greater opportunity for the formation of the desired C4-C8 bond were tested. Not wishing to be limited by theory, Applicants reasoned that the allylic strain between the C13-bromide and the C6-methylene, present in all agelastatins, might hinder this tautomerization event. Comparison of the calculated minimum energy conformation of the acyliminium ion derived from C8-ionization of 35 and brominated acyliminium ion 8 (Scheme 1) revealed that the H7 of intermediate 8 is ~22° further away from ideal conformation for acidification as compared to that of the nonbrominated acyliminiun ion. Without the intention to be limited by theory, Applicants noted that the C7-proton of C13-brominated acyliminium ion 8 would be less susceptible to deprotonation as the overlap of C7-H7 σ-orbital with C8-N9 π*-orbital would be less than that of the nonbrominated acyliminium ion, and that the lowered kinetic acidity of H7 in the C13-brominated acyliminium ion intermediate 8 would provide greater prospect to trap the C8-electrophilic center with C4-nucleophile before the undesired H7-deprotonation.

For the introduction of the bromide at C13, keto-triazone 34 was treated with N-bromosuccinimide (NBS) to give bromopyrrole 37 in 45% yield (Scheme 8). Samarium iodide-mediated reduction of N-methoxylactam 37 (64% yield) followed by treatment with aqueous hydrogen chloride in methanol afforded (±)-O-methyl-pre-agelastatin A

(39) in 65% yield. When (±)-O-methyl-pre-agelastatin A (39) was treated with TFA and water in acetonitrile, (±)-agelastatin A (1) and (±)-di-epi-agelastatin A (40) were obtained as a 2:1 mixture in 47% combined yield. Careful monitoring of this transformation revealed that (±)-4,5-di-epi-agelastatin A (40) was the kinetic product, which equilibrated to the thermodynamically favored (±)-agelastatin A (1). With confirmation of the key step at hand, the synthesis of (±)-O-methyl-pre-agelastatin A (39) could be streamlined via a fragment assembly that would obviate the need for the N-methoxy substitution of the B-ring lactam.

Second Generation of Total Synthesis

Without the intention to be limited by theory, Applicants rationalized that a facile and reversible enolization at C7 caused the racemization of imide derivatives 25a and 25b (Scheme 5), and envisioned that the bromination at C13 of these imides would lower the kinetic acidity of their H7 and potentially minimize erosion of their enantiomeric excess. Amide (+)-41 could be obtained in two steps from a known pyrrole derivative upon bromination and acylation. When amide (+)-41 was dissolved in methanol-$d_4$ facile B-ring cyclization was observed. Importantly, it took 1 h for the C7-methine to show 52% deuterium incorporation and an

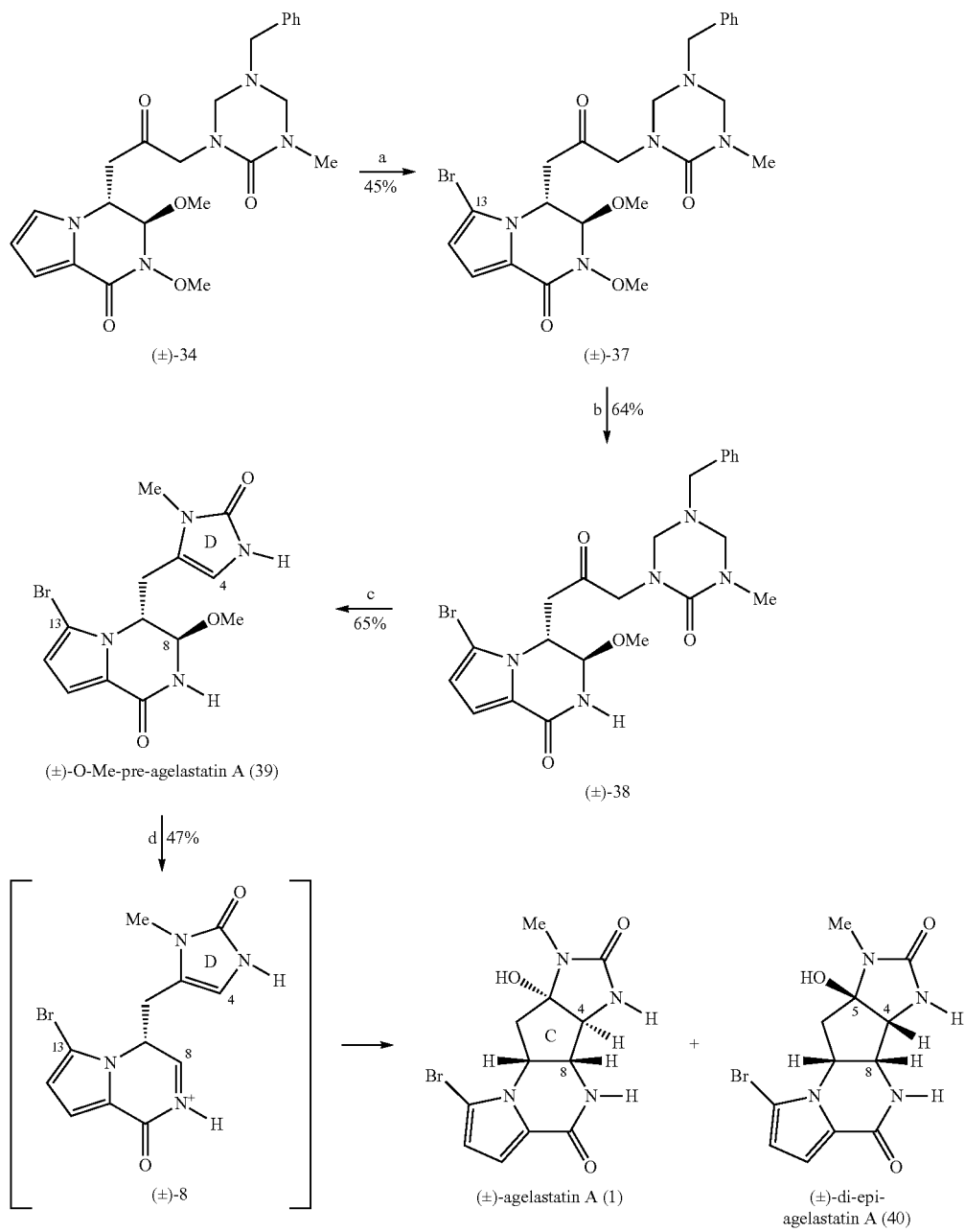

Scheme 8. First generation total synthesis of (±)-agelastatin A (1).

Conditions: (a) NBS, MeCN, 0° C., 45%; (b) SmI$_2$, THF, -78° C., 64%; (c) HCl (aq.), MeOH, 23° C., 65%; (d) H$_2$O, MeCN, TFA, 40° C., 47% (2:1, (±)-1:(±)-40).

additional 2 hours to show complete deuterium incorporation (Scheme 9), which could provide a small window of opportunity to intercept the imide carbonyl C8 via a rapid reduction before racemization.

Scheme 9. Cyclization and deuterium incorporation at C7 of amide (+)-41.

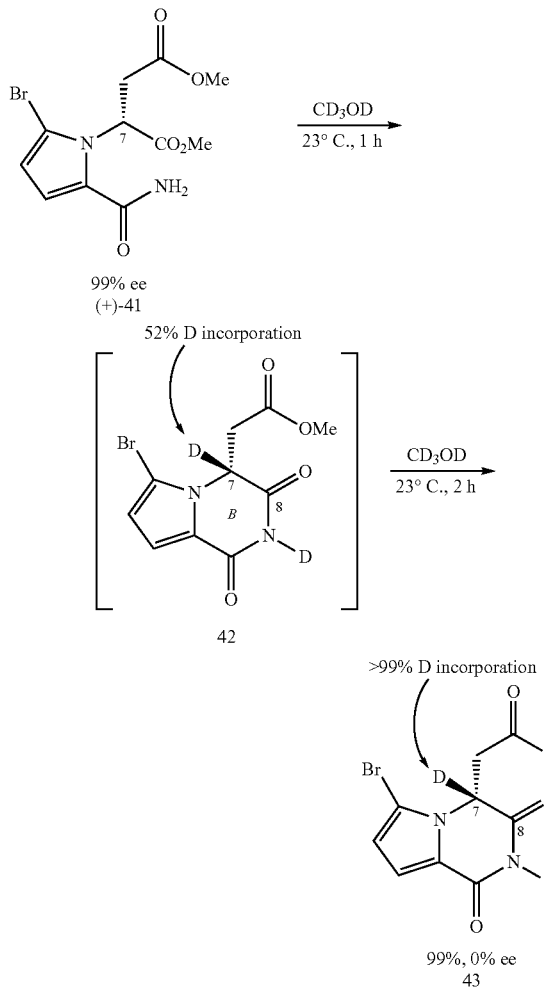

Exposure of methyl ester (+)-41 to sodium borohydride in methanol at 0° C. (Scheme 10) led to cyclization and reduction of the resulting imide to afford an α-hydroxyamide intermediate. Subsequent addition of p-toluenesulfonic acid monohydrate to the reaction mixture enabled a methanolysis reaction to directly give bicycle (+)-44 in 90% (>10 g-scale) and 99% ee.

Scheme 10. Synthesis of bicycle (+)-44.

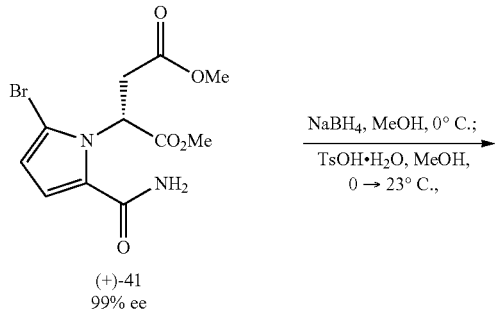

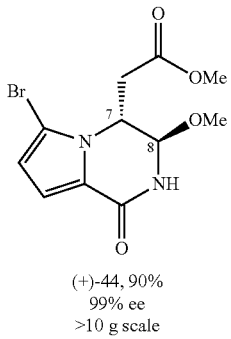

(+)-44, 90%
99% ee
>10 g scale

While the C13-bromide served critical roles in both suppressing C7-racemization (Scheme 10) and enabling the key C-ring cyclization (Schemes 8), it was incompatible with the addition of the lithiated triazone to methyl ester (+)-44 as detailed in Scheme 5. When the same lithiated triazone was exposed to methyl ester (+)-44, the reaction was plagued by the undesired reactivity between the C13-bromide and the organolithium species. The corresponding Grignard, organocerium, organocuprate, and organozinc derivatives failed to add to methyl ester (+)-44. However, Applicants found that the organocerium triazone derivative added smoothly to an aldehyde variant of ester (+)-44 for the introduction of the C4-C5 bond (64% yield), enabling the second generation total synthesis of (−)-agelastatins A (1) and B (2). Following the successful access to enantiomerically enriched alkaloids (−)-1 and (−)-2 via strategic introduction of C13-bromide at an early stage of the synthesis, a more concise strategy was pursued for the union of the desired triazone fragment and the readily available bicyclic ester (+)-44.

Third Generation of Total Synthesis

As an example, Applicants described herein an efficient metal-mediated cross-coupling reaction between thioester (+)-45, derived from methyl ester (+)-44 in one step, and a stannyl triazone derivative (Table 1). Under the previously reported reaction conditions, thioester (+)-45 and triazone 46 in the presence of Pd$_2$(dba)$_3$, Cu(I) diphenylphosphinate (CuDPP), and triethyl phosphite in THF at 23° C. failed to deliver the desired product (Table 1, entry 1). Substitution of triethyl phosphite with SPhos also showed no improvement (Table 1, entry 2). Surprisingly, upon treatment of thioester (+)-45 and triazone 46 with a catalytic amount of Pd(PPh$_3$)$_4$ and stoichiometric amount of CuDPP at 50° C., the desired coupled product (+)-48 was obtained in 50% yield. Under these conditions, byproduct 49a, resulting from an undesired transfer of a n-butyl group from the stannane 46, was also formed in 50% yield (Table 1, entry 3). Unexpectedly, by switching the copper additive to Cu(I)-thiophene-2-carboxylate (CuTC), the formation of the desired coupled product (+)-48 (60% yield) was favored over the undesired byproduct 49a (40% yield, Table 1, entry 4). Even more surprisingly, this transformation could be carried out with equal efficiency without the palladium catalyst (Table 1, entry 5). To suppress the undesired alkyl transfer, a stannyltriazone substrate 47 containing cyclohexyl groups was employed as auxiliary ligands to the tin. Surprisingly, when thioester (+)-45 and triazone 47 were treated with CuTC (1.5 equiv) at 50° C., the desired ketone (+)-48 was formed exclusively in 96% yield and 99% ee (>5 g-scale, Table 1, entry 6).

TABLE 1

Copper-mediated cross-coupling between thioester (+)-45 and stannyl triazone derivatives.

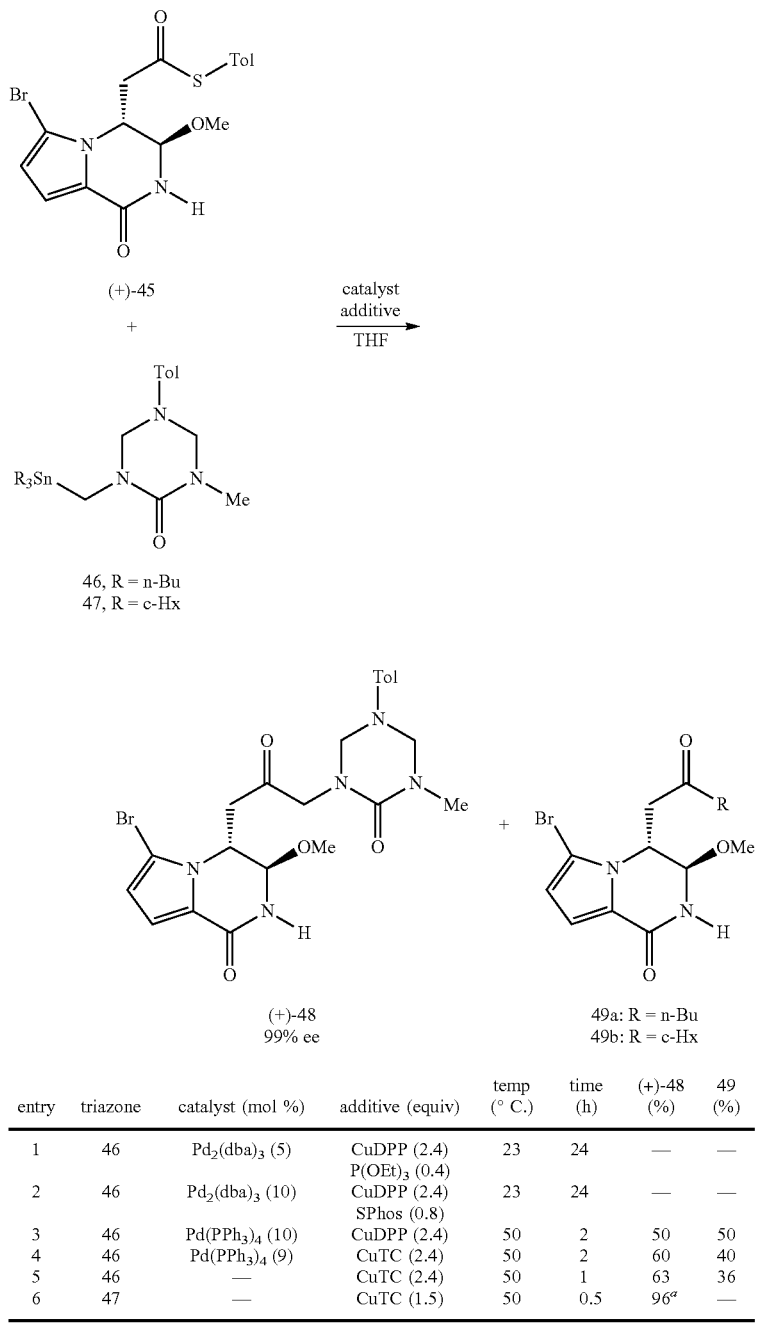

| entry | triazone | catalyst (mol %) | additive (equiv) | temp (° C.) | time (h) | (+)-48 (%) | 49 (%) |
|---|---|---|---|---|---|---|---|
| 1 | 46 | Pd$_2$(dba)$_3$ (5) | CuDPP (2.4) P(OEt)$_3$ (0.4) | 23 | 24 | — | — |
| 2 | 46 | Pd$_2$(dba)$_3$ (10) | CuDPP (2.4) SPhos (0.8) | 23 | 24 | — | — |
| 3 | 46 | Pd(PPh$_3$)$_4$ (10) | CuDPP (2.4) | 50 | 2 | 50 | 50 |
| 4 | 46 | Pd(PPh$_3$)$_4$ (9) | CuTC (2.4) | 50 | 2 | 60 | 40 |
| 5 | 46 | — | CuTC (2.4) | 50 | 1 | 63 | 36 |
| 6 | 47 | — | CuTC (1.5) | 50 | 0.5 | 96$^a$ | — |

$^a$Reaction was performed in >5 g scale.
Tol = C$_6$H$_4$-p-Me, c-Hx = cyclohexyl.

Having established a reliable method to access ketone (+)-48, Applicants next optimized the final steps leading to (−)-agelastatin A (1). Keto-triazone (+)-48 was most efficiently converted to (+)-O-methyl-pre-agelastatin A (39) upon exposure to methanolic hydrogen chloride at 65° C. (89% yield, 99% ee, Scheme 11). Additionally, treatment of (+)-O-methyl-pre-agelastatin A (39) with aqueous methanesulfonic acid at 100° C., followed by introduction of methanol to the resulting mixture of (−)-agelastatin A (1) and (−)-di-epi-agelastatin A (40), afforded (−)-agelastatin A (1) in 49% yield (99% ee, >1 g-scale) along with (−)-O-methyl-di-epi-agelastatin A (50, 22% yield, Scheme 11), Not only could diastereomer 50 be readily separated by flash column chromatography, but its resubmission to the above protocol provided another batch of (−)-agelastatin A (1) in 66% yield along with recovered (−)-50 in 30% yield. While treatment of an aqueous tetrahydrofuran solution of (−)-agelastatin A (1) with NBS and 2,6-di-t-butyl-4-methylpyridine (DT-BMP) efficiently afforded (−)-agelastatin B (2) in 84% yield, the exposure of a methanolic solution of (−)-1 to amberlyst 15 resin provided (−)-agelastatin E (5) in 96% yield.

Scheme 11. Enantioselective synthesis of (−)-agelastatins A-C (1-3) and E (5).

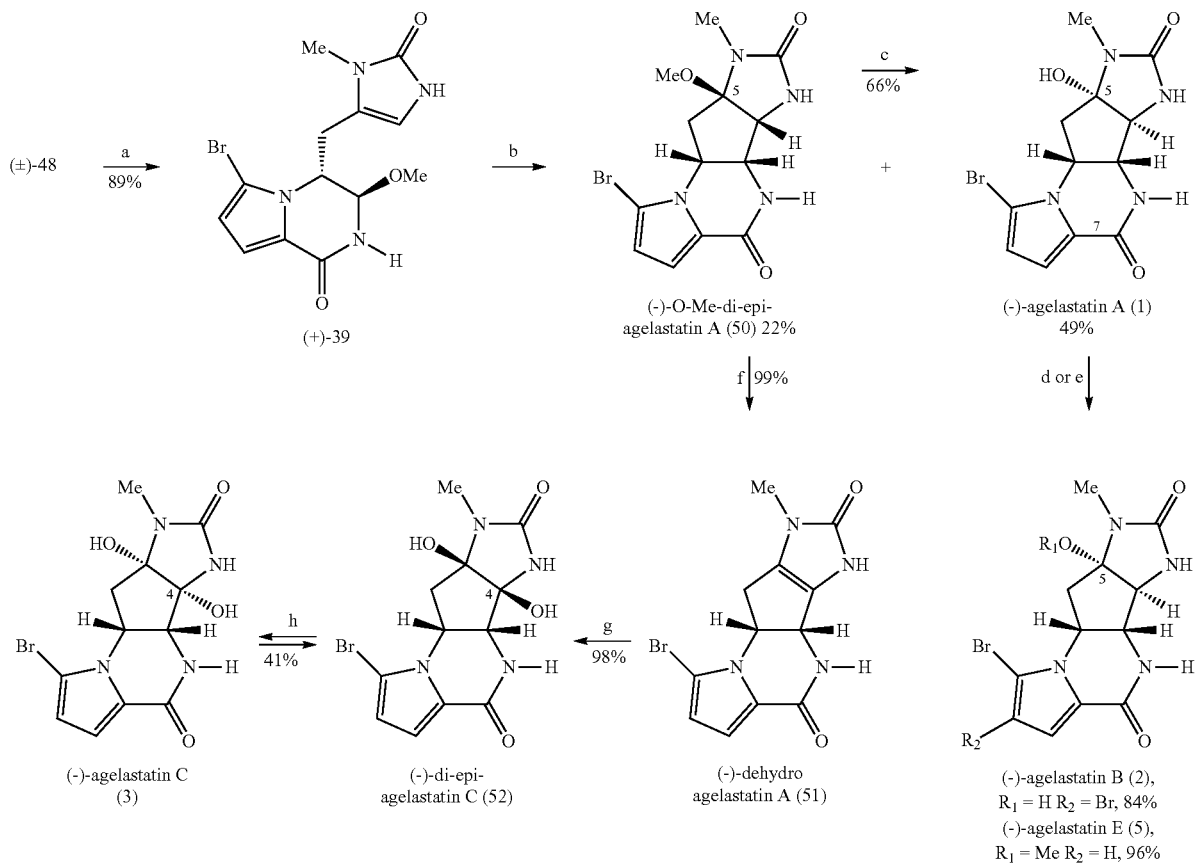

Conditions: (a) HCl (aq.), MeOH, 65° C., 89%; (b) MeSO₃H, H₂O, 100° C.; MeOH, 71% [2:1, (−)-1:(−)-50]; (c) MeSO₃H, H₂O, 100° C.; MeOH [66% of (−)-1, and 30% of recovered (−)-50]; (d) NBS, DTBMP, THF, H₂O, 0° C., 84% (1 → 2); (e) Amberlyst 15, MeOH, 65° C., 96% (1 → 5); (f) pyridine, 115° C., 99%; (g) DMDO, acetone, H₂O, 0° C., 98%; (h) Amberlyst 15, H₂O, 100° C., 41%.

Concerning the synthesis of (−)-agelastatin C (3), a wide range of oxidants tested was found to be ineffective for the direct oxidation of the C4-methine of (−)-agelastatin A (1). A strategy was devised based on the oxidation of (−)-dehydroagelastatin A (51, Scheme 11). (−)-O-methyl-di-epi-agelastatin A (50) was readily converted to (−)-dehydroagelastatin A (51) upon heating in pyridine at 115° C. in 95% yield (Scheme 11), Treatment of (−)-dehydroagelastatin A (51) with dimethyldioxirane (DMDO) provided (−)-di-epi-agelastatin C (52) in 98% yield, via oxidation on the convex face. Notably, heating an aqueous solution of (−)-di-epi-agelastatin C (52) in the presence of amberlyst 15 resin afforded (−)-agelastatin C (3) in 41% yield along with recovered (−)-di-epi-agelastatin C (52, 42% yield).

The copper-mediated cross-coupling reaction of thioester and organostannane enabled an efficient synthesis of (+)-O-methyl-pre-agelastatin D (53, Scheme 12) as described in the following section (Table 2), and consequently the first synthetic sample of (−)-agelastatin D (4). When (+)-O-methyl-pre-agelastatin D (53) was heated in aqueous acidic solution followed by methanol treatment, (−)-agelastatin D (4) was obtained in 26% yield along with (−)-O-methyl-di-epi-agelastatin D (54, 9% yield, Scheme 12). The reaction also provided compound 55 (20% yield) and compound 56 (20% yield).

Scheme 12. Total synthesis of (−)-agelastatin D (4) and the formation of byproducts 55 and 56.

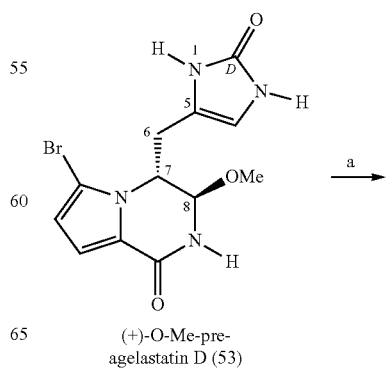

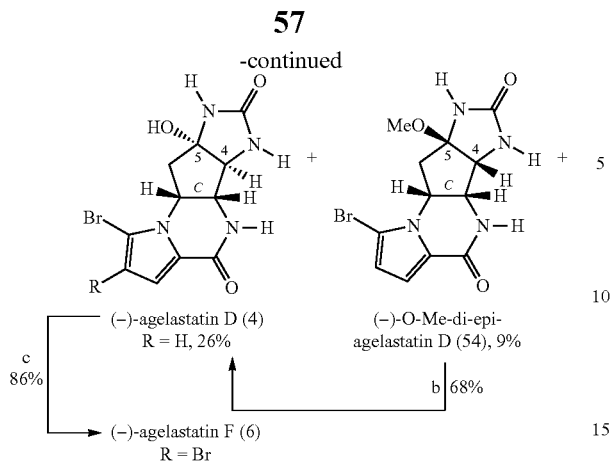

(−)-agelastatin D (4)
R = H, 26%

(−)-O-Me-di-epi-
agelastatin D (54), 9% c | 86%
b | 68%

(−)-agelastatin F (6)
R = Br

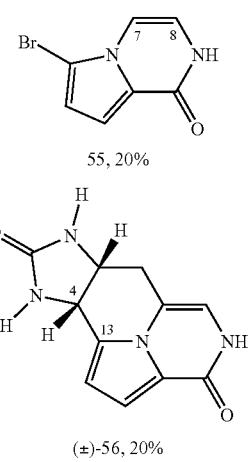

55, 20%

(±)-56, 20%

Conditions: (a) MeSO₃H, H₂O, 100° C.; HCl, MeOH [26% (−)-4, 9% (−)-54, 20% 55, 20% (±)-56]; (b) MeSO₃H, H₂O, 100° C.; HCl, MeOH, 23° C., 68%; (c) NBS, DTBMP, THF, H₂O, 0° C., 86%. DTBMP = 2,6-di-t-butyl-4-methylpyridine.

Heating an aqueous acidic solution of 13-desbromoenamide 57 resulted in clean formation of tetracycle 56 (46%). Without the intention to be limited by theory, Applicants propose that byproduct 56 may be formed via protodebromination at C13, followed by enamide formation, and C4 to C13 cyclization; a mechanism involving protodebromination after the C4-C13 cyclization might also be possible.

Scheme 13. Formation of the C4-C13
bond upon acidic treatment of enamide 57.

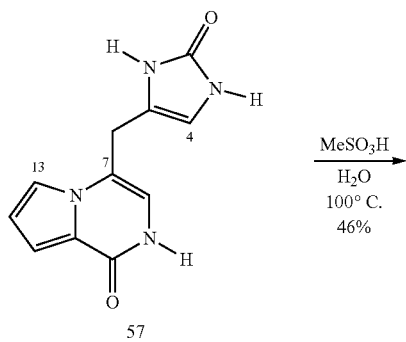

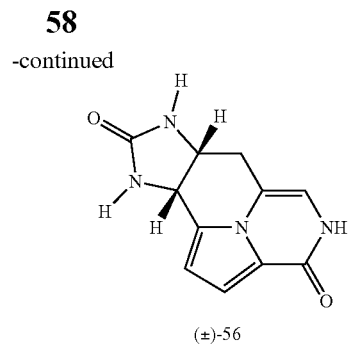

(±)-56

Without the intention to be limited by theory, Applicants propose that the formation of byproducts 55 and 56 may be consistent with the lower C4-nucleophilicity of (+)-O-methyl-pre-agelastatin D (53) compared to that of (+)-O-methyl-pre-agelastatin A (39): monitoring of the rates of deuterium incorporation at C4 position of (+)-O-methyl-pre-agelastatins A (39) and D (53), respectively, revealed that deuterium incorporation at C4 occurred ten times faster in (+)-39 as compared to (+)-53 ($k_1=3.094\times10^{-5}$/sec, $k_2=3.028\times10^{6}$/sec), consistent with its more efficient C4-C8 bond formation (Scheme 14). Not wishing to be limited by theory, Applicants note that the scarcity of natural (−)-agelastatin D (4) compared to other N1-methyl agelastatin alkaloids is consistent with this observation on the lower efficiency of the desired cyclization with 53 as compared to 39.

Scheme 14. Rate constants for the
deuterium incorporation at C4 of (+)-39 and (+)-53.

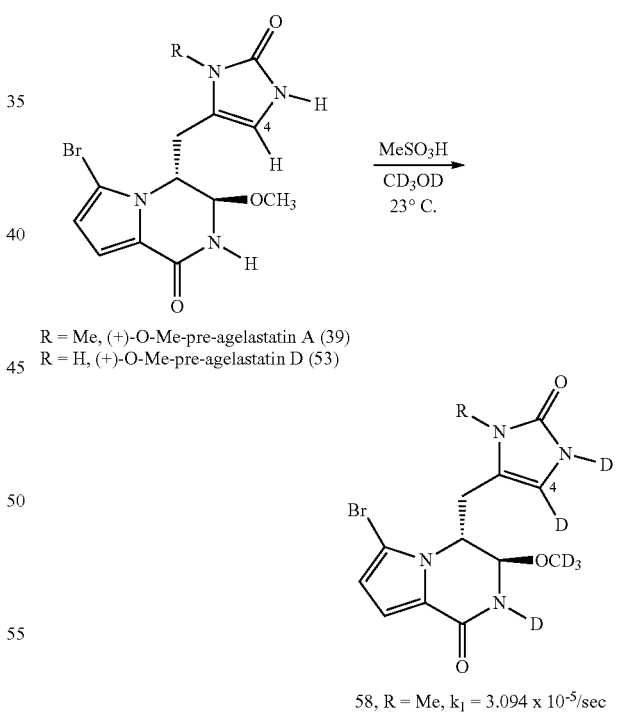

R = Me, (+)-O-Me-pre-agelastatin A (39)
R = H, (+)-O-Me-pre-agelastatin D (53)

58, R = Me, $k_1 = 3.094 \times 10^{-5}$/sec
59, R = H, $k_2 = 3.028 \times 10^{-6}$/sec Copper-Mediated Cross-Coupling Reaction of Thioesters and Organostannanes—Additional Examples The copper-mediated cross-coupling reactions between thioester, for example, 45 and organostannanes, for example, 46 and 47 (Table 1) has broad scope and applications (Scheme 15). Of particular interest was the general use of this methodology to allow synthesis of versatile ketone 62 by formation of the C1-C2 bond from thioester 60 and organostannane 61 (X=O or NR). Condensative cyclization of the urea or guanidine function of intermediate 62 on to the C1-carbonyl would provide an expeditious route to the corresponding imidazol-2-one (X=O) or related azaheterocycle 63, common substructures in various natural products.

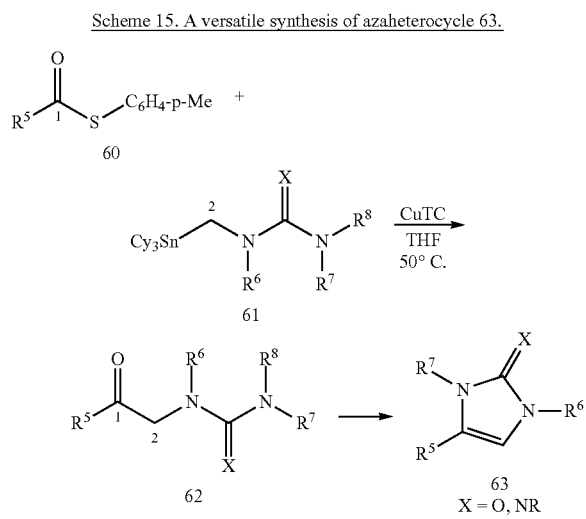

Scheme 15. A versatile synthesis of azaheterocycle 63.

In some embodiments, $C_6H_4$-p-Me is replaced with another suitable organic group, for example, $R^9$.

A provided cross-coupling reaction was effective for both alkyl and aryl thioester coupling partners. Both cyclohexanecarbonyl thioester 64 and benzoyl thioester 65 underwent efficient cross-coupling with stannyl triazone 47 to give the corresponding ketones 71 and 72 in 95% and 99% yield, respectively (Table 2, entries 1 and 2). Consistent with data presented in Table 1, the use of organostannane 46, containing n-butyl auxiliary ligands, as a coupling partner resulted in relatively low but good yield (Table 2, entry 3) due to competitive formation of the undesired n-butyl ketone byproduct. Stannyl guanidine 67 proved to be highly effective for the introduction of the guanidine functionality as illustrated through its cross-coupling with thioesters 65 and 66, affording the corresponding ketones 73 and 75, respectively (Table 2, entries 4 and 6) Importantly, ketones 73 and 75 could be readily converted to the corresponding 2-aminoimidazoles in quantitative yield upon treatment with TFA and warming, highlighting the synthetic utility of the method as a means to generate 2-aminoimidazoles (Table 2, entries 5 and 7). Stannyl triazone 68 was found to undergo smooth coupling with adipic thioester 66 to provide diketone 77 in 82% yield (Table 2, entry 8). Under provided standard reaction condition, the stannyl urea 69 was found to afford the desired cross-coupling with the complex thioester (+)-45 to give the corresponding ketone, which after treatment with methanolic hydrogen chloride at 65° C. provided (+)-O-methyl-pre-agelastatin A (39, 58% yield and 99% ee, Table 2, entry 9). This direct coupling between thioester (+)-45 and stannyl urea 69 enabled us to further streamline the synthesis of (−)-agelastatin A (1) to seven steps from commercially available material. Similarly, (+)-O-methyl-pre-agelastatin D (53 Table 2, entry 10) could be prepared from thioester (+)-45 and urea 70 in 62% yield (2 steps), which enabled the first synthetic access to (−)-agelastatin D (4, vide supra). The efficient union of a variety of aminostannanes and thioester fragments and subsequent direct conversion of the keto-triazone and keto-guanidine intermediates to the corresponding imidazolones and aminoimidazoles showed that provided methods could be used for the synthesis of other compounds, for example, coroidin based natural products such as cyclooroidin (11), nagelamides, sceptrins, and many other derivatives.

TABLE 2

Copper-mediated thioester-aminostannane cross-coupling and application to azaheterocycle synthesis.

| entry | thioester | stannane (equiv) | CuTc equiv | product | yield (%) |
|---|---|---|---|---|---|
| 1 | 64 | 47 (1.5) | 1.2 | 71 | 95 |

TABLE 2-continued

Copper-mediated thioester-aminostannane cross-coupling and application to azaheterocycle synthesis.

| # | Thioester | Stannane | Equiv | Product | Yield (%) |
|---|---|---|---|---|---|
| 2 | 65 | 47 (1.5) | 1.2 | 72 | 99 |
| 3 | 65 | 46 (1.1) | 1.5 | 72 | 52 |
| 4 | 65 | 67 (1.1) | 1.0 | 73 | 96 |
| 5 | 65 | 67 (1.1) | 1.0 | 74 | 96[a] |
| 6 | 66 | 67 (3.0) | 2 | 75 | >99 |
| 7 | 66 | 67 (3.0) | 2 | 76 | >99[b] |

TABLE 2-continued

Copper-mediated thioester-aminostannane cross-coupling and application to azaheterocycle synthesis.

| | | | | | |
|---|---|---|---|---|---|
| 8 | 66 | 68 (2.5) | 2.3 | 77 | 82 |
| 9 | (+)-45 | 69 R = Me (3) | 2.5 | (+)-O—Me-pre-agelastatin A (39), R = Me | 58[c] |
| 10 | (+)-45 | 70 R = H (3) | 2 | (+)-O—Me-pre-agelastatin D (53), R = H | 62[d] |

[a]The ketone intermediate 73 was treated with TFA in toluene at 85° C.; yield over two steps.
[b]The ketone intermediate 75 was treated with TFA in toluene at 70° C.; yield over two steps.
[c]ketone intermediate was filtered and treated with HCl in methanol at 65° C.; one step.
[d]Cross-coupling intermediate was isolated and treated with HCl in methanol at 45° C.; yield over two steps.
Tol = $C_6H_4$-p-Me, c-Hex = cyclohexyl.

Anticancer Activity

The six (−)-agelastatin alkaloids (1-6) as well as eight structurally-related alkaloids and advanced intermediates were tested as examples for anti-cancer activity. The activities against five human cell lines were first measured. Random reports have tested the activity of (−)-agelastatin A (1), however, it was unknown before for what cancer(s), if any, agelastatin alkaloids could be used for treatment.

TABLE 3

Assessment of the anti-cancer activity of (−)-agelastatins A-F and advanced intermediates against human cell lines.[a]

| Cmpd | U-937 (μM) | HeLa (μM) | A549 (μM) | BT549 (μM) | IMR90 (μM) |
|---|---|---|---|---|---|
| (−)-1 | 0.067 ± 0.003 | 0.708 ± 0.090 | 1.05 ± 0.14 | 0.278 ± 0.076 | 1.11 ± 0.35 |
| (−)-2 | 1.06 ± 0.16 | 4.8 ± 1.2 | >10 | 4.8 ± 1.1 | >10 |
| (−)-3 | >10 | >10 | >10 | >10 | >10 |
| (−)-4 | 0.240 ± 0.033 | 1.00 ± 0.20 | 0.92 ± 0.16 | 0.631 ± 0.082 | 2.75 ± 0.60 |
| (−)-5 | 2.56 ± 0.13 | 8.60 ± 0.81 | >10 | 6.9 ± 2.5 | >10 |
| (−)-6 | >10 | >10 | >10 | >10 | >10 |
| (−)-50 | >10 | >10 | >10 | >10 | >10 |
| (−)-51 | >10 | >10 | >10 | >10 | >10 |
| (−)-52 | >10 | >10 | >10 | >10 | >10 |
| (+)-39 | >10 | >10 | >10 | >10 | >10 |
| (+)-44 | >10 | >10 | >10 | >10 | >10 |
| (+)-45 | >10 | >10 | >10 | >10 | >10 |
| (+)-48 | >10 | >10 | >10 | >10 | >10 |
| (+)-53 | >10 | >10 | >10 | >10 | >10 |

[a]Cell lines: U-937, lymphoma; HeLa, cervical carcinoma; A549, non-small cell lung carcinoma; BT549, breast carcinoma; IMR90, immortalized lung fibroblasts; 48-hour $IC_{50}$ values (in μM) as determined by MTS (U-937) and SRB (HeLa, A549, BT549, and IMR90); MTS = 3-(4,5-dimethylthiazol-2-yl)-5-(3-carboxymethoxyphenyl)-2-(4-sulfophenyl)-2H-tetrazolium); SRB = sulforhodamine B.

Six (−)-agelastatins along with eight closely related derivatives prepared in the above examples were tested (Table 3). The six (−)-agelastatin alkaloids (1-6, respectively), (−)-O-methyl-di-epi-agelastatin A (50), (−)-dehydroagelastatin A (51), (−)-di-epi-agelastatin C (52), (+)-O-methyl-pre-agelastatin A and D (39 and 53, respectively), along with bicyclic pyrroles (+)-44, (+)-45, and triazone (+)-48 were tested for their ability to induce cell death in four human cancer cell lines (U-937, lymphoma; HeLa, cervical carcinoma; A549, non-small cell lung carcinoma; and BT549, breast carcinoma) and one immortalized normal human cell line (IMR90, lung fibroblasts) after a 48-hour exposure. As shown in Table 3, (−)-agelastatin A (1) exhibited the highest potency in all cell lines tested, whereas (−)-agelastatins C (3) and F (6) showed little activity at the concentrations examined. Furthermore, enhanced activities in U-937 (20×) cell relative to the other cell lines (Table 3) were observed. (−)-Agelastatin B (2) and (−)-agelastatin E (5) showed relatively weaker activity, albeit with the same overall pattern as alkaloids (−)-1 and (−)-4. None of the epi-agelastatin derivatives [(−)-50 or (−)-52], O-methyl-pre-agelastatins [(+)-39 or (+)-53], dehydroagelastatin (−)-51 or any of structurally simpler derivatives [(+)-44, (+)-45, or (+)-48] showed any activity at the concentrations tested against these cell lines (Table 3).

This set of data allows the first direct comparison of agelastatin alkaloids and suggest that, without the intention to be limited by theory, the stereochemistry for the imidazolidinone ring is crucial [compare (−)-5 vs. (−)-50]. Not wishing to be bound by theory, Applicants note that addition of the C14-bromide substituent to the pyrrole, in some embodiments, is detrimental to activity (5-20 fold reduction) of the agelastatins [compare (−)-1 vs. (−)-2, and (−)-4 vs. (−)-6]; and demethylation of the imidazolidinone ring gives more modest reductions (1-5 fold reductions) in anticancer potency as seen by comparing (−)-agelastatin A (1) and (−)-agelastatin D (4). In some embodiments, methylation of the C5-hydroxyl reduces the activity by >10 fold as evident by comparing (−)-agelastatin A (1) and (−)-agelastatin E (5). In some embodiments, C4-hydroxylation abolishes activity as demonstrated by comparing (−)-agelastatin A (1) and (−)-agelastatin C (3).

Anticancer Activity in Blood Cancer Cells

Based on the surprising and exceptional potency of (−)-agelastatins A (1) and D (4) against U-937 cells relative to the other cell lines tested, five additional blood cancer cell lines were tested for their sensitivity to the agelastatin alkaloids. These cell lines spanned a variety of cancer types (CEM, acute lymphoblastic leukemia; Jurkat, acute T-cell leukemia; Daudi, Burkitt's lymphoma; HL-60, acute promyelocytic leukemia; CA46, Burkitt's lymphoma). After a 48-hour incubation, the ability of (−)-agelastatins A-F (1-6) to induce cell death was evaluated. As shown in Table 4, all five cell lines showed remarkable sensitivity to (−)-agelastatin A (1). The same trends in potency observed for the various agelastatins with the general cell panel (Table 3) were also observed. These results highlight that compounds of formula I are unexpectedly potent against blood cancers.

TABLE 4

48-hour activity of (−)-agelastatins A-F against human blood cancer cell lines.[a]

| Cmpd | CEM (μM) | Jurkat (μM) | Daudi (μM) | HL-60 (μM) | CA46 (μM) |
| --- | --- | --- | --- | --- | --- |
| (−)-1 | 0.020 ± 0.002 | 0.074 ± 0.007 | 0.020 ± 0.003 | 0.138 ± 0.066 | 0.187 ± 0.071 |
| (−)-2 | 0.29 ± 0.20 | 0.75 ± 0.44 | 0.46 ± 0.28 | 2.4 ± 1.0 | 1.07 ± 0.42 |
| (−)-3 | 2.1 ± 1.3 | 5.31 ± 0.35 | 7.2 ± 2.9 | >10 | >10 |
| (−)-4 | 0.074 ± 0.025 | 0.210 ± 0.063 | 0.202 ± 0.015 | 0.54 ± 0.12 | 0.46 ± 0.24 |
| (−)-5 | 0.83 ± 0.37 | 1.50 ± 0.33 | 1.41 ± 0.53 | 4.6 ± 3.6 | 2.45 ± 0.95 |
| (−)-6 | >10 | >10 | >10 | >10 | >10 |

[a]Cell lines: CEM, acute lymphoblastic leukemia; Jurkat, acute T-cell leukemia; Daudi, Burkitt's lymphoma; HL-60, acute promyelocytic leukemia; CA46, Burkitt's lymphoma; 48-hour $IC_{50}$ values (in μM) as determined by MTS; MTS = 3-(4,5-dimethylthiazol-2-yl)-5-(3-carboxymethoxyphenyl)-2-(4-sulfophenyl)-2H-tetrazolium).

Hemolytic Activity

It was surprisingly found that compounds in the provided compositions and methods are not only unexpectedly potent toward blood cancer cells, but also have surprisingly low hemolytic activity. All fourteen compounds in Table 3 were evaluated for their hemolytic activity (FIG. 1). Notably, none of agelastatins (−)-1, (−)-2, (−)-4, or (−)-5 show any nonspecific hemolysis of red blood cells. Together with the exceptional potency of these compound, for example, (−)-agelastatin A (1), against a range of blood cancer cell lines, this high degree of selectivity makes these compounds valuable treatment for blood cancers.

Apoptotic Activity

Figure 2:
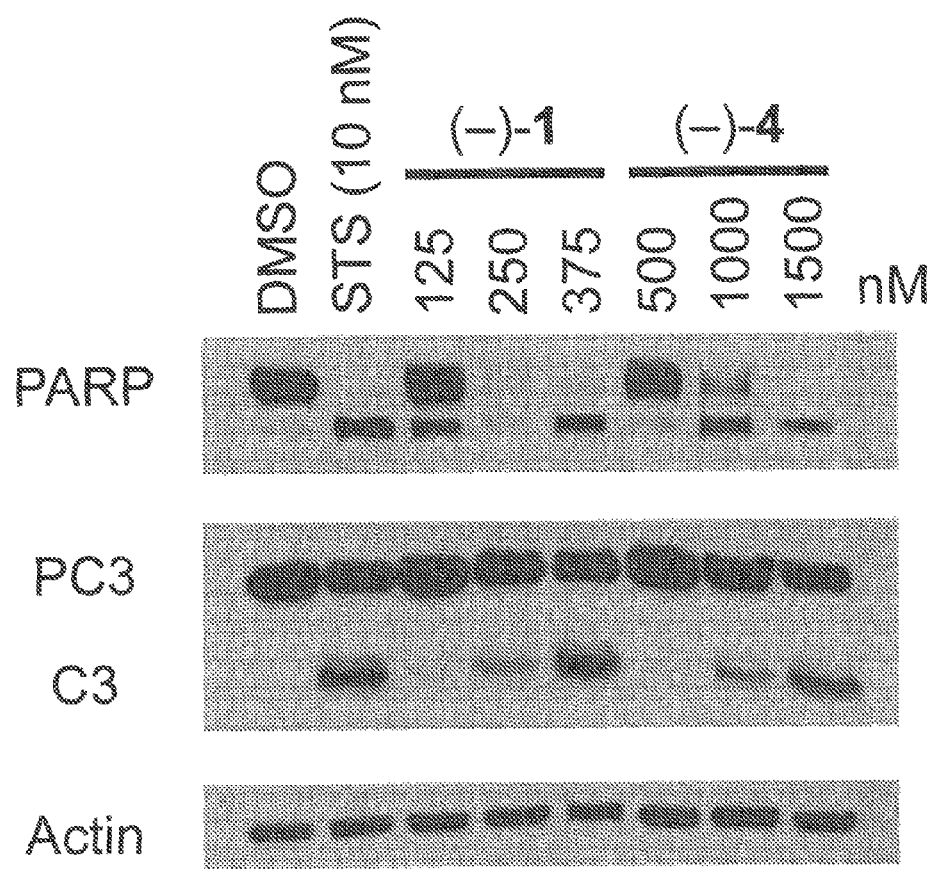
FIG. 2. (−)-Agelastatins A (1) and D (4) both induce caspase-dependent apoptotic cell death. Western blot analysis of procaspase-3 and PARP-1 cleavage at 24 hours in U-937 cells using β-actin as loading control. Compounds were tested at indicated concentrations and STS (10 nM); C3=caspase-3; PARP=poly(ADP-ribose) polymerase 1; PC3=procaspase-3; STS=staurosporine.

Compounds of formula I, such as (−)-agelastatins A (1) and D (4) induce apoptotic cell death. Procaspase-3 maturation and PARP-1 cleavage were readily detected via Western blotting, and phosphatidyl serine exposure is detected by antibody staining and flow cytometry. As shown in FIG. 2, (−)-agelastatins A (1) and D (4) induced dose-dependent activation of procaspase-3 to active caspase-3, and cleavage of PARP-1, consistent with apoptosis.

Figure 3:
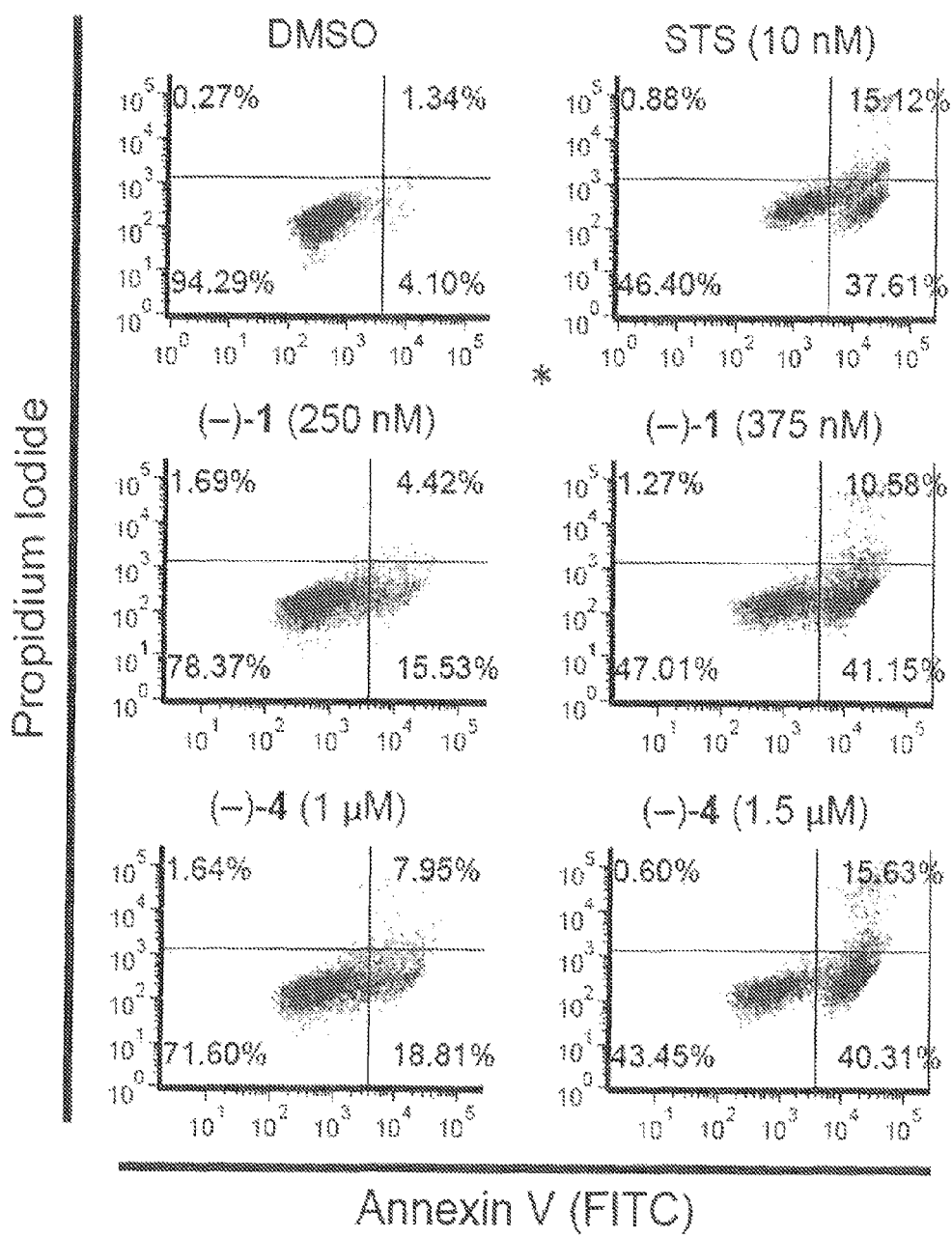
FIG. 3. (−)-Agelastatins A (1) and D (4) both induced dose-dependent apoptosis. Analysis of phosphatidylserine exposure and propidium iodide inclusion at 21 hours in U-937 cells. Compounds were tested at indicated concentrations and STS was used as a positive control for apoptosis. Samples were analyzed by flow cytometry for the relative timing of phosphatidylserine exposure relative to PI inclusion. FITC=fluorescein isothiocyanate; PI=propidium iodide; STS=staurosporine.
Figure 4:
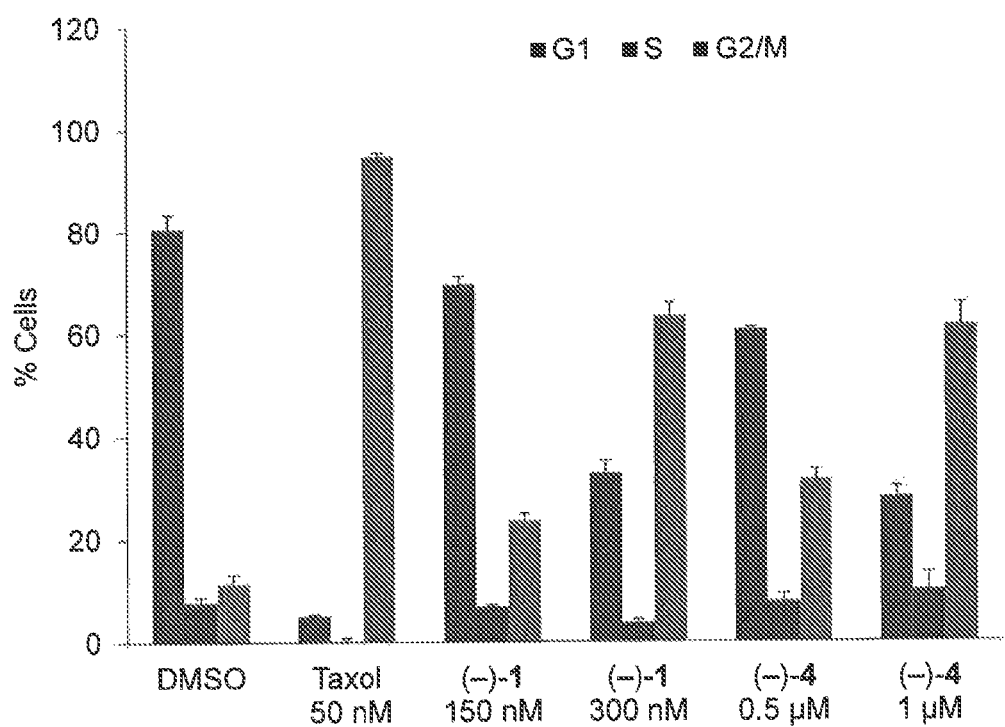
FIG. 4. (−)-Agelastatins A (1) and D (4) both exhibit dose-dependent G2/M cell cycle arrest in synchronized U-937 cells after 16 hours. Samples were fixed, treated with an RNAse, stained with PI, and analyzed by flow cytometry. Taxol, a microtubule stabilizer, was used as a positive control. Error bars represent standard deviation of the mean, n=3. * p<0.01. PI=propidium iodide.
Figure 7:
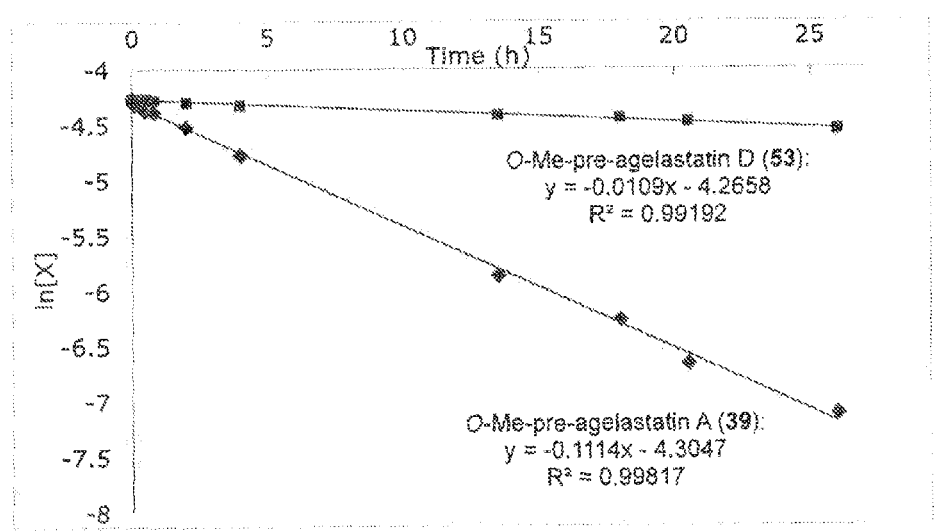
FIG. 7. Linear approximation of ln [SM] vs time of (+)-O-methyl-pre-agelastatins A (39) and D (53).
Figure 8:
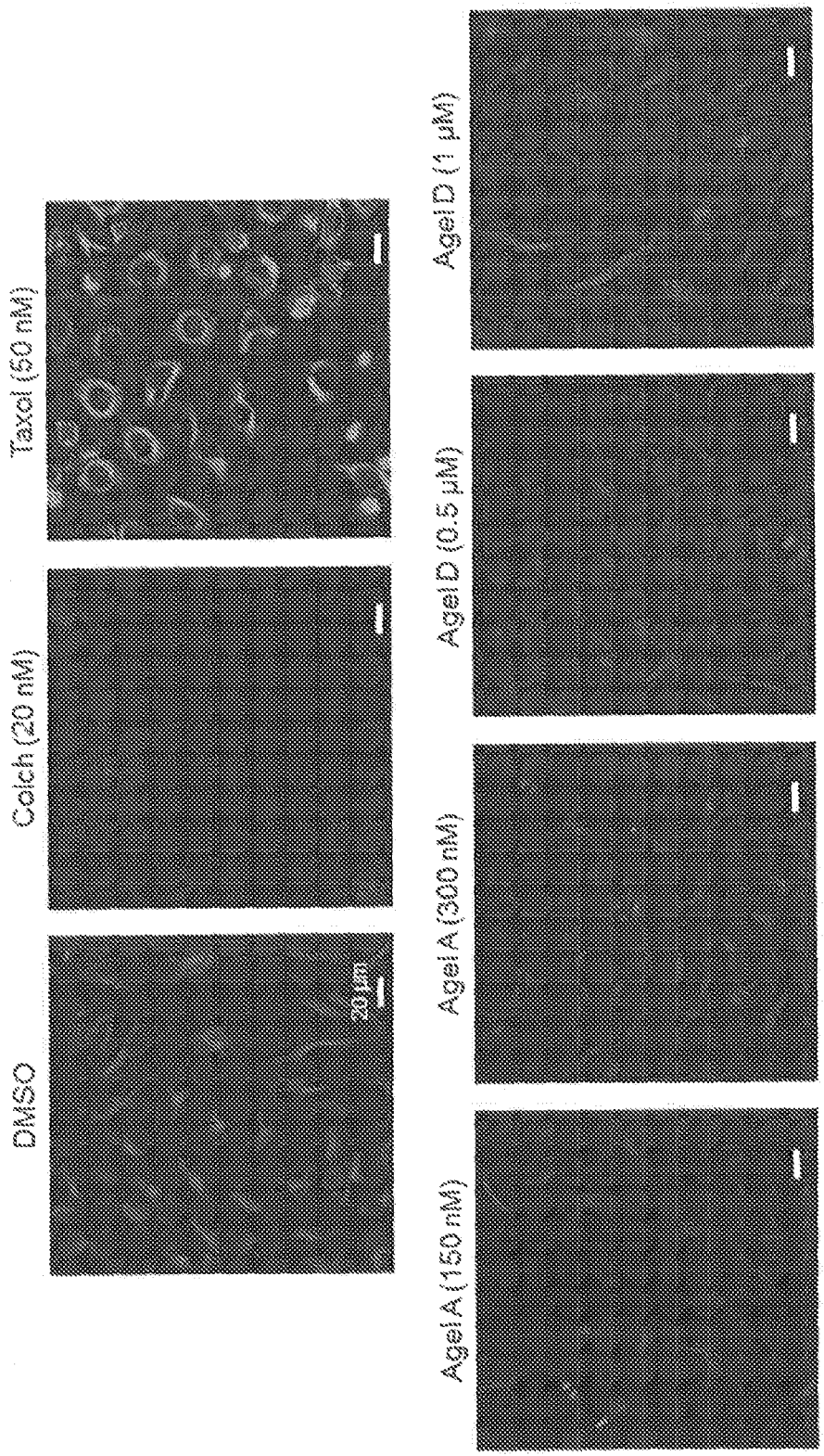
FIG. 8. Agelastatin A (1) and agelastatin D (4) do not affect tubulin dynamics. HeLa cells were treated with compound for 16 hours, fixed, stained, and visualized using confocal microscopy. Colchicine (colch) and taxol were used as positive controls for tubulin destabilization and stabilization, respectively.

It was next examined whether (−)-agelastatins A (1) and D (4) induced phosphatidylserine exposure prior to membrane permeabilization. This was determined by evaluating the timing of FITC-labeled annexin-V to the phosphatidylserines relative to the incorporation of propidium iodide, a DNA stain that can only enter dead cells. As shown by the scatterplots in FIG. 3, the number of apoptotic cells (lower right quadrant in FIG. 3) increases with dose of compound. These results show, for the first time, that these compounds induce apoptotic death of cancer cells.

Cell Cycle Arrest

Compounds of the provided compositions and methods induce cell cycle arrest. As shown in FIG. 5, provided compounds induced arrest in the G2/M phase. While arrest in the G2/M phase is commonly associated with disruption of microtubules within the cell, using confocal microscopy, it is determined that neither (−)-agelastatin A (1) nor (−)-agelastatin D (4) affects tubulin dynamics within cells.

An exemplary concise, stereocontrolled, and biosynthetically inspired synthetic strategy toward the agelastatin alkaloids, the development a versatile new synthetic methodology for azaheterocycle synthesis, and its successful implementation to the synthesis of all known (−)-agelastatins (1-6) and many derivatives were described. Key features of the exemplary syntheses include: 1) the early introduction of C13-bromide to suppress C7-enolization, 2) the development of a CuTC-mediated cross-coupling reaction between thioester and organostannane, 3) a new [4+1] annulation approach for the synthesis of imidazolones and related azaheterocycles, and 4) the validation of the bioinspired use of the imidazolone for an advanced stage C-ring formation, C4-C8 bond formation and introduction of three stereogenic centers. The efficiency of the provided synthetic sequence was highlighted by >1 gram batch preparation of (−)-agelastatin A (1). The generality of the provided synthesis allowed for the first side-by-side testing of all known agelastatin alkaloids for their ability to induce cell death in U-937 (lymphoma), HeLa, (cervical carcinoma), A549 (non-small cell lung carcinoma), BT549 (breast carcinoma), and IMR90 (immortalized lung fibroblasts) human cell lines. Provided compounds, such as (−)-Agelastatin A (1), exhibited the high potency toward blood cancer cells. Provided data show, for the first time, that compounds in provided compositions and methods, such as (−)-agelastatins A and D, induce apoptotic death of cancer cells and may not affect tubulin dynamics within cells. Applicants also show that these molecules may arrest cell growth in the G2/M phase. The present invention provides new methods and compositions for treating blood cancers; compounds of provided methods, such as (−)-agelastatins A (1), are highly potent against blood cancer cells (20-190 nM) without affecting normal red blood cells (>333 µM).

Details for all biological assays as well as experimental procedures were described below. For crystal structure of S25 (CIF): CCDC 955147.

Materials.

Commercial reagents and solvents were used as received with the following exceptions: dichloromethane, diethyl ether, tetrahydrofuran, acetonitrile, toluene, methanol, triethylamine, and pyridine were purchased from J.T. Baker (Cycletainer™) and were purified by the method of Grubbs et al. under positive argon pressure. Copper thiophene 2-carboxylate (CuTC), a tan colored solid, was purchased from Matrix Inc. and was used as received. The molarity of sec-butyllithium solutions were determined by titration using diphenylacetic acid as an indicator (average of three determinations).

Instrumentation.

Proton ($^1$H) and carbon ($^{13}$C) nuclear magnetic resonance spectra were recorded with Varian inverse probe 500 INOVA, Varian 500 INOVA, and Bruker AVANCE-400 NMR spectrometers. Proton nuclear magnetic resonance ($^1$H NMR) spectra are reported in parts per million on the δ scale and are referenced from the residual protium in the NMR solvent (CDCl$_3$: δ 7.24 (CHCl$_3$), CD$_3$OD: δ 3.31 (CHD$_2$OD). Data is reported as follows: chemical shift [multiplicity (s=singlet, d=doublet, t=triplet, q=quartet, st=sextet, sp=septet, m=multiplet, app=apparent, br=broad), coupling constant(s) in Hertz, integration, assignment. Carbon-13 nuclear magnetic resonance ($^{13}$C NMR) spectra are reported in parts per million on the δ scale and are referenced from the carbon resonances of the solvent (CDCl$_3$: δ 77.23, CD$_3$OD: δ 49.15). Data is reported as follows: chemical shift. Infrared data (IR) were obtained with a Perkin-Elmer 2000 FTIR and are reported as follows: [frequency of absorption (cm$^{-1}$), intensity of absorption (s=strong, m=medium, w=weak, br=broad)]. High-resolution mass spectrometric data (HRMS) were recorded on a Bruker APEXIV 4.7 t FT-ICR-MS spectrometer using electrospray ionization (ESI) source or direct analysis in real time (DART) ionization source.

Positional Numbering System.

In assigning the $^1$H and $^{13}$C NMR data of all intermediates en route to the total synthesis of (−)-1 through (−)-6 Applicants have employed a uniform numbering system consistent with that of the final targets.

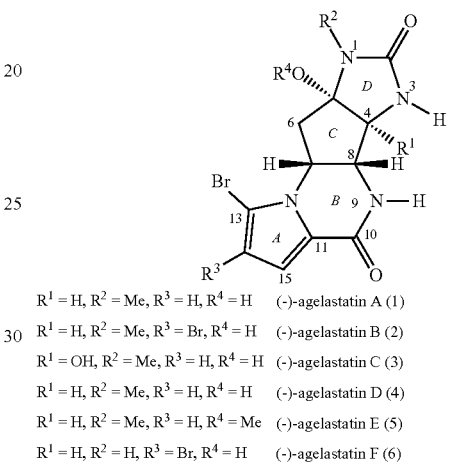

R$^1$ = H, R$^2$ = Me, R$^3$ = H, R$^4$ = H   (−)-agelastatin A (1)
R$^1$ = H, R$^2$ = Me, R$^3$ = Br, R$^4$ = H   (−)-agelastatin B (2)
R$^1$ = OH, R$^2$ = Me, R$^3$ = H, R$^4$ = H   (−)-agelastatin C (3)
R$^1$ = H, R$^2$ = Me, R$^3$ = H, R$^4$ = H   (−)-agelastatin D (4)
R$^1$ = H, R$^2$ = Me, R$^3$ = H, R$^4$ = Me   (−)-agelastatin E (5)
R$^1$ = H, R$^2$ = H, R$^3$ = Br, R$^4$ = H   (−)-agelastatin F (6)

Information for Key Compounds.

For complete experimental procedures and full characterization data for all (−)-agelastatin alkaloids A-F (1-6, respectively) in addition to the eight advanced derivatives (+)-39, (+)-44, (+)-48, (−)-50, (−)-51, (−)-52, and (+)-53 examined in the anticancer activity assays, please see the supporting information of M. Movassaghi, D. S. Siegel, S. Han, Chem. Sci., 2010, 1, 561, which is hereby incorporated by reference. For complete experimental procedures and full characterization data for the key compounds (+)-41, 47, (−)-54, 55, and (±)-56 discussed in the optimized route, please see the supporting information of M. Movassaghi, D. S. Siegel, S. Han, Chem. Sci., 2010, 1, 561. Complete experimental procedures and full characterization data for all new substrates and products reported in Table 3 were described herein.

Scheme S1. Optimized first-generation total synthesis of (±)-agelastatin A (1).

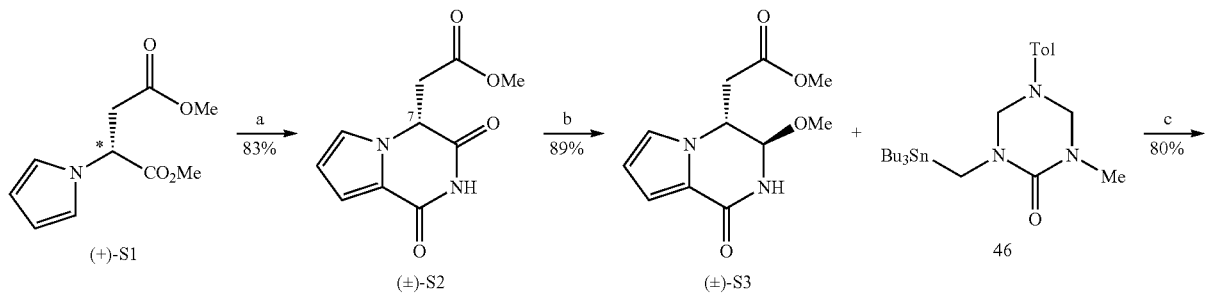

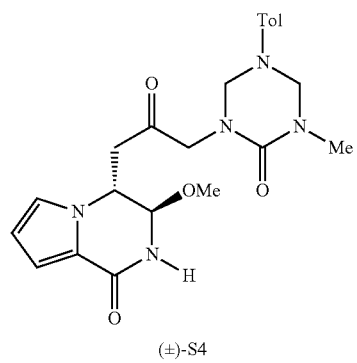

(±)-S4 d | 63%

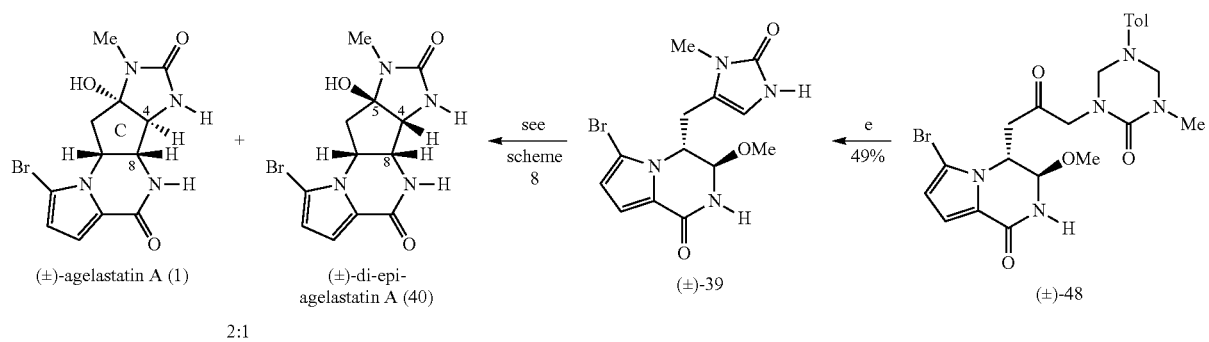

(±)-agelastatin A (1)       (±)-di-epi-agelastatin A (40)       (±)-39       (±)-48

2:1

Conditions: (a) ClSO₂NCO, MeCN, 0 → 23° C.; aq. NaHCO₃, 83%; (b) NaBH₄, MeOH, 0° C.; TsOH·H₂O, 23° C., 89%; (c) n-BuLi, THF, -78° C., 80%; (d) TABCO, EtOH, -25° C., 63%; (e) HCl (aq.), MeOH, 45° C., 49%.

After completing the first generation total synthesis of (±)-agelastatin A (1) using N—OMe substituted amide derivative (±)-34 (Scheme 8), Applicant could further streamline the synthesis by using lactam (±)-S3 (Scheme S1). Imide (±)-S2 was obtained in a single step from pyrrole (+)-S1 upon treatment with chlorosulfonylisocyanate followed by hydrolysis and in situ cyclization (83% yield). Imide (±)-S2 was converted to methyl ester (±)-S3 by reduction with sodium borohydride in methanol followed by addition of p-toluenesulfonic acid hydrate in one step (89% yield). Tin-lithium exchange of organostannane 46 and direct addition to methyl ester (±)-S3 gave the keto-triazone (±)-S4 in 80% yield. Treatment of ketone (±)-S4 with 2,4,4,6-tetrabromocyclohexa-2,5-dienone (TABCO) in ethanol at -20° C. provided C13-bromo ketone (±)-48 in 63% yield. Solvolysis of triazone (±)-48 in methanolic hydrogen chloride solution at 45° C. provided (±)-O-methyl-pre-agelastatin A (39, 49% yield). Following the conditions described in the text of this manuscript (Scheme 8), (±)-O-methyl-pre-agelastatin A (39) was converted to (±)-agelastatin A (1) and (±)-di-epi-agelastatin A (40).

Scheme S2. Second generation total synthesis of (-)-agelastatin A (1).

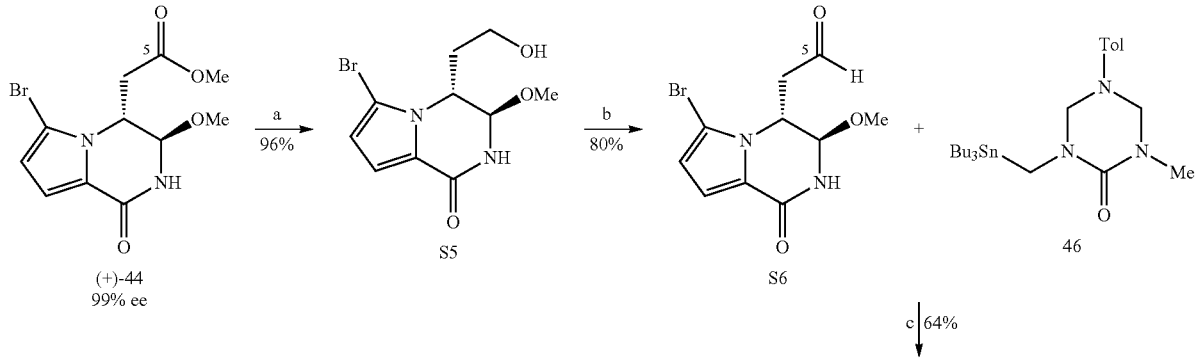

(+)-44
99% ee

S5

S6

46 c | 64%

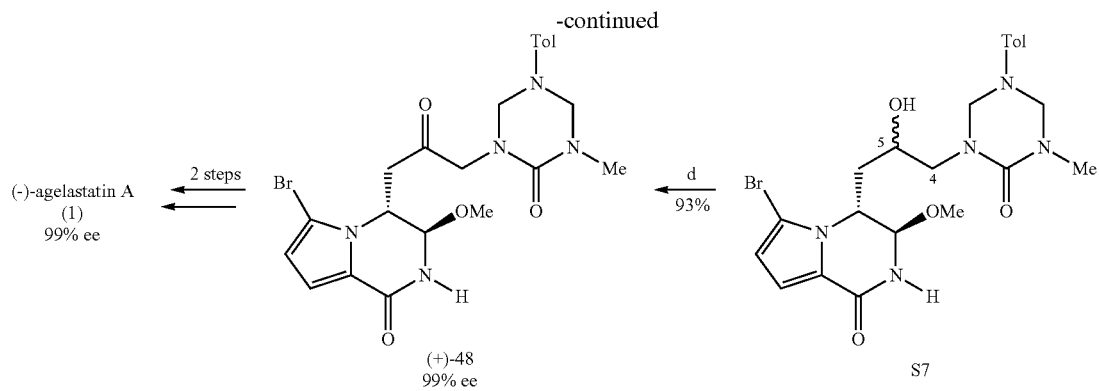

Conditions: (a) LiBH₄, THF, 23° C., 96%; (b) DMP, CH₂Cl₂, 0° C., 80%; (c) n-BuLi, THF, -78° C.; CeCl₃, THF, -78 → -45° C., 64%; (d) IBX, DMSO, 23° C., 93%.

Our first synthetic access to enantiomerically enriched (−)-agelastatin A (1) was realized via addition of organocerium triazone derivative to brominated bicyclic aldehyde S6 (Scheme S2). Methyl ester (+)-44 was reduced to alcohol S5 in the presence of lithium borohydride in THF in 96% yield (Scheme S2). The resulting alcohol S5 was oxidized to aldehyde S6 upon treatment with Dess-Martin periodinane in 80% yield. For the addition of metallated triazone to aldehyde S6, organocerium based triazone reagent was most effective, resulting in the secondary alcohols S7 in 64% yield as a mixture of diastereomers. Alcohol S7 was oxidized to keto triazone (+)-48 in the presence of IBX in DMSO at 23° C. in 93% yield and 99% ee. Keto triazone (+)-48 could be further converted to (−)-agelastatin A (1, 99% cc, Scheme 11).

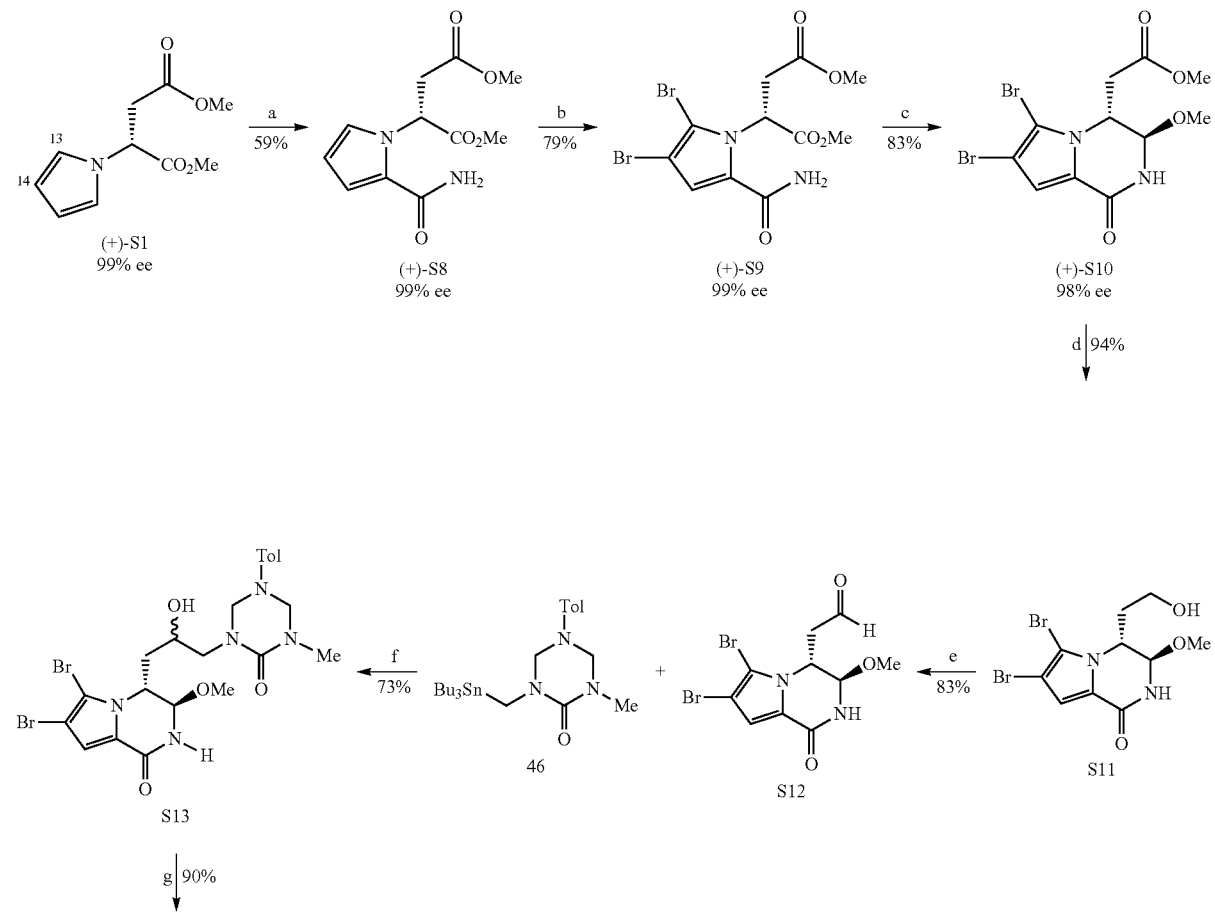

Scheme S3. Second-generation total synthesis of (−)-agelastatin B (2).

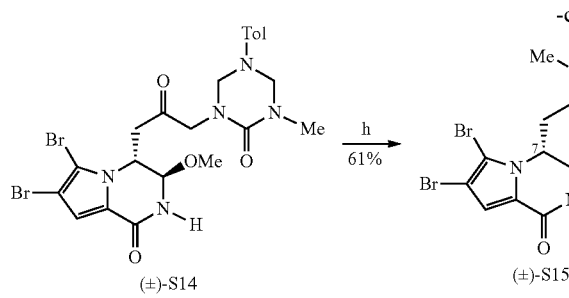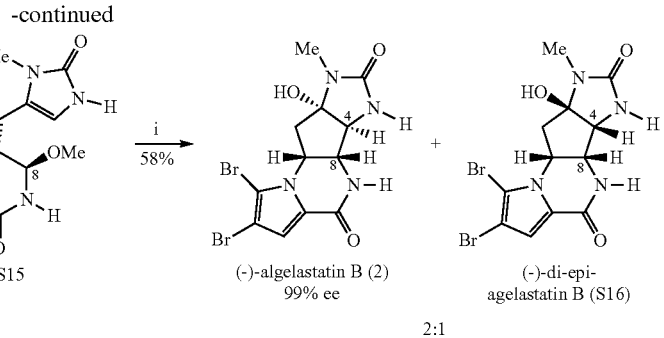

Conditions: (a) ClSO₂NCO, CH₃CN, 0° C; PBu₃, 59%; (b) TABCO, CH₃CN, 23° C., 79%; (c) NaBH₄, MeOH, 0° C.; TsOH·H₂O, 23° C., 89%; (d) LiBH₄, THF, 23° C., 94%; (e) DMP, CH₂Cl₂, 0° C., 83%; (f) n-BuLi, THF; CeCl₃, THF, -78 → -45° C., 73%; (g) IBX, DMSO, 23° C., 90%; (h) HCl (aq.), MeOH, 45° C., 61%; (i) TFA, H₂O, 95° C., 58% (2:1, (±)-2:(±)S16).

Pyrrole (+)-S1 was treated with chlorosulfonyl isocyanate followed by reductive quenching with tributylphosphine to provide amide (+)-S8 in 59% yield and 99% ee (Scheme S3). Treatment of amide (+)-S8 with 2.3 equivalent of 2,4,4,6-tetrabromo-2,5-cyclohexadienone afforded dibrominated amide (+)-S9 in 79% yield and 99% ee. Treatment of amide (+)-S9 with sodium borohydride in methanol followed by addition of p-toluenesulfonic acid hydrate gave methyl ester (+)-S10. Methyl ester (+)-S10 could be reduced to alcohol S11 in the presence of lithium borohydride in tetrahydrofuran solution in 94% yield. The resulting alcohol S11 was oxidized to aldehyde S12 upon treatment with Dess-Martin periodinane in 83% yield. For the addition of metallated triazone to aldehyde S12, organocerium reagent was most effective to give the secondary alcohols S13 in 73% yield. The resulting secondary alcohol S13 was oxidized to keto triazone (+)-S14 in the presence of IBX in DMSO at 23° C. in 90% yield. Solvolysis of triazone moiety in ketone (±)-S14 and condensative cyclization in methanolic hydrogen chloride at 45° C. provided (+)-O-methyl-pre-agelastatin B (S15, 61% yield). For the final step of the initial total synthesis of (−)-agelastatin B (2), exposure of imidazolones (+)-S15 in aqueous media containing TFA at 95° C. afforded the desired natural product (−)-agelastatin B (2, 99% ee) along with (−)-di-epi-agelastatin B (S16) in 58% yield (2:1, 2:S16).

Influence of the C13-Substituent on the Conformation of the C7-H

The minimized energy conformation of imide S17 and C13-brominated imide S18 showed a difference in their H7-C7-C8-O8 dihedral angles. While the H7-C7-C8-O8 dihedral angle of imide S17 was calculated to be 76°, that of C13-brominated imide S18 was calculated to be 56° (FIG. 5). Without the intention to be bound by theory, the smaller dihedral angle of imide S18 can be rationalized based on the allylic strain between the C13-bromine and C6-methylene, which forces the alkyl group at C7 to adopt a conformation almost orthangonal with respect to the B-ring.

The H7-C7-C8-H8 dihedral angle of acyliminium ion S19 was calculated to be 53° while that of C13 brominated acyliminium ion 8 was calculated to be 31° (Figure S2). Thus the C7 proton of acyliminium ion 8 would be less prone to deprotonation as the overlap of C7-H7 σ orbital to C8-N9 π* orbital would be less than that of acyliminium ion S19.

Rate of C4-Deuterium Incorporation in (+)-O-methyl-pre-agelastatins A (39) and D (53)

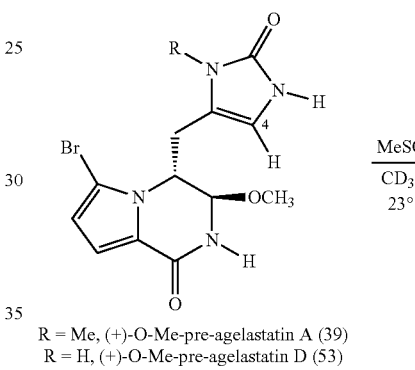

R = Me, (+)-O-Me-pre-agelastatin A (39)
R = H, (+)-O-Me-pre-agelastatin D (53)

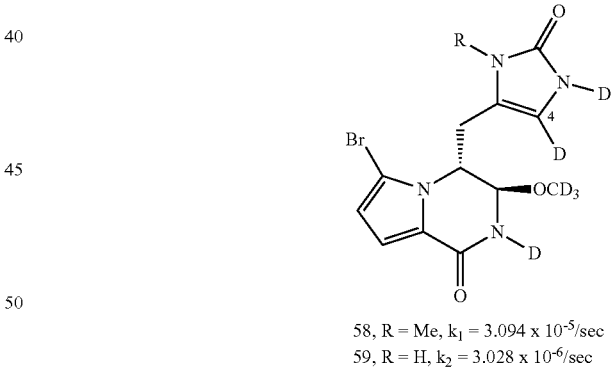

58, R = Me, k₁ = 3.094 x 10⁻⁵/sec
59, R = H, k₂ = 3.028 x 10⁻⁶/sec (+)-O-methyl-pre-agelastatin A (39, 4.0 mg, 11 μmol, 1 equiv) and (+)-O-methyl-pre-agelastatin D (53, 4.0 mg, 11 μmol, 1 equiv) were separately dissolved in methanol-d₄ (0.78 mL) and the ¹H NMR spectra were recorded at 23° C. for the reference at t=0. The hydrogen-deuterium exchange experiment was initiated by adding methanesulfonic acid (15 μL, 0.23 mmol, 21 equiv) into the samples. The ¹H NMR spectra were then recorded at appropriate time intervals, and the amount of deuterium incorporation at C4 was recorded. (First order kinetics to the substrate was assumed. Hence −d[A]/dt=k[A], where [A] is the substrate concentration).

TABLE 5

Deuterium incorporation at C4 of (+)-O-methyl-pre-agelastatins A (39) and D (53).

| Time (h) | 0 | 0.1 | 0.5 | 0.8 | 2.0 | 4.0 | 13.5 | 18.0 | 20.5 | 26.0 |
|---|---|---|---|---|---|---|---|---|---|---|
| d-incoporation at C4 of 39 (%) | 0 | 5.0 | 10.3 | 11.4 | 22.6 | 40.1 | 80.0 | 86.6 | 91.0 | 94.3 |
| d-incorporation at C4 of 53 (%) | 0 | 0 | 0 | 1.5 | 3.3 | 6.1 | 14.6 | 16.9 | 19.7 | 25.7 |
| [39] (mol/L) | 0.0141 | 0.0134 | 0.0126 | 0.0125 | 0.011 | 0.0084 | 0.0028 | 0.0019 | 0.0012 | 0.0008 |
| [53] (mol/L) | 0.0141 | 0.0141 | 0.0141 | 0.013889 | 0.01363 | 0.0132 | 0.0120 | 0.0117 | 0.0113 | 0.0104 |
| ln[39] | −4.2615 | −4.3128 | −4.3702 | −4.3826 | −4.5177 | −4.7740 | −5.8710 | −6.2714 | −6.6695 | −7.1262 |
| ln[53] | −4.2615 | −4.2616 | −4.262 | −4.277 | −4.3 | −4.325 | −4.4194 | −4.447 | −4.4809 | −4.5586 |

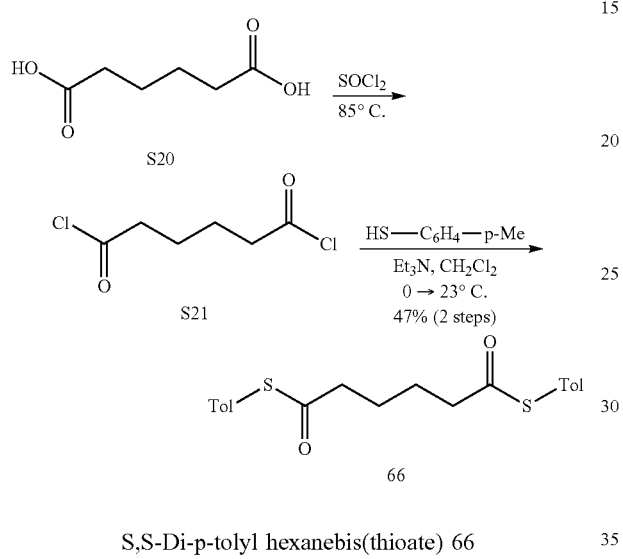

S,S-Di-p-tolyl hexanebis(thioate) 66

To a flask charged with adipic acid (S20, 4.0 g, 27 mmol, 1 equiv) was added thionyl chloride (5.0 mL, 68 mmol, 2.5 equiv) and the reaction flask was equipped with a reflux condensor and heated to 85° C. (The exhaust gases were passed through a 5 N aqueous potassium hydroxide solution). After 1.5 h, the reaction mixture was allowed to cool to 23° C. and concentrated under reduced pressure to afford acyl chloride S21 as a viscous oil. The resulting crude material was dissolved in dichloromethane (10 mL) and the resulting mixture was transferred to a solution of 4-methylbenzenethiol (7.3 g, 57 mmol, 2.1 equiv) in dichloromethane (30 mL) via cannula at 0° C. The reaction mixture was allowed to gently warm to 23° C. After 2 h, triethylamine (2.0 mL, 14 mmol, 0.52 equiv) was added to the reaction mixture. After 25 min, more triethylamine (3.0 mL, 22 mmol, 0.79 equiv) was added to the reaction mixture. After 16.5 h, the reaction mixture was diluted with dichloromethane (210 mL) and saturated aqueous sodium bicarbonate solution (250 mL) and the layers were separated. The aqueous layer was extracted with dichloromethane (250 mL), and the combined organic layers were dried over anhydrous sodium sulfate, were filtered, and were concentrated under reduced pressure. The residue was purified by flash column chromatography (silica gel: diam. 9.0 cm, ht. 12 cm; eluent: 11% ethyl acetate in hexanes) to afford thioester 66 (4.6 g, 47%) as a white solid. $^1$H NMR (500 MHz, CDCl$_3$, 21° C.): δ 7.27 (app-d, J=8.1 Hz, 4H), 7.20 (app-d, J=7.9 Hz, 4H), 2.67-2.64 (m, 4H), 2.36 (s, 6H), 1.78-1.75 (m, 4H). $^{13}$C NMR (125.8 MHz, CDCl$_3$, 21° C.): δ 197.7, 139.9, 134.6, 130.2, 124.3, 43.2, 25.0, 21.5. FTIR (neat) cm$^{-1}$: 2929 (m), 1687 (s), 1493 (m), 1034 (m), 813 (s). HRMS (ESI) (m/z): calc'd for C$_{20}$H$_{22}$NaO$_2$S$_2$, [M+Na]$^+$: 381.0959, found: 381.0965. TLC (17% ethyl acetate in hexanes), Rf: 0.53 (CAM, UV).

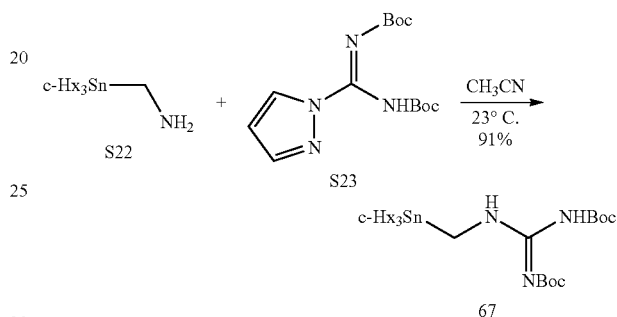

1-((Tricyclohexylstannyl)methyl)-N,N'-di-tert-butyl-carbamoylguanidine (67)

Stannylamine S22 (910 mg, 2.28 mmol, 1 equiv) was dissolved in acetonitrile (60 mL), and (E)-tert-butyl(((tert-butoxycarbonyl)imino)(1H-pyrazol-1-yl)methyl)carbamate (S23, 1.09 g, 3.43 mmol, 1.50 equiv) was added sequentially at 23° C. After 11 h, the resulting mixture was concentrated under reduced pressure, and the crude residue, adsorbed onto silica gel, was purified by flash column chromatography (silica gel: diam. 4.0 cm, ht. 12 cm; eluent: 3.3% ethyl acetate in hexanes) to afford tricyclohexyltin reagent 67 (1.3 g, 91%) as a white solid. $^1$H NMR (500 MHz, CDCl$_3$, 21° C.): δ 11.39 (s, 1H), 8.44 (t, J=5.1 Hz, 1H), 3.08 (d, J=5.6 Hz, 2H), 1.84 (t, J=4.4 Hz, 6H), 1.62 (d, J=9.6 Hz, 9H), 1.53 (t, J=7.1 Hz, 9H), 1.48 (s, 9H), 1.45 (s, 9H), 1.28-1.21 (m, 9H). $^{13}$C NMR (125.8 MHz, CDCl$_3$, 21° C.): δ 163.9, 155.8, 153.6, 82.9, 78.9, 32.4, 29.5, 28.6, 28.2, 27.5, 27.4, 24.1. FTIR (neat) cm$^{-1}$: 3327 (s), 2917 (s), 2846 (s), 1717 (s), 1642 (s), 1575 (s), 1409 (s), 1337 (s), 1157 (s), 1052 (s), 909 (m), 735 (m). HRMS (ESI) (m/z): calc'd for C$_{30}$H$_{56}$N$_3$O$_4$Sn, [M+H]$^+$: 642.3293, found: 642.3290. TLC (10% ethyl acetate in hexanes), Rf: 0.56 (CAM).

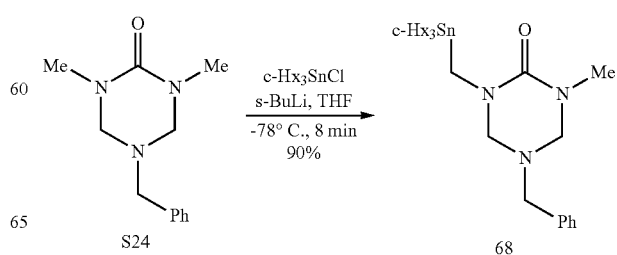

5-Benzyl-1-methyl-3-((tricyclohexylstannyl)methyl)-1,3,5-triazinan-2-one (68)

To a solution of triazone S24 (1.5 g, 6.8 mmol, 2.0 equiv) in tetrahydrofuran (40 mL) at −78° C. was added sec-butyllithium (1.4 M in cyclohexane, 4.9 mL, 6.8 mmol, 2.0 equiv) via syringe to result in an orange homogeneous solution. After 5 min, a solution of tricyclohexyltin chloride (1.42 g, 3.42 mmol, 1 equiv) in tetrahydrofuran (10 mL) at −78° C. was transferred to the resulting bright orange mixture via cannula over a 3 min period. After 8 min, saturated aqueous ammonium chloride solution (5 mL) was added via syringe. The resulting mixture was partitioned between dichloromethane (250 mL) and water (200 mL). The layers were separated, the aqueous layer was extracted with dichloromethane (250 mL), and the combined organic layers were dried over anhydrous sodium sulfate, were filtered, and were concentrated under reduced pressure. The crude residue was purified by flash column chromatography (silica gel: diam. 5 cm, ht. 10 cm; eluent: hexanes then 17% ethyl acetate in hexanes) to afford stannyltriazone 68 (1.8 g, 90%) as a white solid. $^1$H NMR (500 MHz, CDCl$_3$, 21° C.): δ 7.34-7.24 (m, 5H), 4.10 (s, 2H), 4.03 (s, 2H), 3.90 (s, 2H), 2.81 (s, 3H), 2.75 (s, 2H), 1.84 (dd, J=12.5, 2.0 Hz, 3H), 1.63 (d, J=8.9 Hz, 12H), 1.55-1.39 (m, 6H), 1.31-1.17 (m, 12H). $^{13}$C NMR (125.8 MHz, CDCl$_3$, 21° C.): δ 156.1, 137.9, 129.1, 128.7, 127.7, 69.7, 67.6, 55.8, 32.9, 32.4, 29.5, 29.0, 27.9, 27.4. FTIR (neat) cm$^{-1}$: 2917 (s), 2229 (m), 1634 (s), 1519 (s), 1445 (s), 1408 (m), 1297 (s), 1144 (m), 908 (s), 735 (s). HRMS (ESI) (m/z): calc'd for C$_{30}$H$_{50}$N$_3$OSn, [M+H]$^+$: 588.2987, found: 588.2976. TLC (17% ethyl acetate in hexanes), Rf: 0.32 (CAM, UV).

equiv), triazone 47 (36.0 mg, 61.4 μmol, 1.20 equiv), and copper(I)-thiophene-2-carboxylate (CuTC, 15.3 mg, 76.8 μmol, 1.50 equiv) at 23° C. under an argon atmosphere, and the reaction mixture was heated to 50° C. After 1 h, the reaction mixture was allowed to cool to 23° C. and was filtered through a plug of celite with ethyl acetate washings (3×1 mL). The resulting mixture was partitioned between ethyl acetate (20 mL) and saturated ammonium chloride aqueous solution (20 mL). The aqueous layer was extracted with ethyl acetate (2×20 mL), and the combined organic layers were dried over anhydrous sodium sulfate, and were concentrated under reduced pressure. The crude residue was purified by flash column chromatography (silica gel: diam. 2 cm, ht. 10 cm; eluent: 25% ethyl acetate in hexanes) to afford ketotriazone 71 (16 mg, 95%) as a colorless oil. $^1$H NMR (500 MHz, CDCl$_3$, 21° C.): δ 7.08 (d, J=8.0 Hz, 2H), 6.94 (d, J=8.6 Hz, 2H), 4.69 (s, 2H), 4.66 (s, 2H), 4.09 (s, 2H), 2.88 (s, 3H), 2.32 (tt, J=11.4, 3.4 Hz, 1H), 2.27 (s, 3H), 1.80 (dd, J=13.3, 2.2 Hz, 2H), 1.76-1.72 (m, 2H), 1.66-1.60 (m, 2H), 1.32 (ddd, J=15.2, 12.4, 3.1 Hz, 2H), 1.25-1.15 (m, 2H). $^{13}$C NMR (125.8 MHz, CDCl$_3$, 21° C.): δ 210.4, 156.1, 146.0, 132.6, 130.1, 119.8, 67.4, 67.4, 53.5, 48.2, 32.4, 28.4, 25.9, 25.7, 20.8. FTIR (neat) cm$^{-1}$: 2929 (s), 2855 (m), 1720 (m), 1647 (s), 1514 (s), 1300 (m), 1198 (m), 829 (m). HRMS (ESI) (m/z): calc'd for C$_{19}$H$_{26}$N$_3$O$_2$, [M−H]$^-$: 328.2025, found: 328.2030. TLC (ethyl acetate), Rf: 0.40 (CAM).

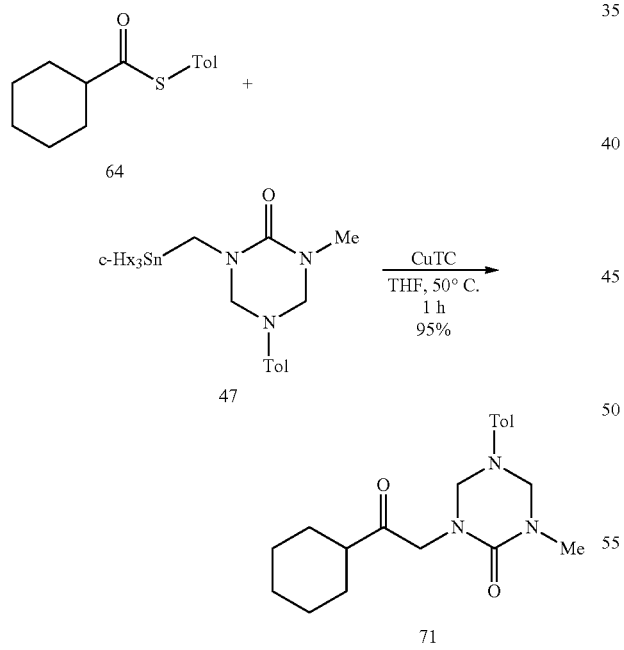

1-(2-Cyclohexyl-2-oxoethyl)-3-methyl-5-(p-tolyl)-1,3,5-triazinan-2-one (71)

Anhydrous tetrahydrofuran (1.0 mL, degassed thoroughly by passage of a stream of argon) was added via syringe to a flask charged with thioester 64 (12.0 mg, 51.2 μmol, 1

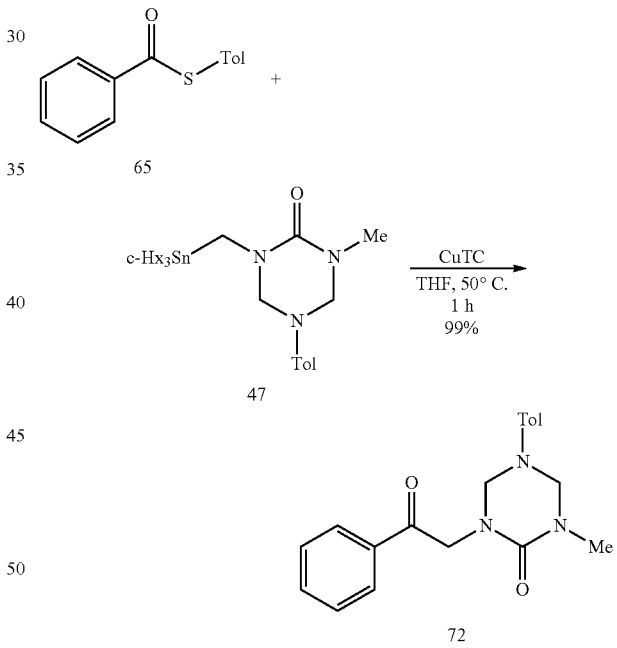

1-Methyl-3-(2-oxo-2-phenylethyl)-5-(p-tolyl)-1,3,5-triazinan-2-one (72)

Anhydrous tetrahydrofuran (1.1 mL, degassed thoroughly by passage of a stream of argon) was added via syringe to a flask charged with thioester 65 (12.0 mg, 52.6 μmol, 1 equiv), triazone 47 (37.0 mg, 63.1 μmol, 1.20 equiv), and copper(I)-thiophene-2-carboxylate (CuTC, 15.7 mg, 78.8 μmol, 1.50 equiv) at 23° C. under an argon atmosphere, and the reaction mixture was heated to 50° C. After 1 h, the reaction mixture was allowed to cool to 23° C. and was filtered through a plug of celite with ethyl acetate washings (3×1 mL). The resulting mixture was partitioned between ethyl acetate (20 mL) and saturated ammonium chloride aqueous solution (20 mL). The aqueous layer was extracted with ethyl acetate (2×20 mL), and the combined organic layers were dried over anhydrous sodium sulfate, were filtered, and were concentrated under reduced pressure. The crude residue was purified by flash column chromatography (silica gel: diam. 2 cm, ht. 10 cm; eluent: 25% ethyl acetate in hexanes) to afford ketotriazone 72 (17 mg, 99%) as a colorless oil. $^1$H NMR (500 MHz, CDCl$_3$, 21° C.): δ 7.92 (dd, J=8.4, 1.2 Hz, 2H), 7.55 (tt, J=7.4, 1.2 Hz, 1H), 7.42 (app-t, J=7.8 Hz, 2H), 7.07 (d, J=8.0 Hz, 2H), 6.95 (app-d, J=8.5 Hz, 2H), 4.80 (s, 2H), 4.73 (s, 2H), 4.72 (s, 2H), 2.92 (s, 3H), 2.28 (s, 3H). $^{13}$C NMR (125.8 MHz, CDCl$_3$, 21° C.): δ 196.1, 156.1, 145.9, 135.2, 133.8, 132.6, 130.1, 128.9, 128.3, 119.8, 67.4, 67.3, 52.5, 32.5, 20.3. FTIR (neat) cm$^{-1}$: 2888 (m), 1694 (m), 1638 (s), 1513 (s), 1288 (m), 1219 (m), 750 (m). HRMS (ESI) (m/z): calc'd for C$_{19}$H$_{20}$N$_3$O$_2$, [M–H]$^-$: 322.1556, found: 322.1562. TLC (ethyl acetate), Rf: 0.46 (CAM, UV).

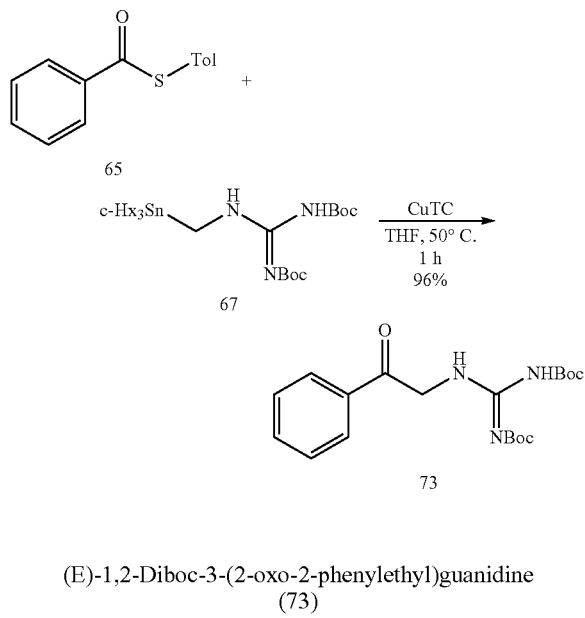

(E)-1,2-Diboc-3-(2-oxo-2-phenylethyl)guanidine (73)

Anhydrous tetrahydrofuran (6.0 mL, degassed thoroughly by passage of a stream of argon) was added via syringe to a flask charged with thioester 65 (36.6 mg, 0.160 mmol, 1 equiv), stannylguanidine 67 (113 mg, 0.176 mmol, 1.10 equiv), and copper(I)-thiophene-2-carboxylate (CuTC, 32.8 mg, 0.165 mmol, 1.03 equiv) at 23° C. under an argon atmosphere, and the reaction mixture was heated to 50° C. After 1 h, the reaction mixture was allowed to cool to 23° C., and 5% ammonium hydroxide aqueous solution (15 mL) was added to the reaction mixture. The resulting mixture was extracted with dichloromethane (2×15 mL), and the combined organic layers were dried over anhydrous sodium sulfate, were filtered, and were concentrated under reduced pressure. The crude residue was purified by flash column chromatography (silica gel: diam. 2.5 cm, ht. 15 cm; eluent: 11% ethyl acetate in hexanes) to afford ketoguanidine 73 (58 mg, 96%). $^1$H NMR (500 MHz, CDCl$_3$, 21° C.): δ 11.5 (s, 1H, NH), 9.41 (s, 1H, NH), 7.98 (dd, J=8.5, 1.2 Hz, 2H), 7.59 (tt, J=7.4, 1.3 Hz, 1H), 7.46 (app-t, J=7.7 Hz, 1H), 4.92 (d, J=4.1 Hz, 2H), 1.51 (s, 9H), 1.50 (s, 9H). $^{13}$C NMR (125.8 MHz, CDCl$_3$, 21° C.): δ 193.4, 163.5, 156.1, 153.1, 134.4, 134.3, 129.1, 128.3, 83.5, 79.8, 48.4, 28.4, 28.3. FTIR (neat) cm$^{-1}$: 3319 (m), 2980 (m), 1727 (s), 1697 (m), 1642 (s), 1618 (s), 1409 (m), 1308 (s), 1148 (s), 734 (m). HRMS (ESI) (m/z): calc'd for C$_{19}$H$_{28}$N$_3$O$_5$, [M+H]$^+$: 378.2029, found: 378.2035. TLC (20% ethyl acetate in hexanes), Rf: 0.44 (CAM, UV).

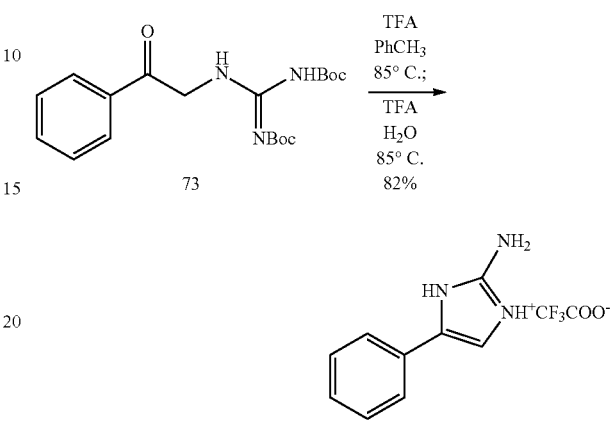

2-Amino-5-phenyl-1H-imidazol-3-ium 2,2,2-trifluoroacetate (74)

To a flask charged with ketoguanidine 73 (57.9 mg, 0.153 mmol, 1 equiv) was added toluene (4 mL) and trifluoroacetic acid (120 μL, 1.53 mmol, 10.0 equiv) via syringe and the reaction mixture was heated to 85° C. After 13.5 h, the reaction mixture was allowed to cool to 23° C. and was concentrated under reduced pressure. Water (2 mL) and trifluoroacetic acid (120 μL, 1.53 mmol, 10.0 equiv) were added via syringe to the residue and the resulting mixture was heated to 85° C. After 1.5 h, the reaction mixture was allowed to cool to 23° C. and was concentrated under reduced pressure to give 2-aminoimidazole 74 (34 mg, 82%) as a pale yellow solid. $^1$H NMR (500 MHz, CD$_3$OD, 21° C.): δ 7.56 (app-d, J=7.2 Hz, 2H), 7.43 (app-t, J=7.7 Hz, 2H), 7.34 (app-tt, J=7.4, 1.2 Hz, 1H), 7.13 (s, 1H). $^{13}$C NMR (125.8 MHz, CD$_3$OD, 21° C.): δ 163.1, 149.7, 130.3, 129.7, 129.2, 129.1, 125.6, 109.9, 101.4. FTIR (neat) cm$^{-1}$: 3182 (br-s), 1682 (br-s), 1204 (s), 1139 (s), 842 (m). HRMS (ESI) (m/z): calc'd for C$_9$H$_{10}$N$_3$, [M+H]$^+$: 160.0869, found: 160.0867.

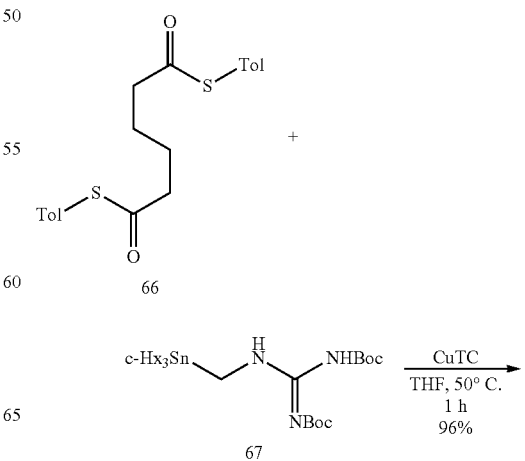

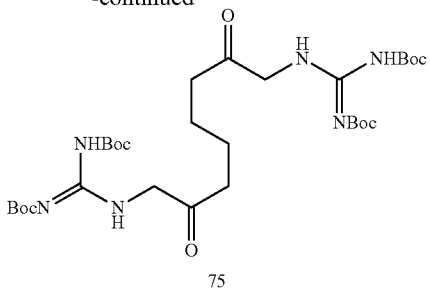

(E,E)-1,1'-(2,7-Dioxooctane-1,8-diyl)bis(2',3-di-bocguanidine) (75)

Anhydrous tetrahydrofuran (34 mL, degassed thoroughly by passage of a stream of argon) was added via syringe to a flask charged with thioester 66 (300 mg, 0.836 mmol, 1 equiv), stannylguanidine 67 (1.34 g, 2.09 mmol, 2.50 equiv), and copper(I)-thiophene-2-carboxylate (CuTC, 374 mg, 1.88 mmol, 2.25 equiv) at 23° C. under an argon atmosphere, and the reaction mixture was heated to 50° C. After 1 h, the reaction mixture was allowed to cool to 23° C. The resulting mixture was partitioned between dichloromethane (145 mL) and 5% ammonium hydroxide aqueous solution (145 mL). The aqueous layer was extracted with dichloromethane (3×145 mL), and the combined organic layers were dried over anhydrous sodium sulfate, were filtered, and were concentrated under reduced pressure. The crude residue was purified by flash column chromatography (silica gel: diam. 4 cm, ht. 10 cm; eluent: 11% ethyl acetate in hexanes) to afford ketoguanidine 75 (549 mg, 100%) as a pale yellow solid. $^1$H NMR (500 MHz, CDCl$_3$, 21° C.): δ 11.37 (s, 2H), 9.02 (s, 2H), 4.28 (d, J=4.3 Hz, 4H), 2.42 (app-s, 4H), 1.60 (t, J=3.1 Hz, 4H), 1.47 (s, 9H), 1.46 (s, 9H). $^{13}$C NMR (125.8 MHz, CDCl$_3$, 21° C.): δ 203.9, 163.4, 155.9, 153.0, 83.5, 79.7, 51.0, 39.9, 28.4, 28.2, 23.1. FTIR (neat) cm$^{-1}$: 3319 (br-m), 2980 (m), 2253 (w), 1726 (s), 1643 (s), 1618 (s), 1408 (m), 1309 (s), 1151 (s), 1058 (m), 734 (m). HRMS (ESI) (m/z): calc'd for C$_{30}$H$_{53}$N$_6$O$_{10}$, [M+H]$^+$: 657.3823, found: 657.3801. TLC (50% ethyl acetate in hexanes), Rf: 0.44 (CAM).

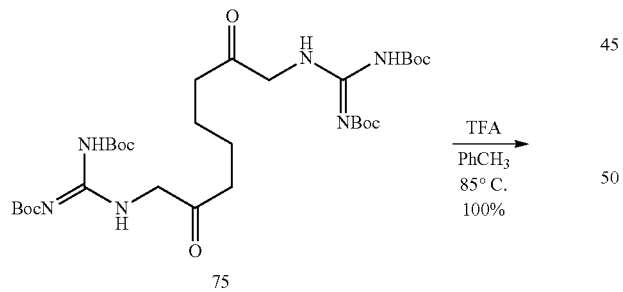

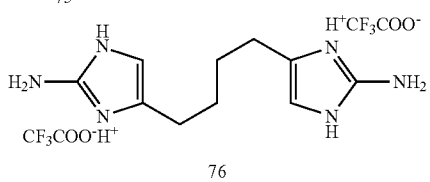

4,4'-(Butane-1,4-diyl)bis(2-amino-1H-imidazol-3-ium) 2,2,2-trifluoroacetate (76)

Toluene (40 mL) and trifluoroacetic acid (650 µL, 8.36 mmol, 10.0 equiv) were added via syringe to a flask charged with ketoguanidine 75 (549 mg, 0.836 mmol, 1 equiv) and the resulting mixture was heated to 75° C. After 16 h, the reaction mixture was allowed to cool to 23° C. and was concentrated under reduced pressure. Water (20 mL) and trifluoroacetic acid (650 µL, 8.36 mmol, 10.0 equiv) were added via syringe to the residue and the resulting mixture was heated to 100° C. After 45 h, the reaction mixture was allowed to cool to 23° C. and was concentrated under reduced pressure to give 2-aminoimidazole 76 (375 mg, 100%) as a brown solid. $^1$H NMR (500 MHz, CD$_3$OD, 21° C.): δ 6.49 (s, 2H), 2.53 (app-t, J=6.5 Hz, 4H), 1.65 (app-t, J=7.1 Hz, 4H). $^{13}$C NMR (125.8 MHz, CD$_3$OD, 21° C.): δ 162.6, 148.8, 128.8, 109.8, 101.4, 28.7, 25.2. FTIR (neat) cm$^{-1}$: 3179 (br-s), 2361 (w), 1702 (s), 1442 (m), 1205 (s), 1134 (s), 845 (m), 723 (m). HRMS (ESI) (m/z): calc'd for C$_{10}$H$_{17}$N$_6$, [M+H]$^+$: 221.1509, found: 221.1512.

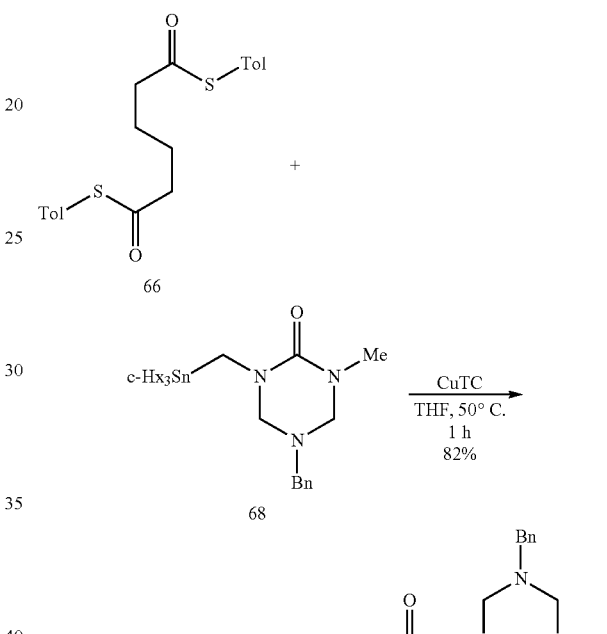

1,8-Bis(5-benzyl-3-methyl-2-oxo-1,3,5-triazinan-1-yl)octane-2,7-dione (77)

Anhydrous tetrahydrofuran (8.0 mL, degassed thoroughly by passage of a stream of argon) was added via syringe to a flask charged with thioester 66 (70.9 mg, 0.198 mmol, 1 equiv), triazone 68 (290 mg, 0.494 mmol, 2.50 equiv), and copper(I)-thiophene-2-carboxylate (CuTC, 88.4 mg, 0.448 mmol, 2.25 equiv) at 23° C. under an argon atmosphere, and the reaction mixture was heated to 50° C. After 1.5 h, the reaction mixture was allowed to cool to 23° C. The resulting mixture was partitioned between dichloromethane (30 mL) and 5% ammonium hydroxide aqueous solution (30 mL). The aqueous layer was extracted with dichloromethane (30 mL), and the combined organic layers were dried over anhydrous sodium sulfate, were filtered, and were concentrated under reduced pressure. The crude residue was purified by flash column chromatography (silica gel: diam. 3 cm, ht. 11 cm; eluent: 24% chloroform, 5% methanol, and 0.6% ammonium hydroxide in dichloromethane) to afford ketotriazone 77 (89 mg, 82%) as a colorless oil. $^1$H NMR (500 MHz, CDCl$_3$, 21° C.): δ 7.33-7.26 (m, 10H), 4.19 (s, 4H), 4.15 (s, 4H), 4.00 (s, 4H), 3.99 (s, 4H), 2.84 (s, 6H), 2.40 (t, J=6.9 Hz, 4H), 1.57 (q, J=3.3, 4H). $^{13}$C NMR (100.6 MHz, CDCl$_3$, 21° C.): δ 206.9, 155.7, 137.8, 129.3, 128.8, 127.8, 67.8, 67.5, 55.6, 54.6, 39.6, 32.6, 23.0. FTIR (neat) cm$^{-1}$: 3442 (br-s), 2929 (m), 2237 (w), 1717 (m), 1635 (m), 1506 (m), 1266 (s), 739 (s). HRMS (ESI) (m/z): calc'd for C$_{30}$H$_{41}$N$_6$O$_4$, [M+H]$^+$: 549.3189, found: 549.3183. TLC (24% chloroform, 5.4% methanol, and 0.6% ammonium hydroxide in dichloromethane), Rf: 0.27 (CAM, UV).

General Reagents and Methods for Biological Assays.

For biological assays, propidium iodide, phenazine methosulfate, and monoclonal anti-α-tubulin-FITC antibody were purchased from Sigma-Aldrich. The 3-(4,5-dimethylthiazol-2-yl)-5-(3-carboxymethoxyphenyl)-2-(4-sulfophenyl)-2H-tetrazolium salt was obtained from Promega. Annexin-V FITC conjugate was purchased from Invitrogen. All Western antibodies were obtained from Cell Signaling. Optical densities were recorded on a Spectramax Plus 384 (Molecular Devices, Sunnyvale, Calif.). Flow cytometry was performed on a BD Biociences LSR II (San Jose, Calif.) and the data was analyzed as described using FACSDiva software (San Jose, Calif.).

Cell Culture Information.

Cells were grown in media supplemented with fetal bovine serum (FBS) and antibiotics (100 μg/mL penicillin and 100 U/mL streptomycin). Specifically, experiments were performed using the following cell lines and media compositions: U-937, HeLa, A549, BT549, CEM, Daudi, and Jurkat (RPMI-1640+10% FBS), CA46 (DMEM+10% FBS), HL-60 (IMDM+10% FBS), and IMR90 (EMEM+10% FBS). Cells were incubated at 37° C. in a 5% CO$_2$, 95% humidity atmosphere.

IC$_{50}$ Value Determination for Adherent Cells Using Sulforhodamine B (SRB).

Adherent cells (HeLa, A549, BT549, and IMR90) were added into 96-well plates (5,000 cells/well for HeLa cell line; 2,000 cells/well for A549, BT549, and IMR90 cell lines) in 100 μL media and were allowed to adhere for 2-3 hours. Compounds were solubilized in DMSO as 100× stocks, added directly to the cells (100 μL final volume), and tested over a range of concentrations (1 nM to 10 μM) in triplicate (1% DMSO final) on a half-log scale. DMSO and cell-free wells served as the live and dead control, respectively. After 48 h of continuous exposure, the plates were evaluated using the SRB colorimetric assay as described previously (V. Vichai, K. Kirtikara, Nature Prot., 2006, 1, 1112). Briefly, media was removed from the plate, and cells were fixed by the addition of 100 μL cold 10% trichloroacetic acid in water. After incubating at 4° C. for 1 h, the plates were washed in water and allowed to dry. Sulforhordamine B was added as a 0.057% solution in 1% acetic acid (100 μL), and the plates were incubated at room temperature for 30 min, washed in 1% acetic acid, and allowed to dry. The dye was solubilized by adding 10 mM Tris base solution (pH 10.5, 200 μL) and incubating at room temperature for 30 min Plates were read at λ=510 nm. IC$_{50}$ values were determined from three or more independent experiments using TableCurve (San Jose, Calif.).

IC$_{50}$ Value Determination for Non-Adherent Cells Using MTS.

In a 96-well plate, compounds were pre-added as DMSO stocks (1% final) in triplicate to achieve final concentrations of 1 nM to 10 μM on a half log scale. DMSO and cell-free wells served as the live and dead control, respectively. Suspension cells (U-937, CEM, CA46, Daudi, HL-60, and Jurkat; 10,000 cells/well) cells were distributed in 100 μL media to the compound-containing plate. After 48 h, cell viability was assessed by adding 20 μL of a PMS/MTS solution (A. H. Cory, T. C. Owen, J. A. Barltrop, J. G. Cory, Cancer Commun., 1991, 3, 207) to each well, allowing the dye to develop at 37° C. until the live control had processed MTS, and reading the absorbance at λ=490 nm. IC$_{50}$ values were determined from three or more independent experiments using TableCurve (San Jose, Calif.).

Hemolysis Assay using Human Erythrocytes.

To prepare the erythrocytes, 0.1 mL of human blood was centrifuged (10,000 g, 2 min). The pellet was washed three times with saline (0.9% NaCl) via gentle resuspension and centrifugation (10,000 g, 2 min). Following the final wash, the erythrocytes were resuspended in 0.4 mL red blood cell (RBC) buffer (10 mM Na$_2$HPO$_4$, 150 mM NaCl, 1 mM MgCl$_2$, pH 7.4).

DMSO stocks of compounds were added to 0.5 mL tubes in singlicate (1 μL, 3.3% DMSO final). The stocks were diluted with 19 μL RBC buffer. Positive control tubes contained DMSO in water, and negative control tubes contained DMSO in RBC buffer. A suspension of washed erythrocytes (10 μL) was added to each tube, and samples were incubated at 37° C. for 2 hours. Samples were centrifuged (10,000 g, 2 min), and the supernatant was transferred to a clear, sterile 384-well plate. The absorbance of the supernatants was measured at λ=540 nm, and percent hemolysis was calculated relative to the average absorbance values measured for the controls.

Apoptosis in U-937 Cells with Annexin V-FITC and Propidium Iodide (AnnV/PI).

DMSO stocks of compounds were added to a 24-well plate in singlicate (0.2% DMSO final). After compound addition, 0.5 mL of a U-937 cell suspension (250,000 cells/mL) was added and allowed to incubate for 21 hours. Following treatment, the cell suspensions were transferred to flow cytometry tubes and pelleted (500 g, 3 min). The media was removed by aspiration, and cells were resuspended in 200 μL AnnV binding buffer (10 mM HEPES, pH 7.4, 140 mM NaCl, 2.5 mM CaCl$_2$) with 5 μg/mL PI and 1:90 dilution of AnnV. Samples were analyzed using flow cytometry.

Cell Cycle Arrest in Thymidine-Synchronized U-937 Cells.

U-937 cells were split to 50% confluency (250,000 cells/mL) and treated with 2 mM thymidine for 10 hours. The cells were then pelleted (500 g, 3 minutes) and washed with PBS before being resuspended in thymidine-free media and allowed to recover for 13 hours. The cells were then re-blocked with 2 mM thymidine for 10 hours, and then washed with PBS as before and resuspended in media (250,000 cells/mL).

DMSO stocks of compounds were added to a 24-well plate in triplicate (0.2% DMSO final), after which 1 mL of the prepared cell suspension was added. Following a 16 h incubation, the cell suspensions were transferred to 2 mL tubes and pelleted (600 g, 3 min). The media was removed by aspiration, and the cells were fixed with 0.5 mL of ice cold 70% ethanol with vortexing. The samples were fully fixed at −20° C. for 3 hours. The samples were then pelleted (1000 g, 5 min) and the supernatant was removed via aspiration. The cells were incubated with 50 μL of 5 μg/mL RNAseA in PBS for 3 hours at room temperature. Prior to reading, the samples were taken up in 150 μL of 50 μg/mL propidium iodide in PBS and transferred to flow cytometry tubes. Samples were analyzed based on whole, single cells.

Tubulin Microscopy with HeLa Cells.

Round, 1.5 mm coverslips (No. 1.5) were sterilized with ultraviolet light and placed in a 12-well plate. HeLa cells (100,000 cells/well) were added and allowed to adhere for eight hours. Compounds were then added as DMSO stocks to achieve a final DMSO concentration of 1%, and the plates were returned to the incubator for 16 hours.

Following incubation, the media was removed, and the coverslips were fixed with 0.5 mL Microtubulin Stabilizing Buffer (MTSB, 80 mM PIPES, pH 6.8, 1 mM $MgCl_2$, 5 mM EGTA, 0.5% TX-100)+0.5% glutaraldehyde for 10 minutes at room temperature, after which the fixative was removed and the sample was quenched with the addition of 0.5 mL of freshly-prepared 1 mg/mL $NaBH_4$ in PBS. After a 5 min incubation, the solution was removed by aspiration and the coverslips were washed with PBS.

Coverslips were transferred to parafilm-lined culture dishes (cell-side up), and 40 μL of 50 μg/mL RNase A in Antibody Diluting Solution (AbDil, PBS, pH 7.4, 0.2% TX-100, 2% BSA, 0.1% $NaN_3$) with 1:50 dilution of anti-α-tubulin-FITC antibody was added to all samples. The samples were allowed to incubate at room temperature in the dark for 2.5 hours, after which the coverslips were washed three times with PBS+0.1% TX-100. The samples were then incubated for 2 minutes with 50 μL of 50 μg/mL PI in PBS. The coverslips were washed three times with PBS+0.1% TX-100, at which point they were mounted onto microscopy slides using Dako fluorescent mounting media, allowed to cure, and imaged on the Zeiss confocal LSM 510 (Jena, Germany).

Crystal Structure of 13-desbromo-methylester S25 was illustrated in FIG. 9.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

The invention claimed is:

1. A method for treating a cancer in a subject in need thereof, comprising administering to the subject a therapeutically effective amount of a compound of formula I:

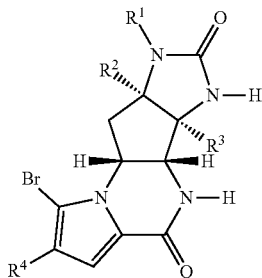

or a pharmaceutically acceptable salt thereof,
wherein:
$R^1$ is H or $CH_3$;
$R^2$ is —OH or —$OCH_3$;
$R^3$ is —H or —OH; and
$R^4$ is —H, or —Br when $R^1$ is —$CH_3$; and
wherein the cancer is cervical carcinoma, non-small cell lung carcinoma, or breast carcinoma, with the proviso that the compound is not:

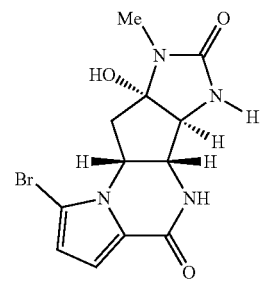 [SMILES: CN1C(=O)N[C@H]2[C@@H]3NC(=O)c4ccc(Br)n4[C@@H]3C[C@]21O]

wherein the cancer is cervical cancer and the compound is agelastatin B, D, or E, wherein the cancer is non-small cell lung carcinoma and the compound is agelastatin D, or wherein the cancer is breast carcinoma and the compound is agelastatin B, D, or E.

2. The method of claim 1, wherein $R^1$ is —$CH_3$.

3. The method of claim 1, wherein $R^2$ is —OH.

4. The method of claim 1, wherein $R^3$ is —H.

5. The method of claim 1, wherein $R^4$ is —Br when $R^1$ is —$CH_3$.

6. The method of claim 1, wherein the compound is

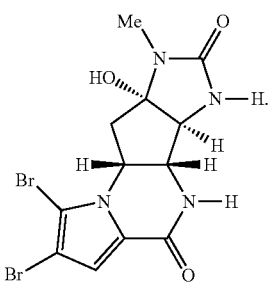

7. The method of claim 1, wherein the compound is

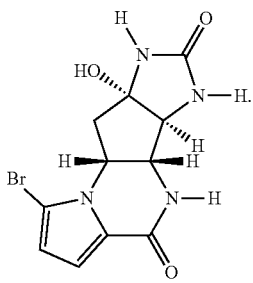

8. The method of claim 1, wherein the compound is

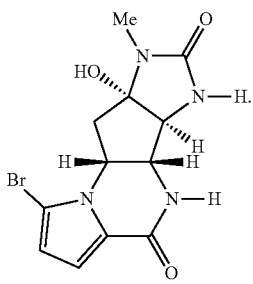

9. The method of claim 1, wherein the compound of formula I has no or low hemolytic activity at about 300 μM.

10. The method of claim 1, wherein the compound of formula I causes less than about 10% hemolysis two hours after administration at about 300 μM.

11. The method of claim 1, wherein the compound of formula I does not affect tubulin dynamics within cells.

12. The method of claim 1, wherein the compound of formula I is administered in a pharmaceutical composition comprising a compound of formula I or a pharmaceutically acceptable salt thereof.

13. The method of claim 12, wherein the pharmaceutical composition comprises a pharmaceutically acceptable carrier.

14. A method for treating blood cancer in a subject in need thereof, comprising administering to the subject a compound of formula I:

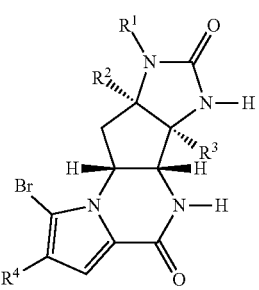

or a pharmaceutically acceptable salt thereof,
wherein:
$R^1$ is —H or —CH$_3$;
$R^2$ is —OH or —OCH$_3$;
$R^3$ is —H or —OH; and
$R^4$ is —H, or —Br when $R^1$ is —CH$_3$; and
wherein said method treats blood cancer, inhibits growth of blood cancer cells, inhibits proliferation of blood cancer cells, promotes apoptosis of blood cancer cells, arrests cell cycle in blood cancer cells, or induces arrest in G2/M phase in blood cancer cells, or any combination thereof wherein the compound is agelastain B, D, or E.

15. A method for treating a cancer in a subject in need thereof, comprising administering to the subject a therapeutically effective amount of a compound of formula I:

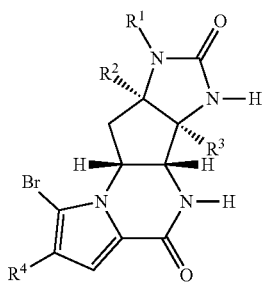

or a pharmaceutically acceptable salt thereof,
wherein:
$R^1$ is —H or —CH$_3$;
$R^2$ is —OH or —OCH$_3$;
$R^3$ is —H or —OH; and
$R^4$ is —H, or —Br when $R^1$ is —CH$_3$; and
wherein the cancer is cervical carcinoma wherein the compound is agelastain B, D, or E.

16. The method of claim 15, wherein $R^1$ is —CH$_3$.
17. The method of claim 15, wherein $R^2$ is —OH.
18. The method of claim 15, wherein $R^3$ is —H.
19. The method of claim 15, wherein $R^4$ is —Br when $R^1$ is —CH$_3$.
20. The method of claim 15, wherein the compound is

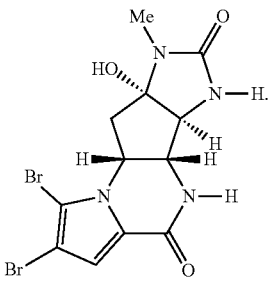

21. The method of claim 15, wherein the compound is

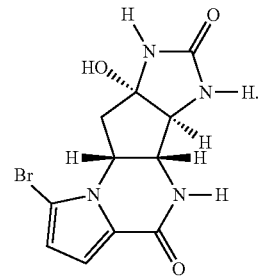

22. The method of claim 15, wherein the compound is

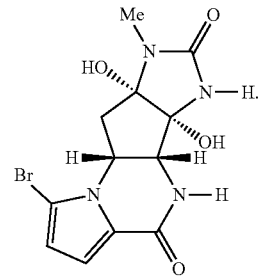

23. The method of claim 15, wherein the compound of formula I has no or low hemolytic activity at about 300 µM.

24. The method of claim 15, wherein the compound of formula I causes less than about 10% hemolysis two hours after administration at about 300 µM.

25. The method of claim 15, wherein the compound of formula I does not affect tubulin dynamics within cells.

26. The method of claim 15, wherein the compound of formula I is administered in a pharmaceutical composition comprising a compound of formula I or a pharmaceutically acceptable salt thereof.

27. The method of claim 26, wherein the pharmaceutical composition comprises a pharmaceutically acceptable carrier.

* * * * *